United States Patent [19]

Kimura et al.

[11] Patent Number: 5,668,136
[45] Date of Patent: Sep. 16, 1997

[54] TRISUBSTITUTED BENZENE DERIVATIVES, COMPOSITION AND METHODS OF TREATMENT

[75] Inventors: Teiji Kimura; Nobuhisa Watanabe; Yasutaka Takase; Kenji Hayashi; Makoto Matsui; Hironori Ikuta; Youji Yamagishi; Kozo Akasaka; Hiroshi Tanaka; Issei Ohtsuka; Takao Saeki; Motoji Kogushi, all of Ibaraki, Japan; Tohru Fujimori, Tenafly, N.J.; Isao Saito, Ibaraki, Japan

[73] Assignee: Eisai Co., Ltd., Tokyo, Japan

[21] Appl. No.: 757,908

[22] Filed: Sep. 11, 1991

[30] Foreign Application Priority Data

Sep. 25, 1990 [JP] Japan ................ 2-251897
Mar. 29, 1991 [JP] Japan ................ 3-091477

[51] Int. Cl.⁶ .............. A61K 31/495; A61K 31/415; C07D 241/04; C07D 233/54
[52] U.S. Cl. .............. 514/255; 514/256; 514/277; 514/315; 514/359; 514/381; 514/399; 514/403; 514/408; 514/597; 514/598; 544/335; 544/398; 544/402; 544/403; 546/192; 546/329; 546/330; 564/48; 564/49; 564/51; 564/52
[58] Field of Search .................. 544/400, 402, 544/403, 215, 242, 335, 398; 548/341, 346, 257, 302.1, 304.4, 316.4, 317.1, 317.5, 326.5, 335.1, 341.1, 341.5, 342.1, 342.5, 343.1, 343.5, 346.1, 252, 254, 255, 260, 309.7, 310.1, 338.1, 338.5; 514/255, 399, 393, 394, 395, 396, 398, 241, 256, 277, 315, 359, 381, 403, 408, 597, 598; 546/192, 329, 330; 564/48, 49, 50, 51, 52

[56] References Cited

U.S. PATENT DOCUMENTS 3,925,387 12/1975 Maruyama et al. ............ 260/268
4,623,662 11/1986 DeVries ............ 514/585
4,824,843 4/1989 Hoefle et al. ............ 514/228.8

FOREIGN PATENT DOCUMENTS

| | | |
|---|---|---|
| 0245687 | 11/1987 | European Pat. Off. |
| 0283742 | 9/1988 | European Pat. Off. |
| 0344425 | 12/1989 | European Pat. Off. |
| 0354994 | 2/1990 | European Pat. Off. |
| 0418071 | 3/1991 | European Pat. Off. |
| 0561175 | 9/1993 | European Pat. Off. |
| 0559898 | 9/1993 | European Pat. Off. |
| 2162168 | 7/1973 | France |
| 2259004 | 6/1973 | Germany |
| 2056968 | 3/1981 | United Kingdom |
| 2113684 | 8/1983 | United Kingdom |

OTHER PUBLICATIONS

CA 77:88820, 1972.
Cross et al., J. Med. Chem. 28, 1427–1432, 1985.
Database WPI, Derwent Publications Ltd., London, GB AN 81–38689D & GB–A–2 062 622 (American Cyanamid Co., Week 8122, 1981.
Chemical Abstracts, No. 117176d, vol. 119, No. 11, Sep. 13, 1993 and J. Med. Chem., vol. 36, No. 11, 1993 (pp. 1630–1640).
J. Med. Chem., vol. 21, No. 10, 1989 (pp. 2318–2325).

Primary Examiner—Yogendra N. Gupta

[57] ABSTRACT

A benzene, pyridine or pyrimidine derivative having the below shown formula is novel and useful as an anti-arteriosclerotic agent.

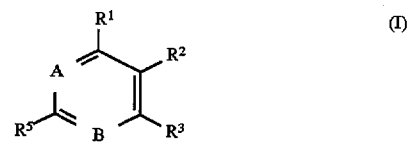

wherein $R^1$ stands for a lower alkyl group, an amino group which may be substituted, or the like; $R^2$ stands for a group represented by the formula:

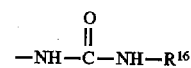

(wherein $R^{16}$ stands for an alkyl group having 1 to 6 carbon atoms, or the like) or the like; $R^3$ stands for a group represented by the formula: $-O-(CH_2)_m-Y$ (Y stands for an imidazolyl or piperazinyl group, or the like and m is 1 to 6) or the like; $R^5$ stands for a hydrogen atom, a lower alkyl group, or the like; A stands for a group represented by the formula:

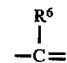

(wherein $R^6$ stands for a hydrogen atom, a lower alkyl group, or the like), $-N=$, or the like; and B stands for a group represented by the formula:

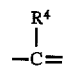

(wherein $R^4$ stands for a hydrogen or the like), $-N=$, or the like.

23 Claims, No Drawings

TRISUBSTITUTED BENZENE DERIVATIVES, COMPOSITION AND METHODS OF TREATMENT

[FIELD OF INDUSTRIAL APPLICATION]

The present invention relates to a benzene, pyridine or pyrimidine derivative or a pharmacologically acceptable salt thereof which has an excellent activity as a drug.

[BACKGROUND OF THE INVENTION AND PRIOR ART]

Cerebrovascular diseases such as cerebral apoplexy and cardiac infarction which rank high in the list of death causes in Japan are all caused by the sclerosis of the arteries.

Although hypolipidemic drugs which are effective in lowering the content of lipid, particularly cholesterol in the blood have been mainly used for the prevention and treatment of arteriosclerosis, no decisively effective drug has been found as yet.

Many studies have been made on arteriosclerosis and it has recently been found that an enzyme called ACAT (acyl-CoA: cholesterol O-acyl transferase) present in the arterial wall acts as an important factor in the formation of fat striae which are observed in arteriosclerosis (atherosclerosis).

That is, the formation of cholesterol ester on the arterial wall is catalyzed by the ACAT, so that an increase in the amount of the ACAT participates in the excess accumulation of cholesterol ester. Accordingly, it is expectable that the excess accumulation of cholesterol ester on the arterial wall may be controlled by the inhibition of the ACAT.

Meanwhile, the ACAT is also known to participate in the intestinal absorption of cholesterol. That is, dietary cholesterol and cholesterol discharged into the intestines by the adaptation of a living body itself in a state mixed with bile are absorbed as free cholesterol, esterified by the action of the ACAT, packed into chylomicrons and discharged into the blood. Accordingly, it is expectable that the intestinal absorption of cholesterol may be controlled by the inhibition of the ACAT in the intestines.

The inventors of the present invention have eagerly studied for many years on a compound which exhibits an inhibitory activity against the ACAT of the arterial wall and the intestines to thereby hinder the excess accumulation of cholesterol ester on the arterial wall and the intestinal absorption of cholesterol with their attentions being paid to the ACAT to find out that a benzene or pyrimidine derivative or a pharmacologically acceptable salt thereof can attain the object as will be described below.

Although compounds exhibiting an inhibitory activity against the ACAT have been proposed in, for example, U.S. Pat. Nos. 4,623,662, 4,489,094, 4,489,090, 4,824,843 and 4,285,951 and Japanese Patent Laid-Open Nos. 134070/1983, 231058/1984, 41655/1985, 277351/1987, 258366/1987, 23848/1988, 253060/1988, 19016/1989, 93569/1989, 203360/1989, 6455/1990, 6457/1990 and 6456/1990, the compounds of the present invention are different from them in the chemical structures.

(SUMMARY OF THE INVENTION)

The compound of the present invention is a benzene, pyridine or pyrimidine derivative represented by the following general formula (I) or a pharmacologically acceptable salt thereof.

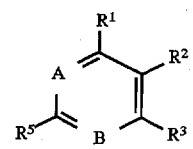

wherein $R^1$ stands for a hydrogen or halogen atom, a lower alkyl, lower alkoxy, nitro or cyano group, a group represented by the formula:

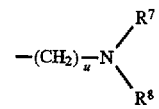

(wherein $R^7$ and $R^8$ may be the same or different from each other and each stands for a hydrogen atom or a lower alkyl or lower alkylsulfonyl group and u is 0 or an integer of 1 or 2, alternatively, $R^7$ and $R^8$ may form a ring together with the nitrogen atom to which $R^7$ and $R^8$ are bonded), a group represented by the formula: $-CH_2OR^9$ (wherein $R^9$ stands for a hydrogen atom or a lower alkyl group), a group represented by the formula: $-COOR^{10}$ (wherein $R^{10}$ stands for a hydrogen atom or a lower alkyl group), a group represented by the formula:

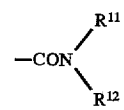

(wherein $R^{11}$ and $R^{12}$ may be the same or different from each other and each stands for a hydrogen atom or a lower alkyl group) or a group represented by the formula:

(wherein t is 0 or an integer of 1 or 2; and $R^{13}$ stands for a hydrogen atom or a lower alkyl group;

$R^2$ stands for a group represented by the formula:

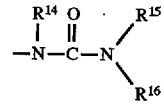

(wherein $R^{14}$, $R^{15}$ and $R^{16}$ may be the same or different from each other and each stands for a hydrogen atom or an alkyl, cycloalkyl, alkenyl or alkyloxyalkyl group. Alternatively, $R^{15}$ and $R^{16}$ may form a ring together with the nitrogen atom to which $R^{15}$ and $R^{16}$ are bonded), a group represented by the formula:

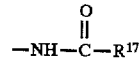

(wherein $R^{17}$ stands for an alkyl group), a group represented by the formula: $-NH-R^{18}$ (wherein $R^{18}$ stands for an alkyl group) or a group represented by the formula:

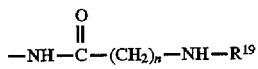

(wherein $R^{19}$ stands for an alkyl group and n is an integer of 1 to 3);

$R^3$ stands for a group represented by the formula: —$(CH_2)_p$—X—$(CH_2)_m$—Y (wherein X stands for a group represented by the formula: —O—, —S—,

—$SO_2$—, —NH—, —$CH_2$— or —CH=CH—; p is 0 or 1; m is an integer of 1 to 6; Y is a 5- or 6-membered aromatic heterocyclic group including 1 to 4 nitrogen atoms which may have a substituent(s), a 5- or 6-membered saturated heterocyclic group having 1 to 3 nitrogen atoms which may have a substituent(s), or a lower alkoxy group), a group represented by the formula:

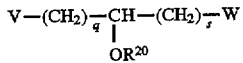

(wherein V stands for a group represented by the formula: —O—, —S—,

—$SO_2$—, —NH— or —$CH_2$—; q and s are each an integer of 1 to 6; $R^{20}$ stands for a hydrogen atom or a lower alkyl group; W is the same definition as Y);

A stands for a group represented by the formula:

wherein $R^6$ stands for a hydrogen atom, a lower alkyl group, a halogen atom or a group represented by the formula: —$(CH_2)_p$—X—$(CH_2)_m$—Y (wherein p, X, m and Y are each as defined above)) or a group represented by the formula: —N=;

B stands for a group represented by the formula:

[wherein $R^4$ stands for a hydrogen or halogen atom or a group represented by the formula —$(CH_2)_p$—X—$(CH_2)_m$—Y (wherein p, X, m and Y are each as defined above)] or a group represented by the formula: —N=; and $R^5$ stands for a hydrogen atom, a lower alkyl group or a group represented by the formula: —$(CH_2)_p$—X—$(CH_2)_m$—Y (wherein p, X, m and Y are each as defined above);

In addition to the above definition with respect to $R^1$ $R^4$, $R^5$ and $R^6$, $R^1$, $R^4$, $R^5$ and $R^6$ may form a benzene ring which may be substituted together with the carbon atoms which are adjacent to each other and to which they are bonded. The compound of the present invention has a specific inhibitory activity against the ACAT which is one of the enzymes participating in the formation of foam cells and therefore can inhibit the sideration and evolution of arteriosclerosis.

Among the compounds of the invention, the benzene derivative having the formula in which A is —CR6= and B is —CR4= is preferable. The benzene compound having the formula (II), below shown, is more preferable. It is most preferable that $R^a$ is methyl or dimethylamino, R16 is an alkyl having 1 to 6 carbon atoms or an alkyl having 2 to 4 carbon atoms, Y is piperazinyl, imidazolyl or an imidazolyl having a substituent(s) such a a lower alkyl having 1 to 6 carbon atoms, a halogen atom and phenyl and M is an integer of 1 to 6.

The most impotant compounds are shown in Examples 1, 37, 54, 64, 80, 81, 93, 127 and 131, 2, 3 and 17.

The invention further provides a composition comprising a pharmacoligically effective amount of the derivative of the invention and a pharmacologically acceptable carrier and an ACAT enzyme inhibitor comprising the derivative of the invention.

The invention moreover provides a phamaceutical use of the derivative of the invention, such as a remedy for diseases for which an ACAT enzyme inhibiting action is effective and a method for treatment of the disease, in particular an arteriosclerosis remedy.

In the above definition, the lower alkyl group defined with respect to $R^1$, $R^5$, $R^6$, $R^7$, $R^8$, $R^9$, $R^{10}$, $R^{11}$, $R^{12}$, $R^{13}$ and $R^{20}$ is a straight-chain or branched one having 1 to 6 carbon atoms and examples thereof include methyl, ethyl, n-propyl, isopropyl, n-butyl, isobutyl, sec-butyl, tert-butyl, n-pentyl (amyl), isopentyl, neo-pentyl, 1-methylbutyl, 2-methylbutyl, 1,2-dimethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl groups. Among these groups, methyl, ethyl, propyl and isopropyl groups are preferable and methyl and ethyl groups are most desirable.

The lower alkoxy group defined with respect to $R^1$, Y and W includes those respectively derived from the lower alkyl groups derived above, for example, methoxy, ethoxy and n-propoxy groups, among which methoxy group is most desirable.

The aromatic heterocyclic ring for Y may be monocyclic or fused cyclic such as benzoimidazolyl.

The lower alkyl group constituting the lower alkylsulfonyl group defined with respect to $R^7$ and $R^8$ may be any one selected from among those described above and the most desirable lower alkylsulfonyl group is a methylsulfonyl group.

The halogen atom defined with respect to $R^1$, $R^4$ and $R^6$ includes chlorine, bromine and fluorine atoms.

The alkyl group defined with respect to $R^{14}$, $R^{15}$ $R^{16}$, $R^{17}$, $R^{18}$ and $R^{19}$ is preferably a straight-chain or branched alkyl group having 1 to 10 carbon atoms. The alkyl group includes n-heptyl, n-octyl, n-nonyl and n-decyl groups and branched alkyl groups in addition to the above-described alkyl groups having 1 to 6 carbon atoms. Among these alkyl groups, straight-chain or branched alkyl groups having 1 to 8 carbon atoms are preferable, among which methyl, ethyl, n-propyl, isopropyl, n-butyl and n-pentyl groups are particularly preferable.

To enter into more details, among the groups of the formula:

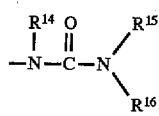

defined with respect to R², a case wherein R¹⁴ and R¹⁵ are each a hydrogen atom and R¹⁶ is an alkyl group is most desirable and a case wherein R¹⁴ is a hydrogen atom, R¹⁵ is a methyl group and R¹⁶ is an alkyl group comes next. In these cases, R¹⁶ is preferably an alkyl group having 1 to 10 carbon atoms, still preferably one having 2 to 6 carbon atoms.

Further, in the group of the formula:

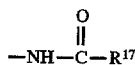

or —NH—R¹⁸ defined with respect to R², R¹⁷ and R¹⁸ are each an alkyl group as described above, preferably one having 1 to 10 carbon atoms, still preferably one having 4 to 8 carbon atoms.

Further, the cycloalkyl group defined with respect to R¹⁴, R¹⁵ and R¹⁶ is, for example, one having 3 to 6 carbon atoms. That is, the cycloalkyl group includes cyclopropyl, cyclobutyl, cyclopentyl and cycloheptyl groups.

The alkenyl group defined with respect to R¹⁴, R¹⁵ and R¹⁶ includes those respectively derived from the alkyl groups having 1 to 6 carbon atoms defined with respect to, e.g., R¹, R⁵, R⁶, R⁷, R⁸, R⁹ and R¹⁰. Preferable examples thereof include alkenyl groups having 3 to 6 carbon atoms such as allyl, 2-butenyl, isobutenyl, 2-pentenyl and 3-methyl-2-butenyl groups.

In the group of the formula:

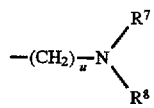

defined with respect to R¹, a case wherein R⁷ and R⁸ are each a methyl group is most desirable.

Alternatively, R⁷ and R⁸ may form a ring together with the nitrogen atom to which they are bonded. Particularly, they may form a piperidine, pyrrolidine or pyrrolidone ring which may be substituted with a lower alkyl group such as a methyl group.

When R¹ is an alkyl group, the lower alkyl group is most desirably a methyl group, though it may be any one selected from among those described above.

In the above general formula (I) specifying the compound of the present invention, A stands for a group represented by the formula:

[wherein R⁶ stands for a hydrogen atom, a lower alkyl group, a halogen atom or a group represented by the formula: —(CH₂)ₚ—X—(CH₂)ₘ—Y (wherein p, X, m and Y are each as defined above)] or a group represented by the formula: —N═, while B stands for a group represented by the formula:

[wherein R⁴ stands for a hydrogen or halogen atom or a group represented by the formula: —(CH₂)ₚ—X—(CH₂)ₘ—Y (wherein p, X, m and Y are each as defined above)] or a group represented by the formula: —N═. Particularly, when A is a group represented by the formula:

(wherein R⁶ is as defined above) and B is a group represented by the formula:

(wherein R⁴ is as defined above), the objective compound according to the present invention is represented by the following general formula:

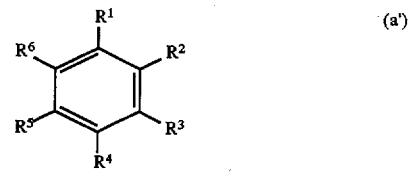

(a')

Further, when A and B are each a group represented by the formula: —N═, the objective compound according to the present invention is represented by the following general formula:

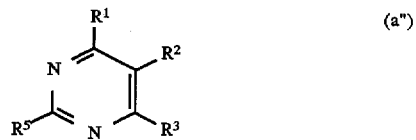

(a")

Furthermore, R¹, R⁴, R⁵ and R⁶ may form a benzene ring which may be substituted together with the carbon atoms which are adjacent to each other and to which they are bonded. Particularly, R¹ and R⁶, R⁶ and R⁵ or R⁵ and R⁴ may together form a benzene ring to give a naphthalene ring as represented by the following formula:

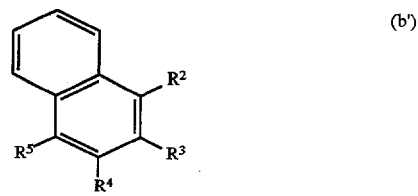

(b')

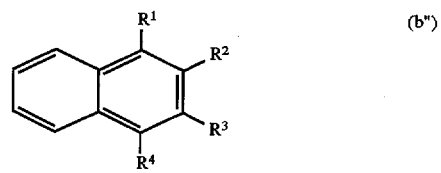

(b")

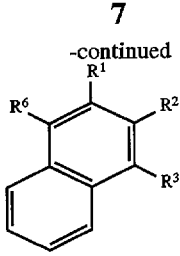

The alkenyl group defined with respect to $R^{14}$, $R^{15}$ and $R^{16}$ is one derived from an alkyl group as described above, i.e., a group having one or more carbon-carbon double bonds. Particular examples thereof include groups respectively represented by the formulas:

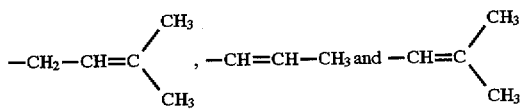

Further, the cycloalkyl group defined with respect thereto includes cyclopropyl, cyclobutyl, cyclopentyl and cyclohexyl groups. Furthermore, the alkyloxyalkyl group defined with respect thereto is an alkyl group as described above having an ether linkage represented by the formula: —O— between carbon atoms and particular examples thereof include those represented by the formulas: —CH$_2$—CH$_2$—O—CH$_2$—CH$_3$, —CH$_2$—O—CH$_2$—CH$_3$, —CH$_2$—O—CH$_2$—CH$_3$, —CH$_2$—CH$_2$—CH$_2$—O—CH$_3$, —CH$_2$—CH$_2$—O—CH$_2$—CH$_3$ and —CH$_2$—CH$_2$—O—CH$_3$. That is, the alkyloxyalkyl group is represented by the following formula:

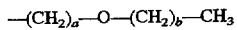

wherein a is an integer of 1 to 6 and b is 0 or an integer of 1 to 5.

Alternatively, $R^{15}$ and $R^{16}$ may form a ring together with the nitrogen atom to which they are bonded and the ring includes those respectively represented by the formulas:

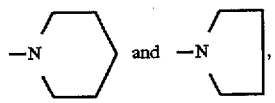

which may be substituted with a lower alkyl group such as a methyl group.

Among the groups represented by the formula: —(CH$_2$)$_p$—X—(CH$_2$)$_m$—Y (wherein X stands for a group represented by the formula: —O—, —S—, —SO$_2$—, —NH—, —CH$_2$— or —CH=CH—; p is 0 or 1; m is an integer of 1 to 6; and Y stands for a 5- or 6-membered aromatic heteromonocyclic group having 1 to 4 nitrogen atoms or 5- or 6-membered saturated hetero-monocyclic group having 1 to 3 nitrogen atoms, which may be substituted, or a lower alkoxy group) defined with respect to $R^3$, $R^4$, $R^5$ and $R^6$, a group wherein X is a group represented by the formula: —O— is most desirable and a group wherein X is a group represented by the formula: —CH2— comes is next.

Y is preferred to be a 5- or 6-membered aromatic heteromonocyclic group having 1 to 4 nitrogen atoms or a 5- or 6-membered saturated heteromonocyclic group having 1 to 3 nitrogen atoms, which may be substituted, or a lower alkoxy group. Particular examples of the 5- or 6-membered aromatic hetero-monocyclic group having 1 to 4 nitrogen atoms and the 5- or 6-membered saturated hetero-monocyclic group having 1 to 3 nitrogen atoms include

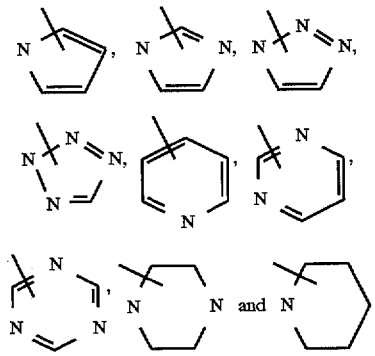

Among these groups, an imidazolyl group is most desirable.

The aromatic hetero-monocyclic group or saturated hetero-monocyclic group may have 1 to 3 substituents selected from among (a) lower alkyl groups (ones having 1 to 6 carbon atoms as defined above, for example, methyl, ethyl and n-propyl groups), (b) substituted and unsubstituted aryl groups such as phenyl and naphthyl groups [the substituent including lower alkyl groups as defined above such as a methyl group; lower alkoxy groups such as a methoxy group; lower alkylsulfonyl groups such as a methylsulfonyl group; halogen atoms such as chlorine, bromine and fluorine atoms; a nitro group; lower alkylsulfonylamino groups such as a methylsulfonylamino group (the lower alkyl group being as defined above) and di(lower alkyl)sulfonylamino groups (the lower alkyl group being as defined above) such as a dimethylsulfonylamino group], (c) groups represented by the formula: —(E)$_a$—COOR$^{21}$ (wherein E stands for an alkylene or alkenylene group having 1 to 6 carbon atoms; R$^{21}$ stands for a hydrogen atom, a residue constituting a carboxylate ester, for example a lower alkyl group such as a methyl group, or a residue constituting a carboxamide, for example, an amino group; and a is 0 or 1), (d) groups represented by the formula: —(CH$_2$)$_v$—OH (wherein v is 0 or an integer of 1 to 6), (e) halogen atoms such as chlorine, bromine and fluorine, (f) groups represented by the formula: —(CH$_2$)$_b$—NH—(CH$_2$)$_c$—CH$_3$ (wherein b is 0 or an integer of 1 to 4 and c is 0 or an integer of 1 to 5), (g) groups represented by the formula: —(CH$_2$)$_d$—SO$_2$R$^{22}$ (wherein d is 0 or an integer of 1 to 6. and R$^{22}$ stands for a lower alkyl group as defined above), and (h) groups represented by the formula:

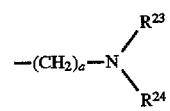

(wherein e is an integer of 1 to 6; and R$^{23}$ and R$^{24}$ may be the same or different from each other and each stand for a hydrogen atom or a lower alkyl group as defined above).

The above hetero-monocyclic groups may each have either one or more substituents. Further, the aryl group defined in the item (b) may also have either one or more substituents.

Further, the substituents of the 5- or 6-membered aromatic hetero-monocyclic group having 1 to 4 nitrogen atoms may form a ring together with the carbon atoms which constitute the hetero-monocycle and are adjacent to each other to give a condensed ring group and compounds represented by the formula (I) wherein Y is such a condensed ring group are involved in the present invention. Examples of the condensed ring group include

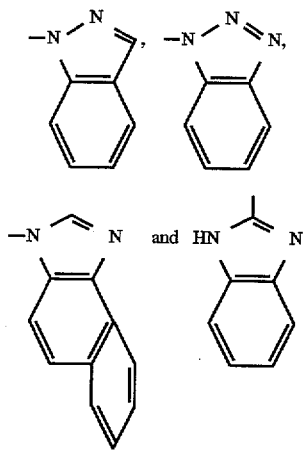

These condensed ring groups may each have a substituent as described above on any of the rings.

Although the group of the formula:

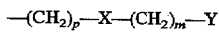

(wherein p, X, m and Y are each as defined above) which has been described above may be present as one or more of $R^3$, $R^4$, $R^5$ and $R^6$, it is most desirable that the group be present as $R^3$.

Among the benzene, pyridine and pyrimidine derivatives (I) and pharmacologically acceptable salts thereof according to the present invention, a group of desirable compounds are represented by the following general formula (II):

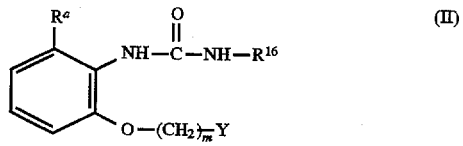

wherein $R^a$ stands for a lower alkyl group as defined above or a group represented by the formula:

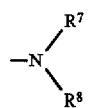

(wherein $R^7$ and $R^8$ may be the same or different from each other and each stands for a hydrogen atom or a lower alkyl group as defined above), and particularly $R^a$ is most desirably a methyl group and $R^7$ and $R^8$ are most desirably each a methyl group; although $R^{16}$ is as defined above, it is preferably an alkyl group having 1 to 6 carbon atoms; m is an integer of 1 to 6, preferably of 2 to 4; although Y is as defined above, it is most desirably an imidazolyl or piperazinyl group, and the imidazolyl group may be unsubstituted or substituted and preferable examples of the substituent include lower alkyl groups such as methyl, ethyl, n-propyl and isopropyl groups; halogen atoms such as chlorine and fluorine; and phenyl group. Particularly, a di-substituted imidazolyl group gives the most desirable results.

The salt acceptable as a drug may be any one so far as it is permittable according to the present invention and examples thereof include alkali metal salts; such as sodium salt and potassium salt; ammonium salt; quaternary ammonium salts such as tetraethylammonium salt and betaine salt; alkaline earth metal salts such as calcium salt and magnesium salt; inorganic acid salts such as hydrochloride, hydrobromide hydriodide sulfate carbonate and bicarbonate; organic carboxylic acid salts such as acetate, maleate, lactate and tartrate; organic sulfonates such as methanesulfonate, hydroxymethanesulfonate, hydroxyethanesulfonate, taurine salt, benzenesulfonate and toluenesulfonate; amino acid salts such as argininate, lysinate, serinate, aspartate, glutamate and glycinate; and amine salts such as trimethylamine salt, triethylamine salt, pyridine salt, procaine salt, picoline salt, dicyclohexylamine salt, N,N'-dibenzylethylenediamine salt, N-methylglucamine salt, diethanolamine salt, triethanolamine salt, tri(hydroxymethylamino)methane salt and phenethylbenzylamine salt.

Representative processes for the preparation of the compounds according to the present invention will now be described.

Preparation Process 1

A compound represented by the formula (I) wherein $R^3$ is a group represented by the formula: —O—$(CH_2)_m$—Y can be prepared by, for example, the following process:

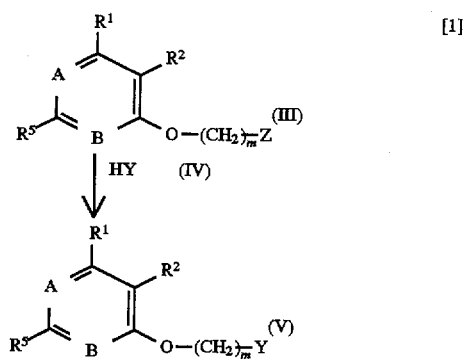

wherein A, B, $R^1$, $R^2$, $R^5$, m and Y are each as defined above; and Z stands for a halogen atom or an alkylsulfonyloxy or arylsulfonyloxy group.

That is, a compound (V) which is one of the objective compounds according to the present invention is prepared by condensing a compound represented by the general formula (III) with a compound represented by the general formula (IV) in the presence of a base according to a conventional process. The base includes alkali metal halides such as sodium iodide and sodium bromide.

The solvent to be used in the above condensation includes ethers such as tetrahydrofuran and dioxane; aromatic hydrocarbons such as benzene and toluene; and aliphatic hydrocarbons such as hexane, acetone and butanone.

[2] A compound represented by the formula (V) wherein Y is a group represented by the formula:

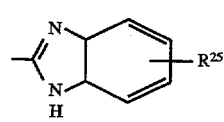

can be prepared also by the following process:

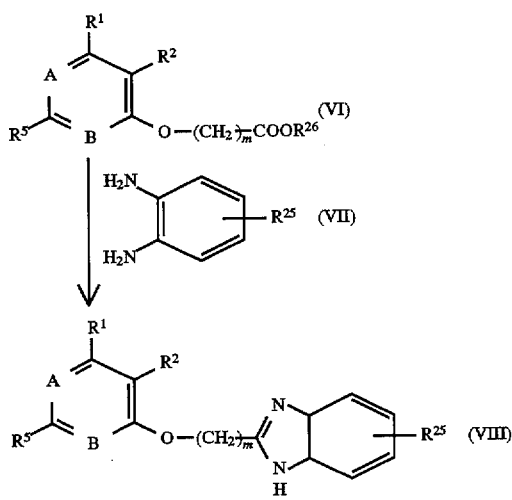

wherein A, B, $R^1$, $R^2$, $R^5$ and m are each as defined above; $R^{25}$ stands for a hydrogen or halogen atom or a lower alkyl, alkoxy or alkylamine group; and $R^{26}$ stands for a hydrogen atom, a lower alkyl group or a halogen atom.

That is, a compound represented by the general formula (VIII) which is one of the objective compounds according to the present invention is prepared by reacting a compound represented by the general formula (VI) with a compound represented by the formula (VII).

The above reaction is generally conducted by adding about 1 to 5 times (by mole) as much a compound represented by the general formula (VII) to a compound represented by the general formula (VI) and stirring the obtained mixture at a temperature of 0° C. to a reflux temperature for 30 minutes to 72 hours. The solvent usable in the reaction includes ethers such as tetrahydrofuran and dioxane; aprotic polar solvents such as dimethylformamide and dimethyl sulfoxide; aromatic hydrocarbons such as benzene and toluene; alcohols such as butanol and ethanol; halogenated hydrocarbons such as chloroform and dichloromethane; organic acids such as acetic acid; acetates such as ethyl acetate and methyl acetate; and mixtures of two or more of them.

Preparation Process 2

A compound represented by the general formula (I) wherein $R^3$ is a group represented by the formula: —NH—$(CH_2)_m$—Y can be prepared by, for example, the following process:

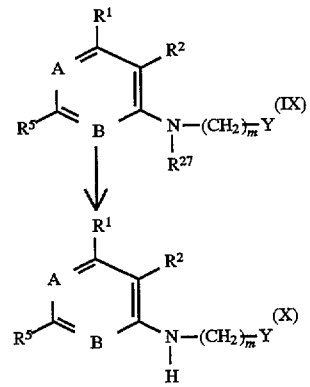

wherein A, B, $R^1$, $R^2$, $R^5$, m and Y are each as defined above; and $R^{27}$ stands for a hydrogen atom or a benzyl, formyl or alkylamide group.

That is, this reaction comprises converting a tertiary amine represented by the general formula (IX) into a secondary amine by a conventional process.

A compound represented by the general formula (IX) wherein $R^{27}$ is a formyl group is stirred in an alcoholic solvent in the presence of a catalytic amount of a mineral acid such as hydrochloric acid at a temperature of 0° C. to a reflux temperature to give a compound represented by the general formula (X) which is one of the objective compounds according to the present invention.

A compound represented by the general formula (IX) wherein $R^{27}$ is an alkylamide group is reacted with 1 to 10 times (by mole) as much an alkali metal hydroxide such as caustic potash or caustic soda in an alcoholic solvent at a temperature of 0° C. to room temperature under stirring to give a compound represented by the general formula (X) which is one of the objective compounds.

Preparation Process 3

A compound represented by the general formula (I) wherein $R^3$ is a group represented by the general formula: —$(CH_2)_{r+2}$—Y can be prepared by, for example, the following process:

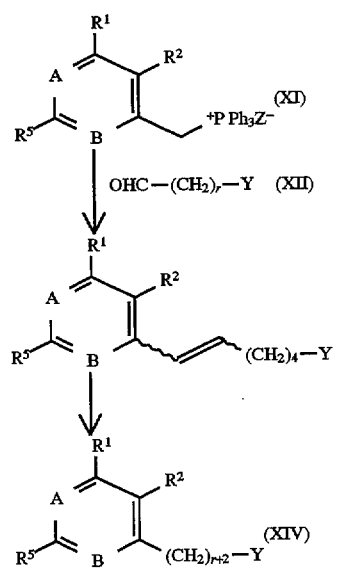

wherein A, B, $R^1$, $R^2$, $R^5$, Y and Z are each as defined above; and r is an integer of 1 to 4.

That is, a compound represented by the formula (XIII) is prepared by reacting a triphenylphosphonium compound represented by the general formula (XI) with an aldehyde represented by the general formula (XII) in the presence of a base, e.g., alkali metal hydroxide such as caustic soda or caustic potash at a temperature of room temperature to a reflux temperature according to a conventional process. It is preferable to use a base e.g., an alkali metal hydroxide such as caustic soda or caustic potash in the above reaction.

The thus-prepared compound represented by the general formula (XIII) is vigorously stirred in a hydrogen stream of normal pressure to 5 atm at a temperature of room temperature to 100° C. to give a compound represented by the general formula (XIV) which is one of the objective compounds.

The above reaction is conducted in the presence of a solvent and examples of the solvent include ethers such as tetrahydrofuran and dioxane; aprotic polar solvents such as dimethylformamide and dimethyl sulfoxide; aromatic hydrocarbons such as benzene and toluene; aliphatic hydrocarbons such as hexane; halogenated hydrocarbons such as chloroform and dichloromethane; acetates such as methyl acetate and ethyl acetate; organic acids such as acetic acid; and mixtures of two or more of them.

Now, processes for the preparation of the objective compounds according to the present invention wherein $R^2$ and/or $R^3$ are varied will be shown by reaction schemes.

In the following reaction schemes, A, B, $R^1$, $R^3$, $R^5$, Y, Z, m and r are each as defined above; $R^{28}$ stands for an acyl or carbamoyl group;

$R^{29}$ is hydrogen or a group having the formula: $-(CH_2)_m-Y$ (wherein m and Y are each as defined above); $R^{30}$ stands for a lower alkyl group or a hydrogen or halogen atom; $R^{31}$ stands for a hydrogen or halogen atom or a lower alkyl, alkoxy or alkylamino group; $R^{32}$ stands for a group represented by the formula: $-(CH_2)_p-X-(CH_2)_m-Y$ (wherein p, X, m and Y are each as defined above); $R^{33}$ stands for a hydrogen atom or a benzyl, formyl or alkylamide group; and Ph stands for a phenyl group.

Preparation process A

R3 is a lower alkoxy.

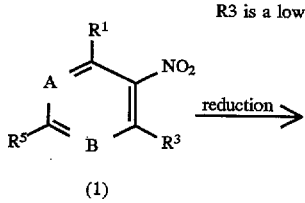

(1)

reduction →

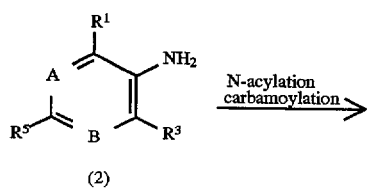

(2)

N-acylation carbamoylation →

-continued
Preparation process A

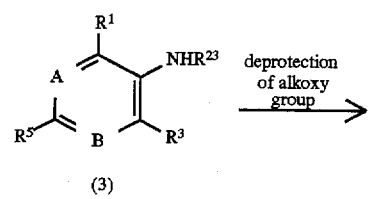

(3)

deprotection of alkoxy group →

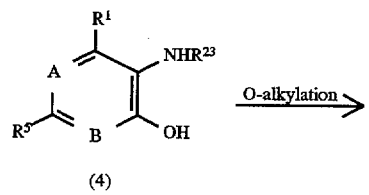

(4)

O-alkylation →

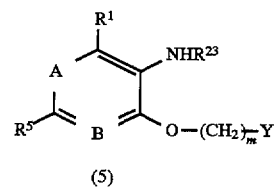

(5)

Preparation process B

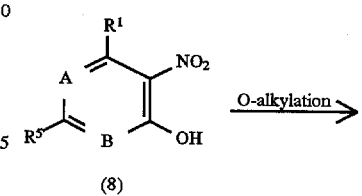

(8)

O-alkylation →

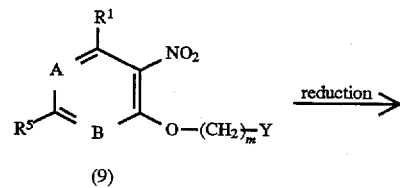

(9)

reduction →

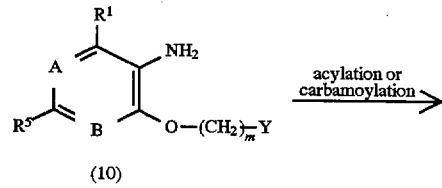

(10)

acylation or carbamoylation →

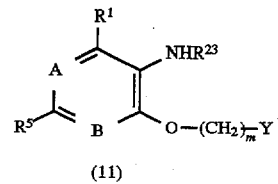

(11)

Preparation process C

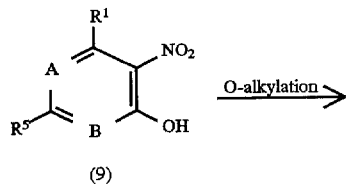
(9)

→ O-alkylation

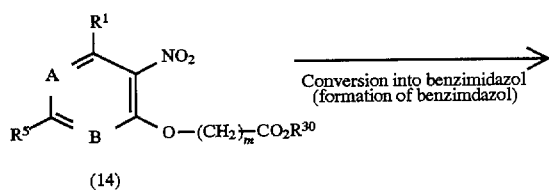
(14)

→ Conversion into benzimidazol (formation of benzimdazol)

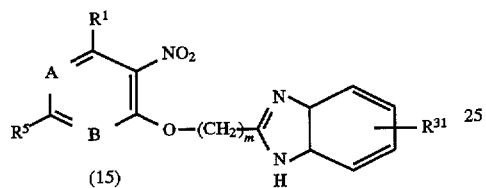
(15)

Preparation process D

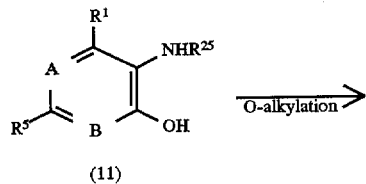
(11)

→ O-alkylation

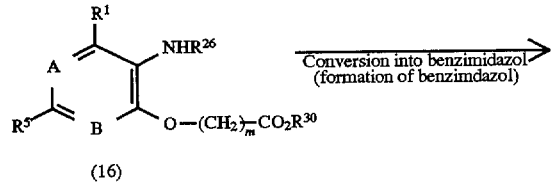
(16)

→ Conversion into benzimidazol (formation of benzimdazol)

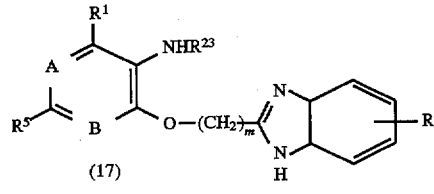
(17)

Preparation process E

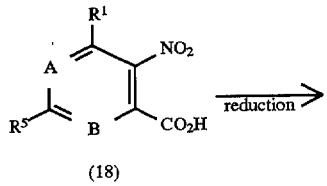
(18)

→ reduction

Preparation process E

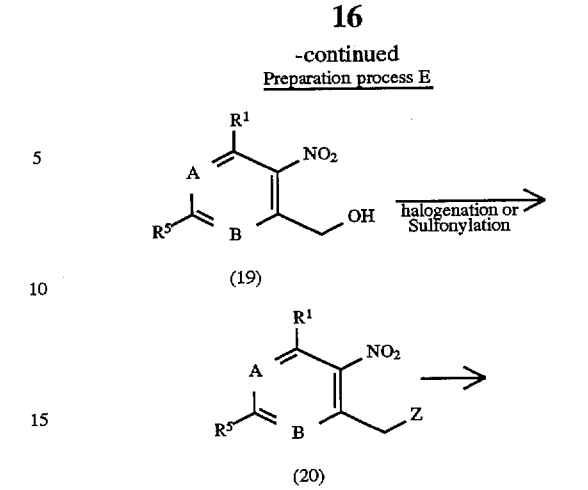
(19)

→ halogenation or Sulfonylation (20)

→ Coversion into phosphonium salt (formation of phosphonium salt) / Wittig reaction

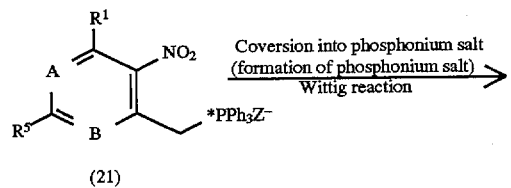
(21)

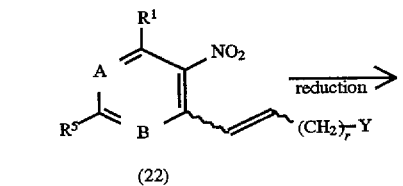
(22)

→ reduction

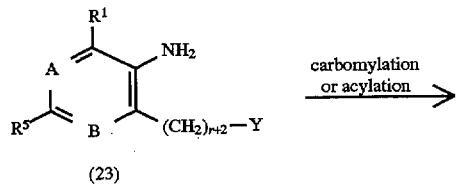
(23)

→ carbomylation or acylation

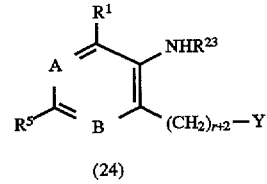
(24)

Preparation process F

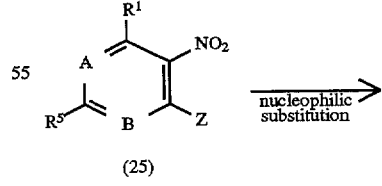
(25)

→ nucleophilic substitution

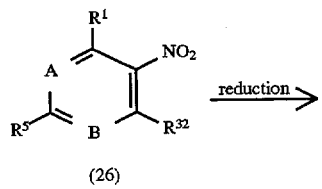
(26)

→ reduction

Preparation process F

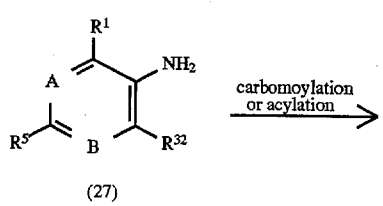

(27)

↓ carbomoylation or acylation

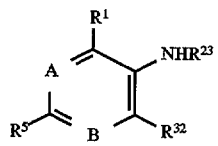

(28)

Preparation process G

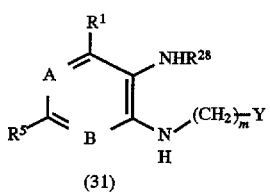

(29)

↓ N-alkylation

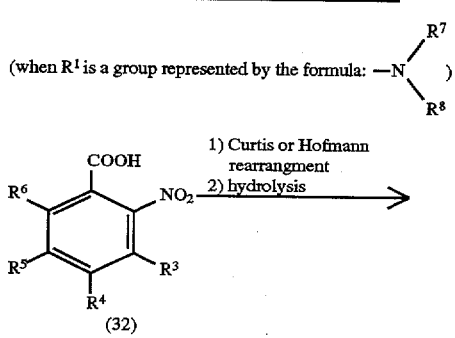

(30)

↓ carbomoylation or acylation (31)

The compound (1) which is important as a starting material in the above preparation process can be prepared by, e.g., the following processes:

Preparation process (i)

(when $R^1$ is a group represented by the formula: $-N\begin{pmatrix}R^7\\R^8\end{pmatrix}$)

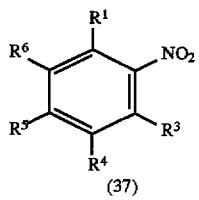

1) Curtis or Hofmann rearrangment
2) hydrolysis
→

(32)

Preparation process (i) -continued

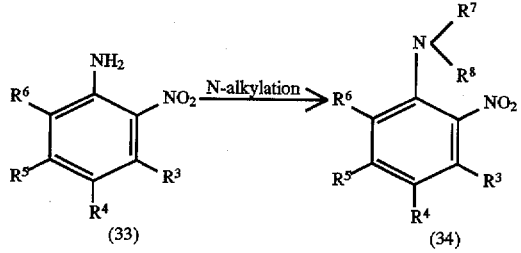

(33)    (34)

wherein $R^3$, $R^4$, $R^5$, $R^6$, $R^7$ and $R^8$ are each as defined above, with the proviso that at least one of $R^3$ to $R^6$ is a lower alkoxy group.

Preparation process (ii)

(when $R^1$ is a lower alkoxy group)

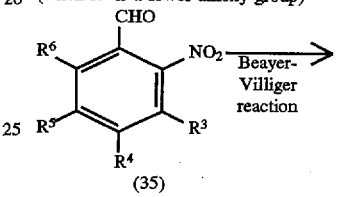

(35)

↓ Beayer-Villiger reaction

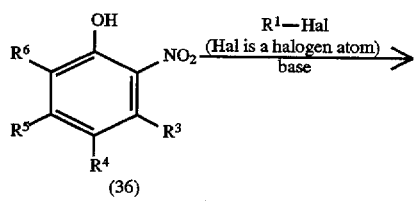

(36)

↓ $R^1$—Hal (Hal is a halogen atom) base

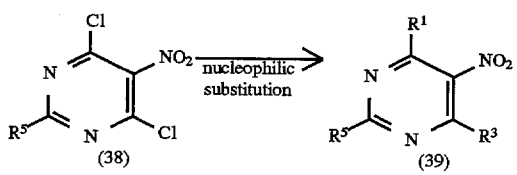

(37)

Preparation process (iii)

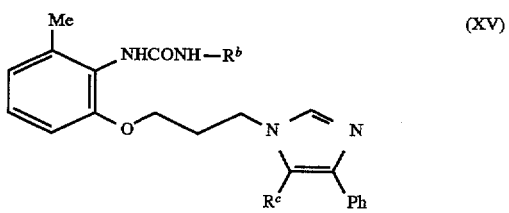

(38)    nucleophilic substitution →    (39)

Among the compounds according to the present invention, for example, a group of compounds each represented by the following general formula (XV):

(XV)

wherein $R^b$ stands for an alkyl, cycloalkyl or alkenyl group; $R^c$ stands for a hydrogen atom or a lower alkyl group; Ph stands for a phenyl group; and Me stands for a methyl group, are preferable.

Although such compounds of the formula (XV) can be prepared by the above-mentioned processes, they can be prepared also by the following process:

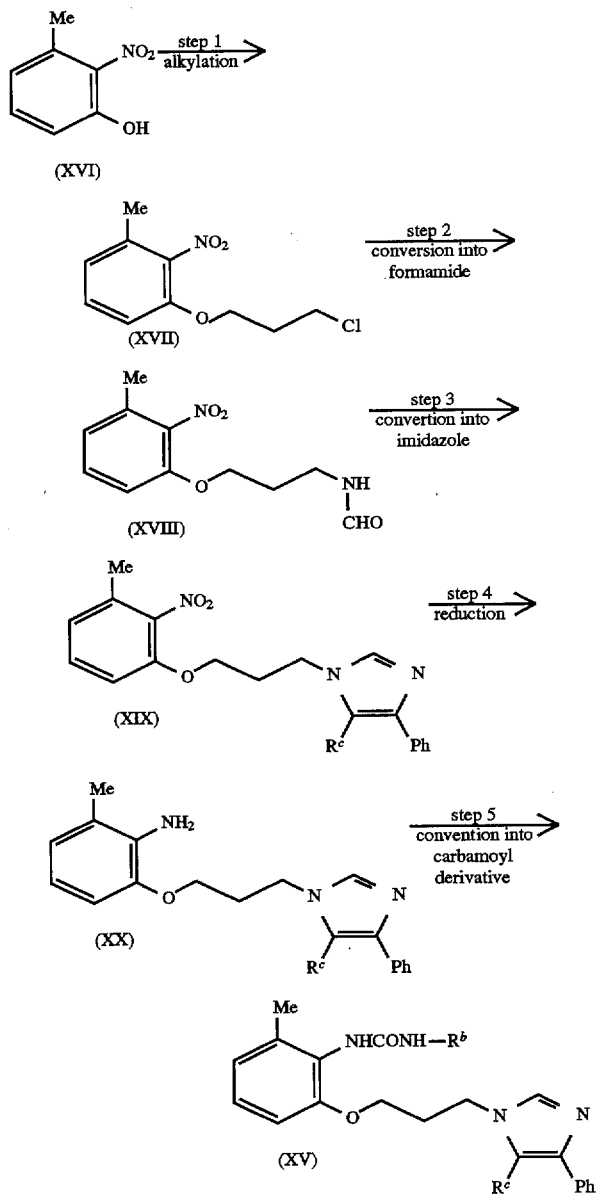

In the step 1 which is a conventional alkylation step, a compound (XVI) is reacted with, e.g., Br—$CH_2$—$CH_2$—$CH_2$—Cl generally in the presence of a base to give a compound (XVII). In the step 2, the compound (XVII) is converted into a formamide derivative. For example, the compound (XVII) is reacted with Na(CHO)$_2$, followed by the addition of an alkali such as KOH to give a compound (XVIII). The compound (XVIII) is converted into an imidazole derivative (XIX) in the step 3 by reacting the compound (XVIII) with a compound represented by the formula: Ph—CO—CHZ—$R^c$ (XXI) (wherein $R^c$ stands for a lower alkyl group; and Z stands for a halogen atom) in the presence of a base. The base includes alkali metal hydroxides such as caustic potash and caustic soda; alkali metal alcoholates such as sodium ethoxide and sodium methoxide; alkali metal hydrides such as sodium hydride and potassium hydride; alkali metals such as sodium and potassium; tertiary amines such as triethylamine and pyridine; and alakali metal carbonates and bicarbonates such as potassium carbonate and sodium bicarbonate. The solvent usable in the reaction includes ethers such as tetrahydrofuran and dioxane; aprotic polar solvents such as dimethylformamide and dimethyl sulfoxide; aromatic hydrocarbons such as benzene and toluene; alcohols such as butanol and ethanol; and aliphatic hydrocarbons such as hexane.

To describe the step 3 in more detail, an objective compound (XIX) can be prepared by adding 1 to 5 times (by equivalent) as much a base to a solution of a compound represented by the formula (XVIII), stirring the obtained mixture at a temperature of 0° C. to a reflux temperature for about 1 to 3 hours, dropping the obtained reaction mixture into a solution of a compound represented by the formula (XXI) over a period of about 1 to 3 hours, stirring the obtained mixture at room temperature to a reflux temperature for about 1 to 3 hours to conduct a reaction, adding 1 to 20 times (by equivalent) as much ammonium formate or ammonium acetate, 1 to 20 times (by equivalent) as much formic or acetaic acid and 1 to 20 times (by equivalent) as much formamide to the resulting mixture, and heating the obtained mixture at 50° to 200° C. for about 1 to 10 hours.

The thus-prepared compound (XIX) is reduced in the step 4 according to a conventional process into a compound represented by the general formula (XX), which is further converted into a carbamoyl compound (XV) by reacting it with a lower alkyl isocyanate such as butyl isocyanate according to a conventional process. Thus an objective compound (XV) can be obtained.

Experimental Example will now be given to illustrate the effect of the compounds of the present invention in more detail.

EXPERIMENTAL EXAMPLE

1. Experimental Method

<In-Vitro Test>

Representative compounds according to the present invention were examined for ACAT-inhibitory activity according to the in-vitro test proposed in Journal of Lipid Research, vol. 24, 1049 to 1059 (1983) by F. J. Field and S. N. Mathur.

The inhibitory activity of a test compound against esterification or acylation of cholesterol with oleoyl CoA or acyl-CoA was evaluated by using the microsome of the small intestine of a rabbit as an enzyme source and determining the amount of a radioisotope-labeled cholesterol oleate made from a radioisotope-labeled oleoyl-CoA and (free) cholesterol.

The results are given in Table 1 by IC 50 value, i.e., the concentration of a test compound which inhibited 50% of the ACAT activity.

<In-Vivo Test>

A male Sprague-Dawley rat was made to get hypercholesterolemia by feeding with food containing 1% of cholesterol for 2 days. A compound of the present invention (compound of Example 1, 54, 17 or 64) was orally administered to the rat once a day in a dose of 10 mg per kg of the weight. The serum cholesterol level was effectively lowered.

2. Experimental Results

The results are given in Tables 1 and 2.

TABLE 1

| Ex. No. | Structure formula | ACAT-inhibitory activity IC50 (μM) |
|---|---|---|
| 1 | (structure: NMe2, NHCONH-pentyl, O-propyl-N=CH-N=C(Me)-phenyl) | 0.043 |
| 54 | (structure: Me, NHCONH-butyl, O-propyl-N=CH-N=CH-phenyl) | 0.048 |
| 17 | (structure: NMe2, NHCONH-hexyl, O-propyl-N=CH-N=CH-phenyl) | 0.031 |
| 64 | (structure: NMe2, NHCONH-pentyl, O-propyl-N-piperazine-N-phenyl) | 0.017 |

TABLE 2

| Ex. No. | Structure formula | ACAT-inhibitory activity IC50 (μM) |
|---|---|---|
| 80 | (structure: Me, NHCONH-butyl, O-propyl-N=CH-N=C(iPr)-phenyl) | 0.088 |
| 81 | (structure: Me, NHCONH-pentyl, O-propyl-N=CH-N=C(Et)-phenyl) | 0.13 |
| 93 | (structure: Me, NHCONH-pentyl, O-propyl-N=CH-N=C(Cl)-phenyl) | 0.049 |
| 127 | (structure: Me, NHCONH-pentyl, O-propyl-N=CH-N=C(Me)-phenyl) | 0.10 |

It can be understood from the above results that the compounds of the present invention exhibit a potent inhibitory activity against the ACAT.

Accordingly, the compounds of the present invention are useful as various anti-arteriosclerotic agents. Particularly, they are effective in the treatment and prevention of diseases caused by arteriosclerosis, for example, cerebrovascular diseases such as cerebral apoplexy and cardiac infarction.

One week toxic study of the obtained compound in Example 81 was performed in Sprague-Dawley rats weighing 250–300 g. The compound was orally given to animals at daily does of 100 mg/kg for one week. There was no adverse effects in body weight, blood chemical analysis, food consumption, hematological examination, organ weight, clinical observation, autopsy, induction of drug metabolizing enzyme and microscopic examination. No toxicological sympton was observed during the administration. In this experimental condition, it turns out the compound of Example 81 is no toxic substance.

Similarly, the compounds of Example 1, 2, 5, 80 and 127 were no toxic substances in the same condition.

Similarly, it was made clear or clarified by conducting the same toxicological experiment that the obtained compounds in Example 1, 2, 5, 17, 80 and 127 were no toxic substances.

When the compound of the present invention is administered as an anti-arteriosclerotic or anti-atherosclerotic agent, it may be orally administered in the form of powder, granule, capsule or syrup or may be parenterally administered as suppository, injection, external preparation or drop. The dose per adult a day is generally about 0.1 to 5,000 mg, preferably 2 to 1,000 mg, which is administered at once or in several portions, though the dosage remarkably varies depending upon the symptom and the age.

The pharmaceutical preparation according to the present invention is prepared by using a conventional carrier according to a conventional process.

That is, a solid preparation for oral administration according to the present invention is prepared by adding a filler and, if necessary, a binder a disintegrator, a lubricant, a coloring agent and/or a corrective to a principal agent and shaping the obtained mixture into tablet, coated tablet, granule, powder or capsule.

The filler includes lactose, corn starch, sucrose, sorbitol, crystalline cellulose and silicon dioxide; the binder includes polyvinyl alcohol, polyvinyl ether, ethylcellulose, methylcellulose, acacia, tragacanth, gelatin, shellac, hydroxypropylcellulose, hydroxypropylmethylcellulose, calcium citrate, dextrin and pectin; the lubricant includes magnesium stearate, talc, polyethylene glycol, silica and hardened vegetable oils; the coloring agent includes those permitted to be added to drugs; and the corrective includes powdered cocoa, menthol, aromatic powder, mentha oil, borneol and powdered cinnamon bark. The tablet and granule according to the present invention may be, of course, coated with sugar, gelatin or the like at need.

An injection according to the present invention is prepared by adding a pH modifier, a buffer, a stabilizer and/or a solubilizing agent to a principal agent at need and formulating the obtained mixture into a subcutaneous, intramuscular or intravenous injection according to a conventional process.

Examples of the present invention will now be described, though it is needless to say that the present invention is not limited to them.

In the structural formulas which will be given below, Me stands for a methyl group.

Example 1

N-[6-N,N-Dimethylamino-2-{3-(5-methyl-4-phenyl-1H-imidazol-1-yl)propoxy}]phenyl-N'-pentylurea

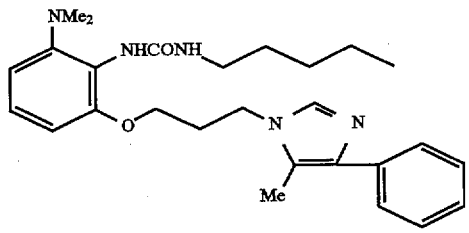

A solution of 8.85 g of 3-(5-methyl-4-phenyl-1H-imidazol-1-yl)propyl chloride in dimethylformamide was dropped into a dimethylformamide suspension containing 10 g of 3-dimethylamino-2-(N'-pentylureido) phenol, 10.4 g of potassium carbonate and a catalytic amount of sodium iodide. The obtained mixture was stirred at 60° C. for 2 hours to conduct a reaction. After the completion of the reaction, the reaction mixture was extracted with ethyl acetate. The ethyl acetate layer was washed with a saturated aqueous solution of common salt, dried over magnesium sulfate and distilled to remove the solvent. The residue was crystallized from a benzene/hexane mixture and recrystallized from ethyl acetate to give 12.03 g of the title compound as a white crystal (yield: 69%).

m.p. (°C.): 128 to 130

$^1$H-NMR (90 MHz, CDCl$_3$) δ ppm=0.90 (3H, t, J=6), 1.16~1.71 (6H, m), 2.21 (2H, quintet, J=5), 2.28 (3H, s), 2.78 (6H, s), 3.19 (2H, q, J=5), 4.13 (2H, t, J=6), 6.19 (1H, brs), 6.70 (1H, brt), 6.40~7.60 (9H, m)

M/Z (M+H)$^+$: 464

The compounds which will be described in the following Examples 2 to 36 were prepared in a similar manner to that of Example 1.

Chemical structural formula, yield (%), melting point (°C.), mass spectrometry data (M+H)$^+$ and $^1$H-NMR (δ ppm, JHz) will now be given with respect to each of the compounds.

Example 2

N-[6-N,N-Dimethylamino-2-{3-(4-phenyl-1H-imidazol-1-yl)propoxy}]phenyl-N'-butylurea

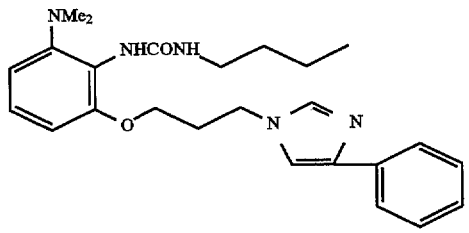

yield (%): 36 m.p. (°C.): 98 to 100

M/Z (M+H)$^+$: 436

$^1$H-NMR (90 MHz, CDCl$_3$) δ ppm=0.90 (3H, t, J=6.0), 1.30~1.68 (4H, m), 2.21 (2H, quintet, J=5.5), 2.73 (6H, s), 3.21 (2H, q, J=6.0), 3.91 (2H, q, J=5.5), 4.19 (2H, q, J=5.5), 6.39 (1H, brs), 6.70 (1H, brt), 6.41~7.80 (10H, m)

Example 3

N-[6-N,N-Dimethylamino-2-{3-(5-methyl-4-phenyl-1H-imidazol- 1-yl)propoxy}]phenyl-N'-butylurea

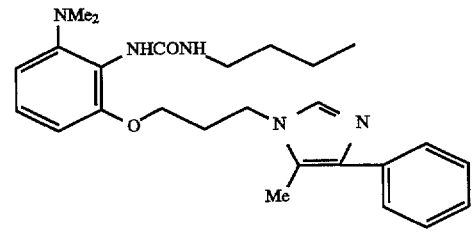

yield (%): 55 m.p. (°C.): 123 to 125

M/Z (M+H)$^+$: 450

$^1$H-NMR (400 MHz, CDCl$_3$) δ ppm=0.90 (3H, t, J=6.0), 1.37 (2H, sextet, J=6.0), 1.48 (2H, quintet, J=6.0), 2.22 (2H, quintet, J=5.0), 2.38 (3H, s), 2.80 (6H, s), 3.23 (2H, q, J=6.5), 3.98 (2H, t, J=5.0), 4.18 (2H, t, J=5.0), 6.21 (1H, brs), 6.57~7.65 (10H, m)

Example 4

N-[6-N,N-Dimethylamino-2-[3-{4-(4-methoxyphenyl)-1H-imidazol-1-yl}propoxy]]phenyl-N'-butylurea

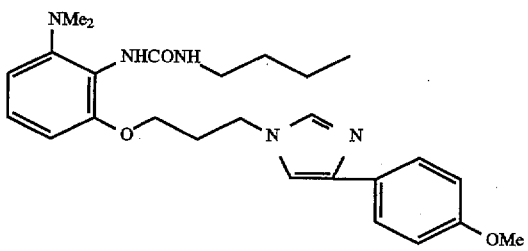

yield (%): 34
m.p. (°C.): oily substance
M/Z (M+N)+: 466
1H-NMR (90 MHz, CDCl3) δ ppm=0.90 (3H, t, J=6.0), 1.32~1.65 (4H, m), 2.24 (2H, quintet, J=5.0), 2.78 (6H, s), 3.21 (2H, q, J=6.0), 3.80 (3H, s), 3.92 (2H, t, J=5.0), 4.20 (2H, t, J=5.0), 6.29 (1H, brs), 6.50~7.70 (10H, m)

Example 5

N-[6-N,N-Dimethylamino-2-{3-(4-phenyl-1H-imidazol-1-yl)propoxy}]phenyl-N'-pentylurea

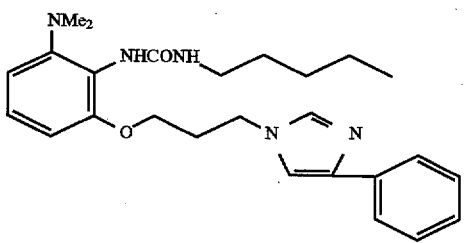

yield (%): 51
m.p. (°C.): 110 to 111
M/Z (M+H)+: 450
1H-NMR (90 MHz, CDCl3) δ ppm=0.88 (3H, t, J=7.2), 1.18~1.70 (6H, m), 2.26 (2H, quintet, J=6.5), 2.79 (6H, s), 3.21 (2H, q, J=6.5), 3.92 (2H, t, J=6.5), 4.20 (2H, t, J=6.5), 6.22 (1H, brs), 6.43~7.79 (11H, m)

Example 6

N-[2-{3-(4-Phenyl-1H-imidazol-1-yl)butoxyl-6-N,N-dimethylaminolphenyl-N'-pentylurea

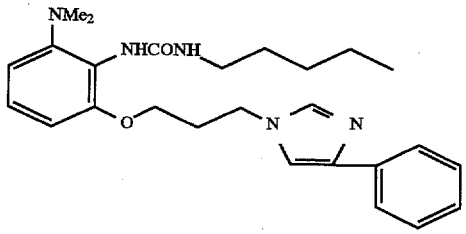

yield (%): 51
m.p. (°C.): 142 to 144

M/Z (M+H)+: 464

1H-NMR (90 MHz, CDCl3) δ ppm=0.87 (3H, t, J=6.5), 1.11~1.58 (6H, m), 1.65~2.16 (4H, m), 2.77 (6H, s), 3.17 (2H, q, J=6.5), 3.94 (2H, t, J=6.5), 4.00 (2H, t, J=6.5), 6.22 (1H, brs), 6.44~7.81 (11H, m)

Example 7

N-[6-N,N-Dimethylamino-2-{3-(4-phenyl-1H-imidazol-1-yl)ethoxy}]phenyl-N'-pentylurea

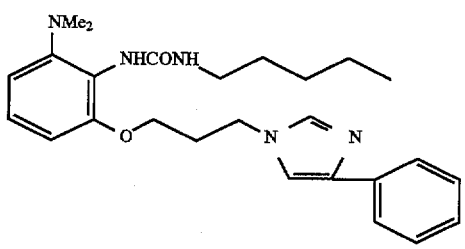

yield (%): 48 m.p. (°C.): 138 to 140

M/Z (M+H)+: 436

1H-NMR (90 MHz, CDCl3) δ ppm=0.87 (3H, t, J=6.5), 1.08~1.64 (6H, m), 2.74 (6H, s), 3.18 (2H, q, J=6.5), 4.20 (2H, t, J=6.5), 4.27 (2H, t, J=6.5), 6.16 (1H, brs), 6.38~7.88 (1H, m)

Example 8

N-[6-N,N-Dimethylamino-2-{3-(4-phenyl-1H-1,2,3-triazol-1-yl)propoxy}]phenyl-N'-pentylurea

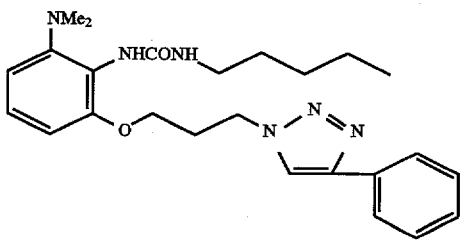

yield (%): 49 m.p. (°C.): 129 to 131

M/Z (M+H)+: 451

1H-NMR (90 MHz, CDCl3) δ ppm=0.89 (3H, t, J=6.0), 1.15~1.58 (6H, m), 2.49 (2H, quintet, J=5.0), 2.79 (6H, s), 3.20 (2H, q, J=6.0), 4.00 (2H, t, J=5.0), 4.71 (2H, t, J=5.0), 6.31 (1H, brs), 6.42~7.81 (10H, m)

Example 9

N-[6-N,N-Dimethylamino-2-{3-(4-methyl-5-phenyl-1H-imidazol-1-yl)propoxy}]phenyl-N'-pentylurea

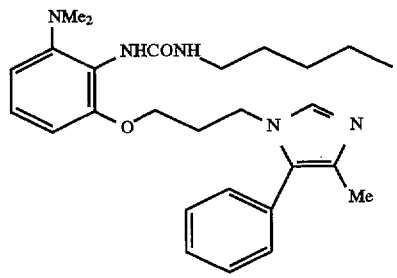

yield (%): 45 m.p. (°C.): 119 to 121

M/Z (M+H)⁺: 464

¹H-NMR (400 MHz, CDCl₃) δ ppm=0.87 (3H, t, J=7.2), 1.14~1.73 (6H, m), 1.91 (2H, quintet, J=7.2), 2.18 (3H, s), 2.78 (6H, s), 3.19 (2H, q, J=7.2), 3.76 (2H, t, J=7.2), 4.16 (2H, t, J=7.2), 6.02 (1H, brs), 6.42~7.46 (11H, m)

Example 10

N-[6-N,N-Dimethylamino-2-[3-{2-methyl-4-(4-methoxyphenyl)-1H-imidazol-1-yl}propoxy]]phenyl-N'-pentylurea

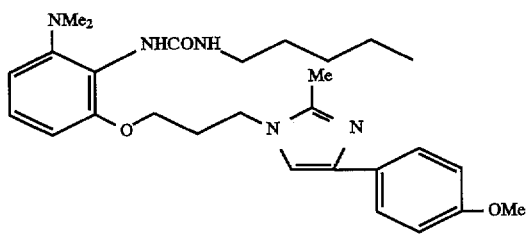

yield (%): 53 m.p. (°C.): 140 to 143

M/Z (M+H)⁺: 494

¹H-NMR (90 MHz, CDCl₃) δ ppm=0.90 (3H, t, J=6.0), 1.10~1.72 (6H, m), 2.23 (2H, quintet, J=5.0), 2.37 (3H, s), 2.79 (6H, s), 3.19 (2H, q, J=6.0), 3.78 (3H, s), 3.91 (2H, t, J=5.0), 4.11 (2H, t, J=5.0), 6.19 (1H, brs), 6.43~7.62 (9H, m)

Example 11

N-[6-N,N-Dimethylamino-2-{3-(5-phenyl-2H-tetrazol-2-yl)propoxy}]phenyl-N'-pentylurea

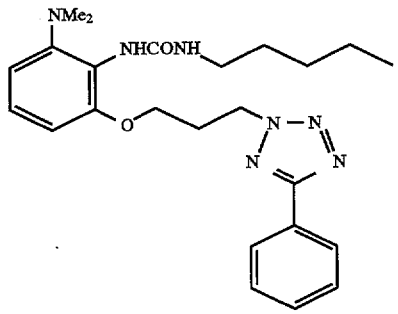

yield (%): 55 m.p. (°C.): 146 to 147

M/Z (M+H)⁺: 452

¹H-NMR (90 MHz, CDCl₃) δ ppm=0.90 (3H, t, J=6.5), 1.09~1.68 (6H, m), 2.57 (2H, quintet, J=5.0), 2.78 (6H, s), 3.19 (2H, q, J=6.0), 4.01 (2H, t, J=5.0), 4.90 (2H, t, J=5.0), 6.27 (1H, brs), 7.46~8.15 (9H, m)

Example 12

N-[6-N,N-Dimethylamino-2-{3-(2-phenyl-1H-imidazol-1-yl)propoxy}]phenyl-N'-pentylurea

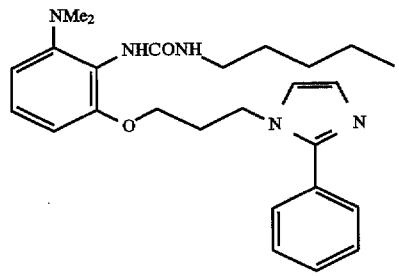

yield (%): 31 m.p. (°C.): 125 to 126

M/Z (M+H)⁺: 450

¹H-NMR (90 MHz, CDCl₃) δ ppm=0.91 (3H, t, J=6.0), 1.18~1.70 (6H, m), 2.13 (2H, quintet, J=6.5), 2.79 (6H, s), 3.16 (1H, q, J=7.0), 3.80 (2H, t, J=6.5), 4.31 (2H, t, J=6.5), 6.00 (1H, brs), 6.38~7.6 (11H, m)

Example 13

N-[6-N,N-Dimethylamino-2-[3-{4-(2-naphthyl)-1H-imidazol-1-yl}propoxy]]phenyl-N'-pentylurea

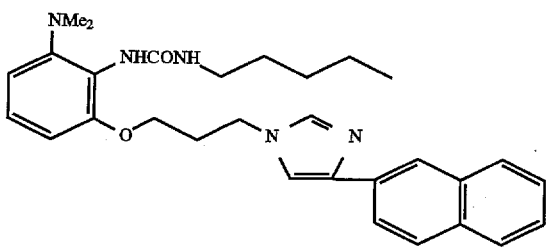

yield (%): 33 m.p. (°C.): 71 to 75

M/Z (M+H)⁺: 500

$^1$H-NMR (90 MHz, CDCl$_3$) δ ppm=0.88 (3H, t, J=6.0), 1.10~1.61 (6H, m), 2.32 (2H, quintet, J=6.5), 2.76 (6H, s), 3.19 (2H, q, J=6.5), 3.92 (2H, t, J=6.5), 4.27 (2H, t, J=6.5), 6.38~8.17 (14H, m)

Example 14

N-[6-N,N-Dimethylamino-2-[3-{4-(4-butylphenyl)-1H-imidazol-1-yl}propoxy]]phenyl-N'-pentylurea

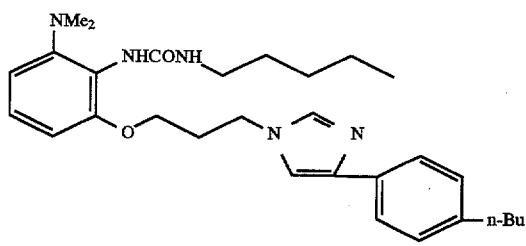

yield (%): 22 m.p. (°C.): 112 to 114

M/Z (M+H)⁺: 506

$^1$H-NMR (90 MHz, CDCl$_3$) δ ppm=0.87 (3H, t, J=6.0), 0.89 (3H, t, J=6.0), 1.03~1.72 (10H, m), 2.24 (2H, quintet, J=6.5), 2.50 (2H, q, J=6.5), 2.75 (6H, s), 3.18 (2H, q, J=6.5), 3.89 (2H, t, J=6.5), 4.21 (2H, t, J=6.5), 6.35~7.63 (11H, m)

Example 15

N-[6-N,N-Dimethylamino-2-{3-(4-phenyl-1H-imidazol-1-yl)propoxy}]phenyl-N'-ethylurea

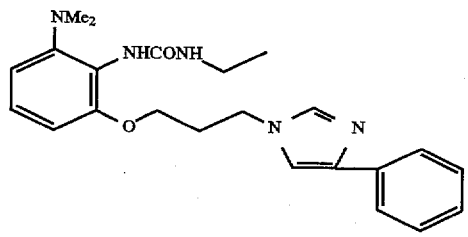

yield (%): 53 m.p. (°C.): 115 to 116

M/Z (M+H)⁺: 408

$^1$H-NMR (90 MHz, CDCl$_3$) δ ppm=1.12 (3H, t, J=7.2), 2.24 (2H, quintet, J=6.5), 2.77 (6H, s), 3.27 (2H, q, d, J=7.2, 1.5), 3.88 (2H, t, J=6.5), 4.19 (2H, t, J=6.5), 6.22 (1H, brs), 6.41~7.77 (11H, m)

Example 16

N-[6-N,N-Dimethylamino-2-{3-(4-phenyl-1H-imidazol-1-yl)propoxy}]phenyl-N'-propylurea

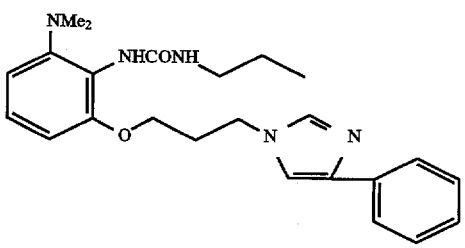

yield (%): 51 m.p. (°C.): 121 to 123

M/Z (M+H)⁺: 422

$^1$H-NMR (90 MHz, CDCl$_3$) δ ppm=0.91 (3H, t, J=7.2), 1.48 (2H, sextet, J=7.2), 2.25 (2H, quintet, J=6.5), 2.78 (6H, s), 3.18 (2H, q, J=6.5), 3.91 (2H, t, J=6.5), 4.21 (2H, t, J=6.5), 6.22 (1H, brs), 6.41~7.79 (11H, m)

Example 17

N-[6-N,N-Dimethylamino-2-{3-(4-phenyl-1H-imidazol-1-yl)propoxy}]phenyl-N'-hexylurea

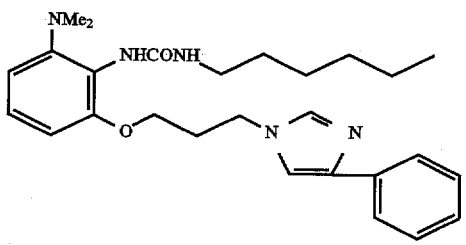

yield (%): 48 m.p. (°C.): 124 to 126

M/Z (M+H)⁺: 464

$^1$H-NMR (90 MHz, CDCl$_3$) δ ppm=0.89(3H, t, J=7.2), 1.08~1.68 (8H, m), 2.26 (2H, quintet, J=6.5), 2.79 (6H, s), 3.22 (2H, q, J=6.5), 3.93 (2H, t, J=6.5), 4.21 (2H, t, J=6.5), 6.20 (1H, brs), 6.42~7.78 (11H, m)

Example 18

N-[6-N,N-Dimethylamino-2-{3-(4-phenyl-1H-imidazol-1-yl)propoxy}]phenyl-N'-cyclohexylurea

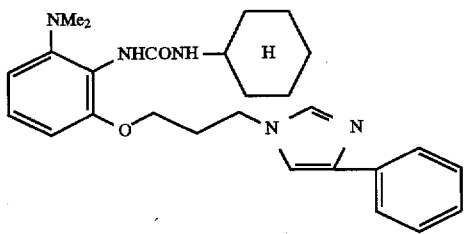

yield (%): 40
m.p. (°C.): 129 to 131
M/Z (M+H)$^+$: 462

$^1$H-NMR (90 MHz, CDCl$_3$) δ ppm=0.91~2.10 (10H, m), 2.28 (2H, quintet, J=6.5), 2.78 (6H, s), 3.50 (1H, m), 3.93 (2H, t, J=6.5), 4.21 (2H, t, J=6.5), 6.22 (1H, brs), 6.42~7.76 (11H, m)

Example 19

N-[6-N,N-Dimethylamino-2-{3-(4-phenyl-1H-imidazol-1-yl)propoxy}]phenyl-N'-cyclopentylurea

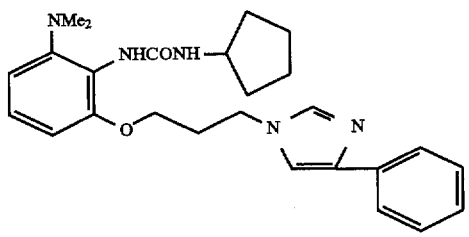

yield (%): 55
m.p. (°C.): 112 to 113
M/Z (M+H)$^+$: 448

$^1$H-NMR (90 MHz, CDCl$_3$) δ ppm=1.20~1.85 (8H, m), 2.28 (2H, quintet, J=6.5), 2.79 (6H, s), 3.93 (2H, t, J=6.5), 4.06 (1H, m), 4.22 (2H, t, J=6.5), 6.25 (1H, brs), 6.48~7.78 (11H, m)

Example 20

N-[6-N,N-Dimethylamino-2-{3-(4-phenyl-1H-imidazol-1-yl)propoxy}]phenyl-N'-3-methyl-2-butenylurea

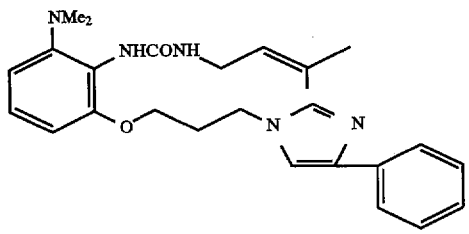

yield (%): 45
m.p. (°C.): 87 to 89

M/Z (M+H)$^+$: 448

$^1$H-NMR (90 MHz, CDCl$_3$) δ ppm=1.64 (3H, s), 1.71 (3H, s), 2.24 (2H, quintet, J=6.5), 2.76 (6H, s), 3.36 (1H, dd, J=12.6, 6.8), 3.80 (1H, dd, J=12.6, 6.5), 3.91 (2H, t, J=6.5), 4.21 (2H, t, J=6.5), 4.68 (1H, dd, J=6.8, 6.5), 5.17 (1H, brt), 6.21~7.78 (11H, m)

Example 21

N-[6-N,N-Dimethylamino-2-{3-(4-phenyl-1H-imidazol-1-yl)propoxy}]phenyl-N'-1,1-dimethylethylurea

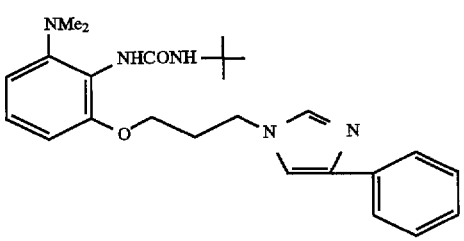

yield (%): 51 m.p. (°C.): 127 to 128

M/Z (M+H)$^+$: 436

$^1$H-NMR (90 MHz, CDCl$_3$) δ ppm=1.36 (9H, s), 2.28 (2H, quintet, J=6.5), 2.78 (6H, s), 3.91 (2H, t, J=6.5), 4.25 (2H, t, J=6.5), 6.14 (1H, brs), 6.43~7.76 (11H, m)

Example 22

N-[6-N,N-Dimethylamino-2-{3-(4-phenyl-1H-imidazol-1-yl)propoxy}]phenylhexanoylamide

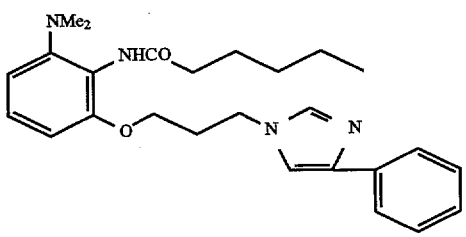

yield (%): 34 m.p. (°C.): oily substance

M/Z (M+H)$^+$: 435

$^1$H-NMR (90 MHz, CDCl$_3$) δ ppm=0.91 (3H, t, J=6.0), 1.08~1.90 (6H, m), 2.36 (2H, quintet, J=6.5), 2.70 (6H, s), 3.92 (2H, t, J=6.5), 4.21 (2H, t, J=6.5), 6.43~7.81 (11H, m)

Example 23

N-[6-N,N-Dimethylamino-2-{3-(4-phenyl-1H-imidazol-1-yl)propoxy}]phenyl-N'-methyl-N'-pentylurea

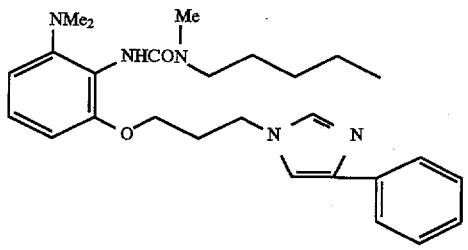

yield (%): 19 m.p. (°C.): 90 to 92

M/Z (M+H)$^+$: 464

$^1$H-NMR (400 MHz, CDCl$_3$) δ ppm=0.89 (3H, t, J=6.8), 1.12~1.80 (6H, m), 2.19 (2H, quintet, J=5.6), 2.66 (6H, s), 3.07 (3H, s), 3.41 (2H, q, J=7.2), 3.97 (2H, t, J=5.6), 4.25 (2H, t, J=5.6), 6.11 (1H, s), 6.59~7.76 (10H, m)

Example 24

N-[6-Butyl-2-[3-{4-(4-methoxyphenyl)-1H-imidazol-1-yl}propoxy]]phenyl-N'-butylurea

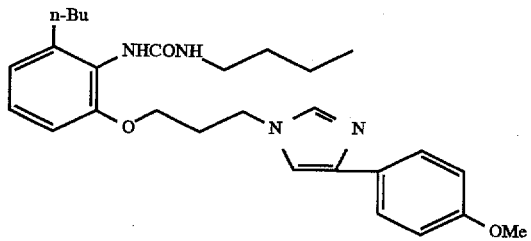

yield (%): 90 m.p. (°C.): 104 to 105

M/Z (M+H)$^+$: 479

$^1$H-NMR (90 MHz, CDCl$_3$) δ ppm=0.88 (3H, t, J=6.0), 0.91 (3H, t, J=6.0), 1.10~1.70 (8H, m), 2.17 (2H, quintet, J=6.5), 2.63 (2H, dd, J=7.2, 6.5), 3.18 (2H, q, J=6.5), 3.79 (3H, s), 3.90 (2H, t, J=6.5), 4.13 (2H, t, J=6.5), 4.72 (1H, brt), 6.00 (1H, brs), 6.60~7.73 (9H, m)

Example 25

N-[6-(2-Pyrrolidon-1-yl)-2-[3-{4-(4-methoxyphenyl)-1H-imidazol-1-yl}propoxy]]phenyl-N'-butylurea

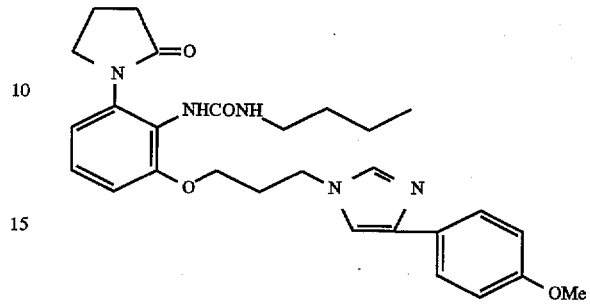

yield (%): 20 m.p. (°C.): 62 to 65

M/Z (M+H)$^+$: 506

$^1$H-NMR (90 MHz, CDCl$_3$) δ ppm=0.87 (3H, t, J=6.0), 1.18~1.32 (4H, m), 2.15 (2H, quintet, J=6.5), 2.24 (2H, m), 2.51 (2H, t, J=7.2), 3.12 (2H, q, J=6.5), 3.79 (2H, t, J=5.0), 3.80 (3H, s), 3.81 (2H, t, J=6.5), 4.08 (2H, t, J=6.5), 4.80 (1H, brs), 5.52 (1H, brt), 6.65~7.81 (9H, m)

Example 26

N-[6-N,N-Dimethylamino-3-{3-(5-methyl-4-phenyl-1H-imidazol-1-yl)propoxy}]phenyl-N'-pentylurea

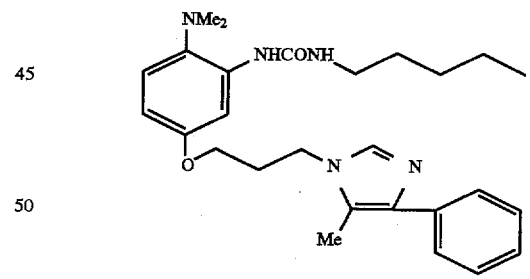

yield (%): 6 m.p. (°C.): 142 to 144

M/Z (M+H)$^+$: 464

$^1$H-NMR (400 MHz, CDCl$_3$) δ ppm=0.89 (3H, t, J=5.1), 1.23~1.78 (6H, m), 2.17 (2H, quintet, J=6.1), 2.40 (3H, s), 2.52 (6H, s), 3.22 (2H, q, J=6.8), 3.97 (2H, t, J=6.1), 4.13 (2H, t, J=6.1), 5.18 (1H, brs), 6.42~7.96 (10H, m)

Example 27

N-[6-N,N-Dimethylamino-4-{3-(5-methyl-4-phenyl-1H-imidazol-1-yl)propoxy}]phenyl-N'-pentylurea

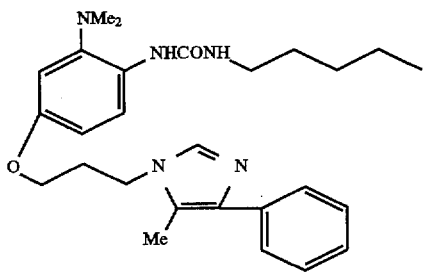

yield (%): 22 m.p. (°C.) 125 to 126

M/Z (M+H)⁺: 464

¹H-NMR (400 MHz, CDCl₃) δ ppm=0.87(3H, t, J=5.8), 1.24~1.76 (6H, m), 2.20 (2H, quintet, J=6.1), 2.40 (3H, s), 2.63 (6H, s), 3.24 (2H, q, J=6.8), 3.95 (2H, t, J=6.1), 4.18 (2H, t, J=6.1), 5.02 (1H, brs), 6.58~7.68 (10H, m)

Example 28

N-[6-N,N-Dimethylamino-5-{3-(5-methyl-4-phenyl-1H-imidazol-1-yl)propoxy}]phenyl-N'-pentylurea

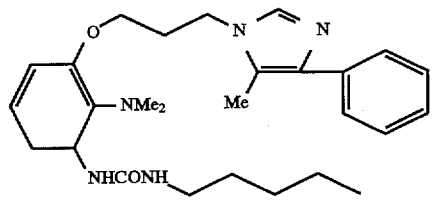

yield (%): 25 m.p. (°C.): 178 to 180

M/Z (M+H)⁺: 464

¹H-NMR (400 MHz, CDCl₃) δ ppm=0.91(3H, t, J=5.6), 1.24~1.75 (6H, m), 2.27 (2H, quintet, J=6.0), 2.42 (3H, s), 2.77 (6H, s), 3.25 (2H, q, J=6.8), 4.01 (2H, t, J=6.0), 4.17 (2H, t, J=6.0), 4.82 (1H, brt), 6.43~7.84 (9H, m), 8.27 (1H, brs)

Example 29

6-N,N-Dimethylamino-5-N'-pentylureido-4-{3-(5-methyl-4-phenyl-1H-imidazol-1-yl)propoxy}pyrimidine

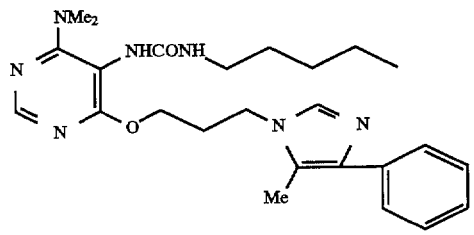

yield (%): 17 m.p. (°C.): oily substance

M/Z (M+H)⁺: 466

¹H-NMR (400 MHz, CDCl₃) δ ppm=0.87 (3H, t, J=6.2), 1.12~1.78 (6H, m), 2.19 (2H, quintet, J=6.0), 2.33 (3H, s), 3.10 (6H, s), 3.17 (2H, q, J=6.8), 3.83 (2H, t, J=6.0), 3.95 (2H, t, J=6.00, 5.58 (1H, brs), 6.65 (1H, brs), 7.21~7.71 (7H, m)

Example 30

3-N'-Butylureido-4-methyl-2-{3-(4-phenyl-1H-imidazol-1-yl)propoxy}pyridine

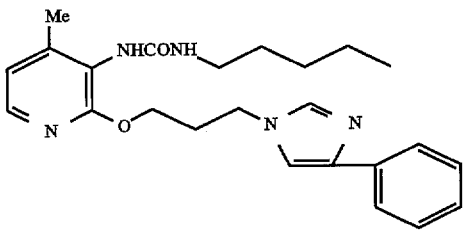

yield (%): 9 m.p. (°C.): oily substance

M/Z (M+H)⁺: 408

¹H-NMR (90 MHz, CDCl₃) δ ppm=0.88 (3H, t, J=6.5), 1.08~1.70 (4H, m), 2.21 (3H, s), 2.22 (2H, quintet, J=6.5), 3.19 (2H, q, J=6.5), 3.94 (2H, t, J=6.5), 3.99 (2H, t, J=6.5), 5.78 (1H, brt), 6.12 (1H, d, J=7.2), 6.83 (1H, d, J=7.2), 7.12~7.82 (8H, m)

Example 31

N-[6-N,N-Dimethylamino-3-methyl-2-{3-(4-phenyl-1H-imidazol-1-yl)propoxy}]phenyl-N'-pentylurea

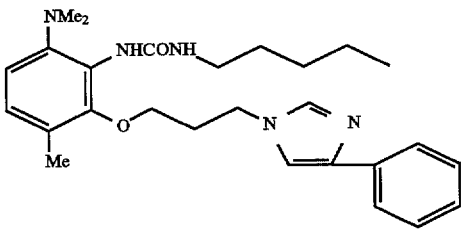

yield (%): 50 m.p. (°C.): 119 to 121

M/Z (M+H)⁺: 464

¹H-NMR (90 MHz, CDCl₃) δ ppm=0.90 (3H, t, J=6.5), 1.08~1.72 (6H, m), 2.22 (3H, s), 2.24 (2H, quintet, J=6.5), 2.70 (6H, s), 3.21 (2H, q, J=7.0), 3.84 (2H, t, J=6.5), 4.25 (2H, t, J=6.5), 6.21 (1H, brs), 6.65~7.82 (10H, m)

Example 32

N-[3,5-Dibromo-6-N,N-dimethylamino-2-[3-{4-(4-methoxyphenyl)-1H-imidazol-1-yl}propoxy]]phenyl-N'-pentylurea

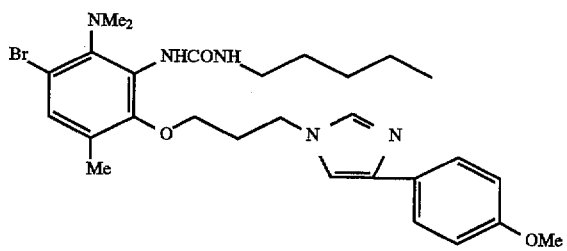

yield (%): 65 m.p. (°C.) 124 to 126

M/Z (M+H)⁺: 638

$^1$H-NMR (90 MHz, CDCl$_3$) δ ppm=0.90 (3H, t, J=6.0), 1.10~1.81 (6H, m), 2.23 (2H, quintet, J=6.5), 2.81 (6H, s), 3.21 (2H, q, J=7.0), 3.80 (3H, s), 3.97 (2H, t, J=6.5), 4.20 (2H, t, J=6.5), 5.33 (1H, brt), 6.61 (1H, brs), 6.88 (2H, d, J=9.0), 7.12 (1H, s), 7.22 (1H, s), 7.55 (1H, s), 7.61 (2H, d, J=9.0)

Example 33

N-[6-N,N-Dimethylamino-2-{4-(5-phenyl-2H-tetrazol-2-yl)butoxy}]phenyl-N'-pentylurea

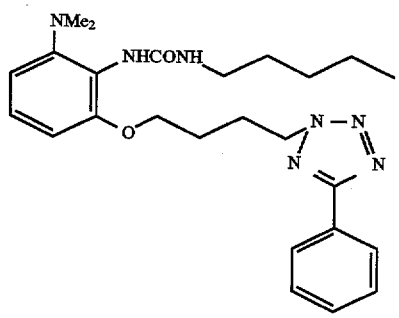

yield (%): 60 m.p. (°C.): 111 to 113

M/Z (M+H)⁺: 466

$^1$H-NMR(90 MHz, CDCl$_3$) δ ppm=0.90 (3H, t, J=6.0), 1.13~1.62 (6H, m), 1.91 (2H, quintet, J=6.5), 2.30 (2H, quintet, J=6.5), 2.79 (6H, s), 3.20 (2H, q, J=6.5), 4.03 (2H, t, J=6.5), 4.76 (2H, t, J=6.5), 6.25 (1H, brs), 6.57~8.13 (9H, m)

Example 34

N-[6-N,N-Dimethylamino-2-{6-(5-phenyl-2H-tetrazol-2-yl)hexyloxy}]phenyl-N'-pentylurea

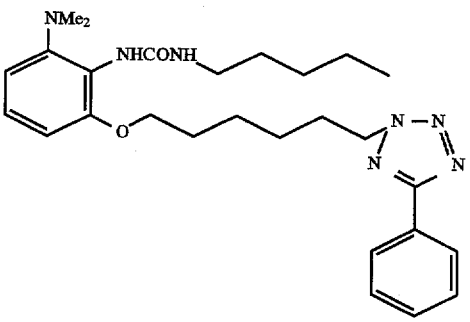

yield (%): 65 m.p. (°C.): 106 to 108

M/Z (M+H)⁺: 494

$^1$H-NMR (90 MHz, CDCl$_3$) δ ppm=0.88 (3H, t, J=6.0), 1.10~1.90 (14H, m), 2.10 (2H, quintet, J=6.5), 2.74 (6H, s), 3.17 (2H, q, J=6.5), 3.95 (2H, t, J=6.5), 4.63 (2H, t, J=6 5), 6.24 (1H, brs), 6.53~8.05 (9H, m)

Example 35

N-[6-N,N-Dimethylamino-2-[3-{4-(4-methoxyphenyl)-1H-imidazol-1-yl}propoxy]]phenyl-N'-pentylurea

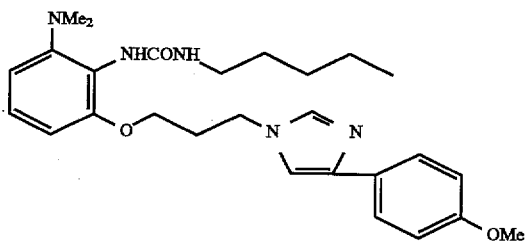

yield (%): 41 m.p. (°C.): 98 to 111

M/Z (M+H)⁺: 480

$^1$H-NMR (90 MHz, CDCl$_3$) δ ppm=0.86 (3H, t, J=6), 1.12~1.58 (6H, m), 2.25 (2H, quintet, J=6.5), 2.78 (6H, s), 3.17 (2H, q, J=6.5), 3.77 (3H, s), 3.88 (2H, t, J=6.5), 4.19 (2H, t, J=6.5), 6.30~7.68 (11H, m)

Example 36

N-[6-N,N-Diethylamino-2-{3-(4-phenyl-1H-imidazol-1-yl)propoxy}]phenyl-N'-pentylurea

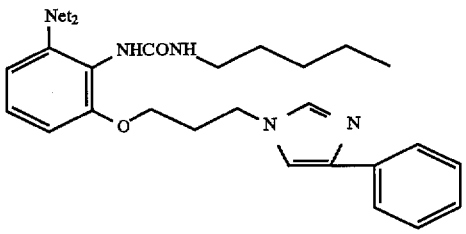

yield (%): 51
m.p. (°C.): 105 to 107
M/Z (M+H)⁺: 478

¹H-NMR (90 MHz, CDCl₃) δ ppm=0.86 (3H, t, J=7.2), 1.05 (6H, t, J=7.2), 1.00~1.71 (6H, m), 2.26 (2H, quintet, J=6.5), 3.15 (4H, q, J=7.2), 3.21 (2H, q, J=6.5), 3.92 (2H, t, J=6.5), 4.22 (2H, t, J=6.5), 6.27 (1H, brs), 6.38~7.78 (11H, m)

Example 37

N-[6-{4-(4-Phenyl-1H-imidazol-1-yl)butyl}-2-N,N-dimethylamino]phenyl-N'-butylurea

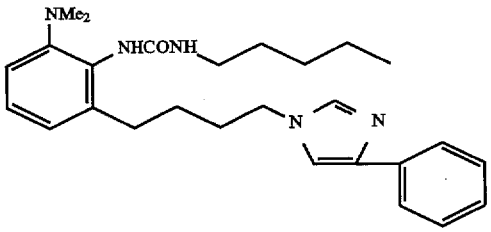

An ethanolic solution of 900 mg of sodium ethoxide was dropped into an ethanolic solution containing 6.88 g of 3-dimethylamino-2-nitrobenzyl-triphenylphosphonium bromide and 3.22 g of 3-(4-phenyl-1H-imidazol-1-yl) propionaldehyde. The obtained solution was heated under reflux for 2 hours to conduct a reaction. After the completion of the reaction, the reaction mixture was freed from the solvent by distillation and extracted With 2N NaOH. The aqueous layer was made acidic again with 1N HCl and extracted with ethyl acetate. The ethyl acetate layer was washed with a saturated aqueous solution of common salt, dried over magnesium sulfate and distilled to remove the solvent. The obtained oily substance was purified by silica gel chromatography to give 6.80 g of 2-nitro-3-[4-(4-phenyl-1H-imidazol-1-yl)butenyl]-N,N-dimethylaniline. 680 mg of 10% Pd-C was added to a solution of the product in ethyl acetate to conduct catalytic reduction in a hydrogen stream. Thus, 2-dimethylamino-6-[4-(4-phenyl-1H-imidazol- 1-yl) butyl]aniline was obtained as an oily substance. This substance was dissolved in chloroform to give a solution. 1.1 g of butyl isocyanate was dropped into the solution. The obtained mixture was heated under reflux for two hours to conduct a reaction. After the completion of the reaction, the reaction mixture was concentrated to precipitate a crystal. This crystal was recrystallized from an ethyl acetate/hexane mixture. Thus, 4.51 g of the title compound was obtained.

yield (%): 69
m.p. (°C.): 91 to 93

¹H-NMR (90 MHz, CDCl₃) δ ppm=0.89 (3H, t, J=6), 1.10~1.98 (8H, m), 2.61 (2H, t, J=6.5), 2.62 (6H, s), 3.17 (2H, q, J=7), 3.88 (2H, t, J=6.5), 5.28 (1H, brt), 6.17 (1H, brs), 6.73~7.77 (10H, m)

M/Z (M+H)⁺: 434

The compounds which will be described in the following Examples 38 to 43 were prepared in a similar manner to that of Example 37.

Chemical structural formula, yield (%), melting point (°C.), mass spectrometry data (M+H)⁺ and ¹H-NMR (δ ppm, JHz) will now be given with respect to each of the compounds.

Example 38

N-[6-{4-(4-Phenyl-1H-imidazol-1-yl)butyl}-2-N,N-dimethylaminolphenyl-N'-1-methylethylurea

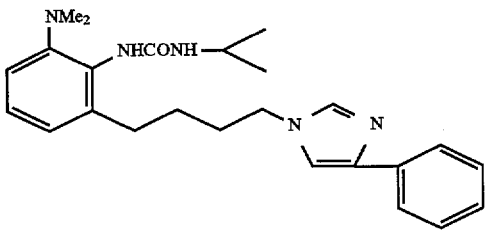

yield (%): 72
m.p. (°C.): 122 to 124
M/Z (M+H)⁺: 420

¹H-NMR (400 MHz, CDCl₃) δ ppm=1.11 (6H, d, J=6.5), 1.62 (2H, quintet, J=7.2): 1.84 (2H, quintet, J=7.2), 2.66 (2H, t, J=7.2), 2.69 (6H, s), 3.94 (2H, t, J=7.2), 4.00 (2H, q, J=7.2), 5.11 (1H, brt), 5.94 (1H, brs), 6.86~7.77 (10H, m)

Example 39

N-[6-14-(4-Phenyl-1H-imidazol-1-yl)butyl}-2-N,N-dimethylamino]phenyl-N'-cyclohexylurea

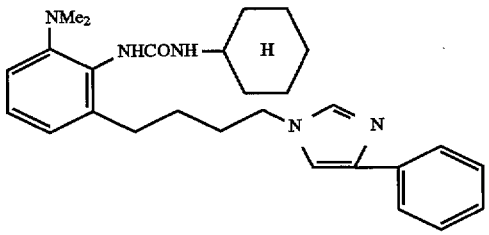

yield (%): 70
m.p. (°C.): 150 to 152
M/Z (M+H)⁺: 460

¹H-NMR (400 MHz, CDCl₃) δ ppm=1.06 (4H, m), 1.33 (2H, m), 1.60 (4H, m), 1.83 (2H, quintet, J=7.2), 1.90 (2H, m), 2.67 (2H, t, J=7.2), 2.70 (6H, s), 3.63 (1H, m), 3.93 (2H, t, J=7.2), 5.18 (1H, brt), 5.97 (1H, brs), 6.86~7.77 (10H, m)

Example 40

N-[6-{4-(4-Phenyl-1H-imidazol-1-yl)butyl}-2-N,N-dimethylamino]phenylpentanoylamide

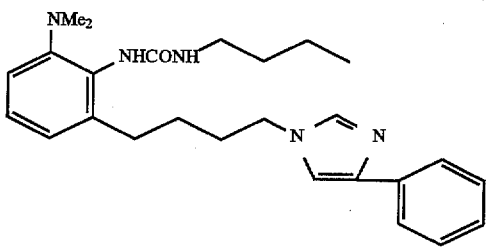

yield (%): 65
m.p. (°C.): oily substance
M/Z (M+H)⁺: 419

$^1$H-NMR (400 MHz, CDCl$_3$) δ ppm=0.95 (3H, t, J=7.0), 1.42 (2H, m), 1.58~1.79 (4H, m), 1.84 (2H, quintet, J=6.5), 2.41 (2H, t, J=6.5), 2.61 (6H, s), 2.64 (2H, t, J=6.5), 3.95 (2H, t, J=6.5), 6.90~7.76 (11H, m)

Example 41

N-[2-{4-(4-Phenyl-1H-imidazol-1-yl)butyl}-6-methyl]-phenyl-N'-butylurea

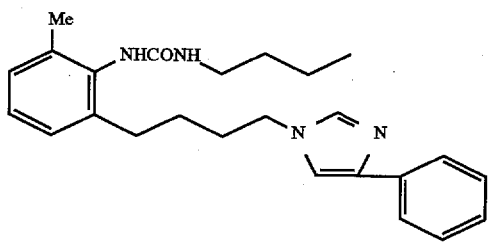

yield (%): 36
m.p. (°C.): 115 to 116
M/Z (M+H)⁺: 405

$^1$H-NMR (90 MHz, CDCl$_3$) δ ppm=0.86 (3H, t, J=6.0), 1.10~1.92 (8H, m), 2.23 (3H, s), 2.61 (2H, t, J=7.2), 3.11 (2H, q, J=7.0), 3.89 (2H, t, J=6.5), 4.48 (1H, m): 6.40 (1H, brs), 6.90~7.78 (10H, m),

Example 42

N-[6-{4-(5-Methyl-4-phenyl-1H-imidazol-1-yl)butyl}-2-N,N-dimethylamino]phenyl-N'-pentylurea

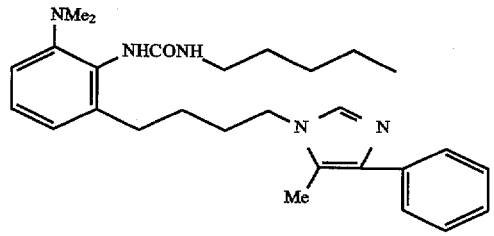

yield (%): 35
m.p. (°C.) 117 to 119
M/Z (M+H)⁺: 462

$^1$H-NMR (400 MHz, CDCl$_3$) δ ppm=0.87 (3H, t, J=6.8), 1.26 (4H, m), 1.43 (2H, quintet, J=7.2), 1.63 (2H, quintet, J=7.2), 1.79 (2H, quintet, J=7.2), 2.37 (3H, s), 2.66 (2H, t, J=7.2) 2.68 (6H, s), 3.18 (2H, q, J=6.8), 3.86 (2H, t, J=7.2), 5.24 (1H, brt), 6.00 (1H, brs), 6.86~7.65 (8H, m)

Example 43

N-[6-{4-(4-Phenyl-1H-imidazol-1-yl)butyl}-2-N,N-dimethylamino]phenyl-N'-propylurea

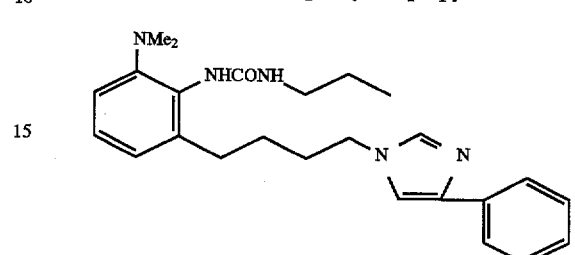

yield (%): 68
m.p. (°C.): 125 to 127
M/Z (M+H)⁺: 420

$^1$H-NMR (400 MHz, CDCl$_3$) δ ppm=0.88 (3H, t, J=7.2), 1.47 (2H, sextet, J=7.2), 1.59 (2H, quintet, J=7.2), 1.84 (2H, quintet, J=7.2), 2.67 (2H, t, J=7.2), 3.16 (2H, q, J=6.0), 3.94 (2H, t, J=7.2), 5.23 (1H, brt), 5.99 (1H, brs), 6.86~7.78 (10H, m)

Example 44

N-[2-{2-(1H-Benzimidazol-2-yl)ethyl}-6-methyl]phenyl-N'-butylurea

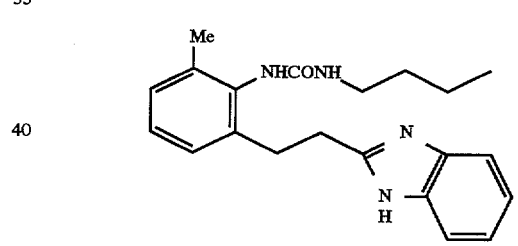

A tetrahydrofuran solution of 3.27 g of 3-methyl-2-nitrocinnamoyl chloride was dropped into a tetrahydrofuran solution of 3.41 g of o-phenylenediamine. The obtained mixture was stirred at room temperature for one hour to complete a reaction. Thereafter, the obtained solution was concentrated and extracted with ethyl acetate. The residue was heated in acetic acid at 100° C. for 2 hours to give 3.67 g of 3-[2-(1H-benzimidazol-2-yl)vinyl]-2-nitrotoluene.

This product was catalytically reduced in the presence of 10% Pd-C as a catalyst in an acetic acid/ethanol mixture to give 2.30 g of 2-[2-(1H-benzimidazol-2-yl)ethyl]-6-methylaniline. This product was dissolved in chloroform to give a solution. 1.08 g butyl isocyanate was dropped into the solution. The obtained mixture was heated under reflux for 5 hours to conduct a reaction. After the completion of the reaction, the obtained mixture was concentrated to precipitate a crystal. This crystal was recrystallized from an ethyl acetate/hexane mixture. Thus, 2.25 g of the title compound was obtained.

yield (%): 48
m.p. (°C.): 222 to 224

¹H-NMR (90 MHz, DMSO) δ ppm=0.85 (3H, t, J=6.5), 1.10~1.60 (4H, m), 2.19 (3H, s), 3.08 (4H, m), 6.02 (1H, brt), 6.93~7.55 (7H, m), 7.60 (1H, brs)

M/Z 351 (M+H)⁺

Example 45

N-[6-{4-(4-Phenyl-1H-imidazol-1-yl)-1-cis-butenyl}-2-N,N-dimethylamino]phenyl-N'-butylurea

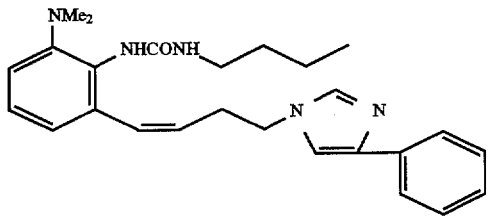

An ethanolic solution of 90 mg of sodium ethoxide was dropped into an ethanolic solution containing 650 mg of 3-dimethylamino-2-nitrobenzyltriphenylphosphonium bromide and 320 mg of 3-(4-phenyl-1H-imidazol-1-yl) propionaldehyde. The obtained solution was heated under reflux for 2 hours to conduct a reaction. After the completion of the reaction, the mixture was distilled to remove the solvent. The residue was extracted with 2N NaOH and the obtained aqueous layer was made acidic again with 1N HCl and extracted with ethyl acetate. The ethyl acetate layer was washed with a saturated aqueous solution of common salt, dried over magnesium sulfate and distilled to remove the solvent. The obtained oily substance which is a mixture of cis- and trans-isomers was purified by silica gel chromatography to give 220 mg of 3-[4-(4-phenyl-1H-imidazol-1-yl)-1-cis-butenyl]-2-nitro-N,N-dimethylaniline. 430 mg of zinc was added to a solution of this product in acetic acid to give 2-dimethylamino-6-[4-(4-phenyl-1H-imidazol-1-yl)- 1-Cis-butenyl]aniline as an oily substance. This oily substance was dissolved in chloroform, followed by the dropwise addition of 50 mg of butyl isocyanate. The obtained mixture was heated under reflux for 2 hours to conduct a reaction. After the completion of the reaction, the obtained reaction mixture was concentrated to precipitate a crystal. This crystal was recrystallized from an ethyl acetate/hexane mixture to give 190 mg of the title compound.

yield (%): 30 m.p. (°C.): 108 to 110

¹H-NMR (90 MHz, CDCl₃) δ ppm=0.88 (3H, t, J=6.0), 1.02~1.58 (4H, m), 2.59 (2H, m), 2.62 (6H, s), 3.13 (2H, q, J=6.5), 3.95 (2H, t, J=6.5), 5.17 (1H, brt), 5.76 (1H, m), 6.08 (1H, dd, J=11.2), 6.40~7.81 (11H, m)

M/Z 432 (M+H)⁺

Example 46

N-[6-Methyl-2-{3-(1H-benzimidazol-2-yl)propoxy}]-phenyl-N'-butylurea

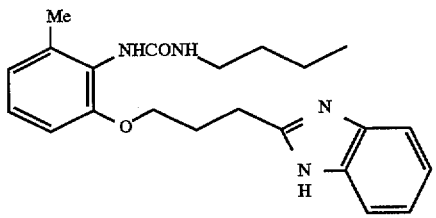

0.46 cc of thionyl chloride was added to a solution of 1 g of 4-(3-methyl-2-nitrophenoxy)butyric acid in chloroform. The obtained mixture was heated under reflux for one hour to give an acid chloride. A solution of this acid chloride in chloroform was dropped into a solution of 580 mg of o-phenylenediamine in chloroform to give 800 mg of an amide. This amide was heated in acetic acid at 100° C. to give 650 mg of 3-[3-(1H-benzimidazol-2-yl)propoxy]-2-nitrotoluene. This product was catalytically reduced according to a conventional process and condensed with butyl isocyanate to give 500 mg of the title compound.

yield (%): 31 m.p. (°C.): 138 to 140

¹H-NMR (90 MHz, CDCl₃) δ ppm=0.80 (3H, t, J=6.5), 1.00~1.61 (4H, m), 2.21 (2H, quintet, J=6.5), 2.24 (3H, s), 3.04 (2H, t, J=6.5), 3.17 (2H, q, J=6.5), 3.80 (2H, t, J=6.5), 5.00 (1H, brt), 6.36 (1H, brs), 6.48~7.55 (7H, m)

M/Z 381 (M+H)⁺

The compounds which will be described in the following Examples 47 and 48 were prepared in a similar manner to that of Example 46.

Chemical structural formula, yield (%), melting point (°C.), mass spectroscopy data (M+H)⁺ and ¹H-NMR (δ ppm, JHz) will be given with respect to each of the compounds.

Example 47

N-[6-Methyl-2-{(1H-benzimidazol-2-yl)methoxyl}] phenyl-N'-butylurea

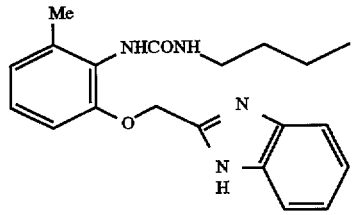

yield (%): 3 m.p. (°C.): 170 to 172

¹H-NMR (90 MHz, DMSO) δ ppm=0.85 (3H, t, J=6.0), 1.02~1.60 (4H, m), 2.20 (3H, s), 3.05 (2H, q, J=6.5), 5.36 (2H, s), 6.28 (1H, brt), 6.61~7.58 (8H, m)

M/Z 353 (M+H)⁺

Example 48

N-[6-Methyl-2-[{(1H-benzimidazol-2-yl)methoxy}-methyl]]phenyl-N'-butylurea

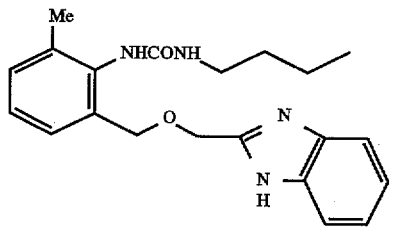

yield (%): 27 m.p. (°C.): 168 to 170

$^1$H-NMR (90 MHz, CDCl$_3$) δ ppm=0.79 (3H, t, J=6.0), 0.98~1.50 (4H, m), 2.25 (3H, s), 3.10 (2H, q, J=6.5), 5.41 (2H, s), 5.72 (2H, s), 6.10 (1H, brt), 6.80~7.61 (8H, m), 12.04 (1H, brs)

M/Z 367 (M+H)$^+$

Example 49

6-N,N-Dimethylamino-5-N'-pentylureido-4-[3-(5-methyl-4-phenyl-1H-imidazol-1-yl)propylamino] pyrimidine

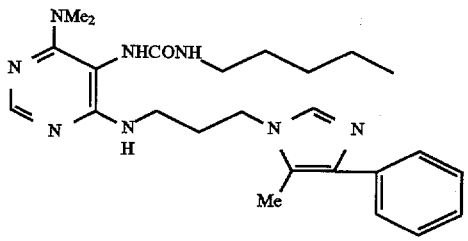

2 g of triethylamine was added to a dimethylformamide solution containing 2 g of 6-chloro-4-dimethylamino-5-nitropyrimidine and 1-(3-aminopropyl)-5-methyl-4-phenyl-1H-imidazole. The obtained mixture was heated at 100° C. for one hour to conduct a reaction. After the completion of the reaction, the reaction mixture was extracted with ethyl acetate. The ethyl acetate layer was dried over magnesium sulfate and distilled to remove the solvent. The obtained oily substance was purified by silica gel chromatography to give 2.46 g of 6-N,N-dimethylamino-5-nitro-[3-(4-phenyl-5-methyl-1H-imidazol-1-yl)propylaminolpyrimidine. This product was catalytically reduced and condensed with pentyl isocyanate according to a conventional process to give 1.70 g of the title compound.

yield (%): 35 m.p. (°C.): 151 to 153

$^1$H-NMR (400 MHz, CDCl$_3$) δ ppm=0.85 (3H, t, J=7.2), 1.18~1.43 (6H, m), 2.07 (2H, quintet, J=6.5), 2.33 (3H, s), 3.02 (6H, s), 3.14 (2H, t, d, J=6.5, 4.5), 3.50 (2H, q, J=5.6), 3.95 (2H, t, J=6.5), 4.74 (1H, brt), 5.79 (1H, brs), 6.35 (1H, m), 7.23 (1H, t, J=7.6), 7.37 (2H, t, J=7.6), 7.53 (1H, s), 7.58 (2H, d, J=7.6), 8.14 (1H, s)

M/Z 381 (M+H)$^+$

Example 50

6-N,N-Dimethylamino-5-N'-pentylureido-4-[3-(5-methyl-4-phenyl-1H-imidazol-1-yl)propylthio] pyrimidine

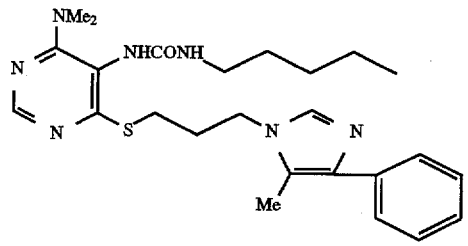

0.52 cc of triethylamine was added to a dimethylformamide solution containing 700 mg of 6-chloro-4-dimethylamino-5-nitropyrimidine and 871 mg of 5-methyl-4-phenyl-1-(3-propylthio)-1H-imidazole. The obtained mixture was heated at 50° C. for one hour to conduct a reaction. After the completion of the reaction, the reaction mixture was extracted with ethyl acetate. The ethyl acetate layer was dried over magnesium sulfate and distilled to remove the solvent. The obtained oily substance was purified by silica gel chromatography to give 480 mg of 6-N,N-dimethylamino-5-nitro-4-[3-(5-methyl-4-phenyl-1H-imidazol-1-yl)propylthio]pyrimidine. This product was catalytically reduced and condensed with 120 mg of pentyl isocyanate according to a conventional process to give 60 mg of the title compound.

yield (%): 3.3 m.p. (°C.): oily substance $^1$H-NMR (400 MHz, CDCl$_3$) δ ppm=0.89 (3H, t, J=6.8), 1.28 (4H, m), 1.52 (2H, m), 2.14 (2H, quintet, J=6.8), 2.39 (3H, s), 3.15 (6H, s), 3.25 (2H, q, J=6.8), 3.99 (2H, t, J=6.8), 7.23~7.65 (6H, m), 8.35 (1H, s)

M/Z 482 (M+H)$^+$

Example 51

N-[6-N,N-Dimethylamino-2-{3-(5-methyl-4-phenyl-1H-imidazol-1-yl)propylamino}]phenyl-N'-pentylurea A solution of 5.5 g of 3-chloro-2-nitro-1-[N-benzyl-3-(5-methyl-4-phenyl-1H-imidazol-1-yl)propylamino]benzene and 22.4 ml of a 50% aqueous solution of dimethylamine in dimethylformamide was heated at 200° C. for 6 hours to conduct a reaction. After the completion of the reaction, the reaction mixture was extracted with ethyl acetate. The ethyl acetate layer was dried over magnesium sulfate and distilled to remove the solvent. The obtained oily substance was purified by silica gel chromatography to give 2.20 g of 3-N,N-dimethylamino-2-nitro-1-[N-benzyl-3-(5-methyl-4- phenyl-1H-imidazol-1-yl)propylamino]benzene. This product was reduced with SnCl$_2$ and condensed with 250 mg of n-amyl isocyanate, followed by the elimination of the benzyl group with palladium hydroxide. Thus, 70 mg of the title compound was obtained as an oil.

yield (%): 8.3 m.p. (°C.): oily substance $^1$H-NMR (400 MHz, CDCl$_3$) δ ppm=0.87 (3H, t, J=6.5), 1.20~1.54 (6H, m), 2.10 (2H, quintet, J=7.2), 2.39 (3H, s), 2.68 (6H, s), 3.18 (2H, q, J=7.2), 3.23 (2H, t, J=7.2), 4.05 (2H, t, J=7.2), 4.78 (1H, brt), 5.00 (1H, brs), 6.16 (1H, brt), 6.39 (1H, dd, J=7.6, 1.0), 6.49 (1H, dd, J=7.6, 1.0), 7.08 (1H, t, J=7.6), 7.26 (1H, t, J=8.4), 7.40 (2H, t, J=8.4), 7.64 (2H, dd, J=8.4, 1.2)

M/Z 463 (M+H)$^+$

Example 52

N-[6-N,N-Dimethylamino-2-{3-(5-methyl-4-phenyl-1H-imidazol-1-yl)propylthio}]phenyl-N'-pentylurea

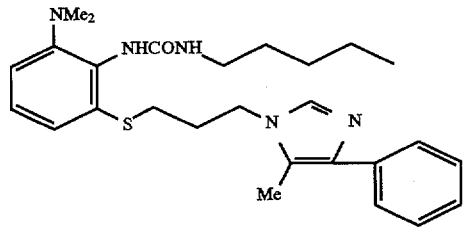

1.1 g of potassium tert-butoxide was added to a dimethylformamaide solution of 1.97 g of 3-chloro-2-nitro-N,N-dimethylaniline and 2.28 g of 5-methyl-4-phenyl-1-(3-mercapto)propyl-1H-imidazole. The obtained mixture was heated at 50° C. for one hour to conduct a reaction. After the completion of the reaction, the reaction mixture was extracted with ethyl acetate. The ethyl acetate layer was dried over magnesium sulfate and distilled to remove the solvent. The obtained oily substance was purified by silica gel chromatography to give 690 mg of 2-nitro-3-[3-(5-methyl-4-phenyl-1H-imidazol-1-yl)propylthio]-N,N-dimethylaniline. The product was catalytically reduced and condensed with 88 mg of pentyl isocyanate according to a conventional process to give 110 mg of the title compound as an oil.

yield (%): 2.3 m.p. (°C.): oily substance $^1$H-NMR (400 MHz, CDCl$_3$) δ ppm=0.89 (3H, t, J=6.4), 1.29 (4H, m), 1.48 (2H, m), 2.20 (2H, quintet, J=6.8), 2.36 (3H, s), 2.77 (6H, s), 2.86 (2H, t, J=6.8), 3.21 (2H,, q, J=6.8), 4.02 (2H, t, J=6.8), 6.34 (1H, brs), 6.47 (1H, brs), 6.97~7.64 (9H, m)

M/Z 480 (M+H)$^+$

Example 53

3-[3-(4-Phenyl-1H-imidazol-1-yl)propoxy]-2-hexylamino-N,N-dimethylaniline

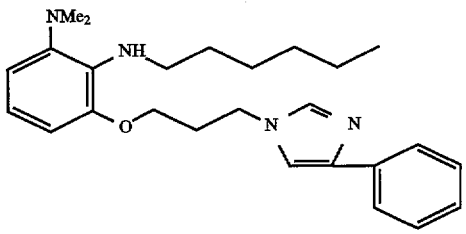

40 mg of LiAlH$_4$ was added to a tetrahydrofuran solution of 330 mg of the compound prepared in Example 22 which is an objective compound to conduct a reaction. After the completion of the reaction, the reaction mixture was treated in a conventional manner. The obtained oily substance was purified by silica gel chromatography to give 300 mg of the title compound as an oil.

yield (%): 91 m.p. (°C.): oily substance $^1$H-NMR (90 MHz, CDCl$_3$) δ ppm=0.90 (3H, t, J=6.0), 1.32 (6H, m), 2.19 (2H, quintet, J=7.0), 2.63 (6H, s), 3.30 (2H, t, J=6.5), 3.89 (2H, t, J=7.0), 4.11 (2H, t, J=7.0), 6.41~7.80 (11H, m)

M/Z 421 (M+H)$^+$

Example 54

N-[6-Methyl-2-{3-(4-phenyl-1H-imidazol-1-yl)propoxy}]-phenyl-N'-butylurea

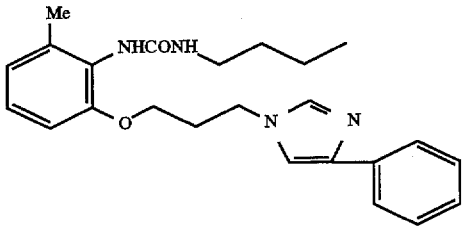

9.02 g of potassium carbonate and a catalytic amount of sodium iodide were added to a dimethylformamide solution of 5 g of 3-methyl-2-nitrophenol and 7.2 g of 4-phenyl-1-(3-chloropropyl)-1H-imidazole. The obtained mixture was heated at 100° C. for 2 hours to conduct a reaction. After the completion of the reaction, the reaction mixture was extracted with ethyl acetate. The ethyl acetate layer was dried over magnesium sulfate and distilled to remove the solvent. The obtained oily substance .was purified by silica gel chromatography to give 9.91 g of 2-nitro-3-[3-(4-phenyl-1H-imidazol-1-yl)propoxy]toluene. This product was catalytically reduced and condensed with butyl isocyanate according to a conventional process to give 11.2 g of the title compound having a melting point of 102° to 110° C.

yield (%): 84 m.p. (°C.): 102 to 110

$^1$H-NMR (90 MHz, CDCl$_3$) δ ppm=0.80 (3H, t, J=6.5), 0.99~1.58 (4H, m), 2.21 (2H, quintet, J=6.5), 2.18 (3H, s), 3.06 (2H, q, J=6.8), 3.72 (2H, t, J=6.5), 3.96 (2H, t, J=6.5), 5.43 (1H, brs), 6.39~7.75 (11H, m)

M/Z 407 (M+H)⁺

The compounds which will be described in the following Examples 55 to 62 were prepared in a similar manner to that of Example 54.

Chemical structural formula, yield (%), melting point (°C.), mass spectrometry data (M+H)⁺ and ¹H-NMR (δ ppm, JHz) will now be given with respect to each of the compounds.

Example 55

N-[6-Methyl-2-{3-(4-phenyl-1H-imidazol-1-yl) propoxy}]-phenyl-N'-methyl-N'-butylurea

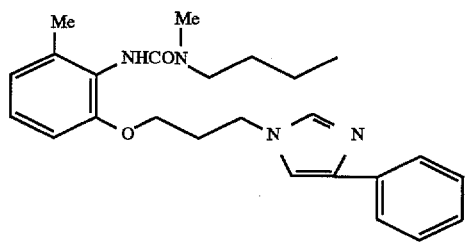

yield (%): 17 m.p. (°C.): oily substance

¹H-NMR (90 MHz, CDCl₃) δ ppm=0.93 (3H, t, J =6.0), 1.22~1.78 (4H, m), 2.22 (2H, quintet, J=6.5), 2.23 (3H, s), 3.01 (3H, s), 3.35 (2H, t, J=6.5), 3.98 (2H, t, J=6.5), 4.10 (2H, t, J=6.5), 5.81 (1H, brs), 6.58~7.78 (10H, m)

M/Z 421 (M+H)⁺

Example 56

N-[6-Methyl-2-[3-{4-(4-methoxyphenyl)-1H-imidazol-1-yl}propoxy]]phenylpentanoylamide

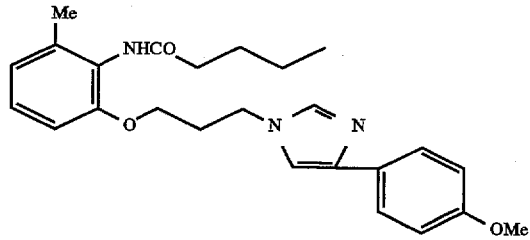

yield (%): 34 m.p. (°C.): oily substance

¹H-NMR (90 MHz, CDCl₃) δ ppm=0.90 (3H, t, J=6.0), 1.10~1.82 (4H, m), 2.09 (2H, t, J=7 2), 2.16 (3H, s), 2.22 (2H, quintet, J=6.5), 3.76 (3H, s), 3.84 (2H, t, J=6.5), 4.02 (2H, t, J=6.5), 6.46~7.83 (10H,

M/Z 422 (M+H)⁺

Example 57

N-[6-Methyl-2-[3-{4-(4-methoxyphenyl)-1H-imidazol-1-yl}propoxy]]phenyl-N'-butylurea

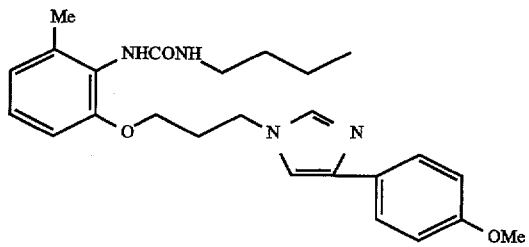

yield (%): 34 m.p. (°C.): oily substance

¹H-NMR (90 MHz, CDCl₃) δ ppm=0.86 (3H, t, J=6.0), 1.11~1.50 (4H, m), 2.13 (2H, quintet, J=6.5), 2.23 (3H, s), 3.13 (2H, q, J=6.5), 3.78 (3H, s), 3.82 (2H, t, J=6.5), 4.08 (2H, t, J=6.5), 5.01 (1H, brt), 6.24 (1H, brs), 6.53~7.70 (9H, m)

M/Z 437 (M+H)⁺

Example 58

N-[6-Methyl-2-[3-{4-(4-methoxyphenyl)-1H-imidazol-1-yl}propoxy]]phenyloctanoylamide

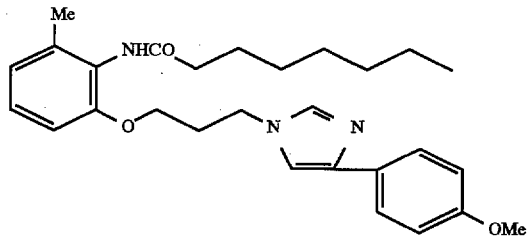

yield (%): 33 m.p. (°C.): 91 to 94

¹H-NMR (90 MHz, CDCl₃) δ ppm=0.88 (3H, t, J=6.0). 1.12~1.50 (10H, m), 2.18 (3H, s), 2.16 (2H, t, J=7.0), 2.23 (2H, quintet, J=6.5), 3.78 (3H, s), 3.96 (2H, t, J=6.5), 4.11 (2H, t, J=6.5), 6.53~7.78 (10H, m)

M/Z 464 (M+H)⁺

Example 59

N-[6-methyl-2-[3-{4-(2-trans-methoxycarbonylvinyl)-1H-imidazol-1-yl}propoxy]] phenyl-N'-butylurea

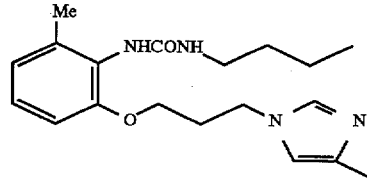

yield (%): 55 m.p. (°C.): 169 to 171

¹H-NMR (90 MHz, DMSO) δ ppm=0.88 (3H, t, J=6.5), 1.09~1.54 (4H, m), 2.16 (2H, quintet, J=6.5), 2.20 (3H, s), 3.05 (2H, q, J=6.5), 3.66 (3H, s), 3.84 (2H, t, J=6.5), 4.17 (2H, t, J=6.5), 6.20 (1H, brt), 6.30 (1H, d, J=16.5), 6.75 (1H, dd, J=7.5, 1.5), 6.76 (1H, dd, J=7.5, 1.5), 7.02 (1H, t, J=7.5), 7.16 (1H, brs), 7.52 (1H, d, J=16.5), 7.57 (1H, s), 7.67 (1H, s)

M/Z 415 (M+H)⁺

Example 60

N-[6-Methyl-2-{3-(4,5-dimethyl-1H-imidazol-1-yl)propoxy}]phenyl-N'-butylurea

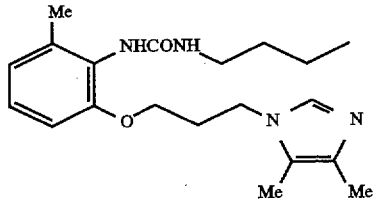

yield (%): 6 m.p. (°C.): 151 to 153

¹H-NMR (90 MHz, CDCl₃) δ ppm=0.89 (3H, t, J=7.0), 1.11~1.60 (4H, m), 2.12 (3H, s), 2.14 (3H, s), 2.22 (2H, quintet, J=6.5), 2.30 (3H, s), 3.18 (2H, q, J=6.5), 3.87 (2H, t, J=6.5) 4.02 (2H, t, J=6.5), 4.78 (1H, brt), 5.64 (1H, brs), 6.61 (1H, dd, J=7.5, 1.5), 6.80 (1H, dd, J=7.5, 1.5), 7.08 (1H, t, J=7.5), 7.30 (1H, s)

M/Z 359 (M+H)⁺

Example 61

N-[6-Methyl-2-[3-{4-(2-methoxycarbonylethyl)-1H-imidazol-1-yl}propoxy]]phenyl-N'-butylurea

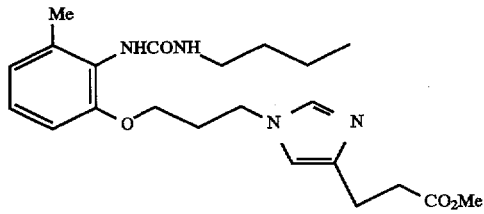

yield (%): 78 m.p. (°C.): 113 to 115

¹H-NMR (90 MHz, CDCl₃) δ ppm=0.88 (3H, t, J=7.0), 1.10~1.58 (4H, m), 2.08 (2H, quintet, J=6.5), 2.18 (3H, s), 2.40~2.72 (4H, m), 3.04 (2H, q, J=6.5), 3.56 (3H, s), 3.79 (2H, t, J=6.5), 6.18 (1H, brt), 6.60~7.02 (4H, m), 7.08 (1H, brs), 7.40 (1H, s)

M/Z 417 (M+H)⁺

Example 62

N-[6-Methyl-2-{3-(2-phenyl-1H-imidazol-1-yl)propoxy}]-phenyl-N'-butylurea

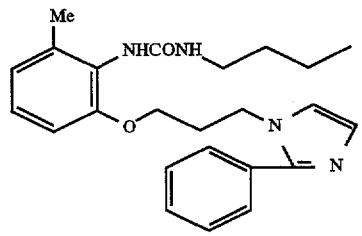

yield (%): 41 m.p. (°C.): 120 to 122

¹H-NMR (90 MHz, CDCl₃) δ ppm=0.81 (3H, t, J=6.8); 0.98~1.52 (4H, m), 1.99 (2H, quintet, J=6.5), 2.19 (3H, s), 3.03 (2H, q, J=6.8), 3.68 (2H, t, J=6.5), 4.15 (2H, t, J=6.5), 4.98 (1H, brt), 5.94 (1H, brs), 6.38~7.50 (10H, m)

M/Z 407 (M+H)⁺

Example 63

N-[6-Methyl-2-[3-{4-(4-methoxyphenyl)-1H-imidazol-1-yl}propoxy]]phenyl-(2-butylamino)acetamide

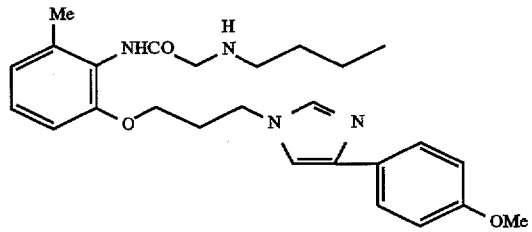

5.4 g of potassium carbonate and a catalytic amount of NaI were added to a solution of 3 g of 3-methyl-2-nitrophenol and 6.3 g of 4-(4-methoxy)phenyl-1-(3-chloropropyl)-1H-imidazole in dimethylformamide. The obtained mixture was heated at 100° C. for 2 hours to conduct a reaction. After the completion of the reaction, the reaction mixture was extracted with ethyl acetate and the ethyl acetate layer was dried over magnesium sulfate and distilled to remove the solvent. The obtained oily substance was purified by silica gel chromatography to give 3.0 g of 2-nitro-3-[3-(4-phenyl-1H-imidazol-1-yl)propoxyltoluene. This product was catalytically reduced and condensed with 1.26 g of bromoacetyl chloride according to a conventional process to give 3.43 g of 2-(2-bromoacetamido)-3-[3-(4-phenyl-1H-imidazol-1-yl)propoxy]toluene. This product and a solution of 8 cc of butylamine in benzene were heated together under reflux for 2 hours to give 2.8 g of the title compound as an oil.

yield (%): 32 m.p. (°C.): oily substance

¹H-NMR (90 MHz, CDCl₃) δ ppm=0.90 (3H, t, J=6.0), 1.12~1.66 (4H, m), 1.92 (1H, m), 2.18 (2H, quintet, J=6.5), 2.26 (3H, s), 2.68 (2H, t, J=6.5), 3.41 (2H, s), 3.80 (3H, s), 3.96 (2H, t, J=6.5), 4.15 (2H, t, J=6.5), 6.68~7.88 (9H, m), 8.79 (1H, brs)

M/Z 407 (M+H)⁺

Example 64

N-[6-N,N-Dimethylamino-2-{3-(4-phenylpiperazin-1-yl)propoxy}]phenyl-N'-pentylurea

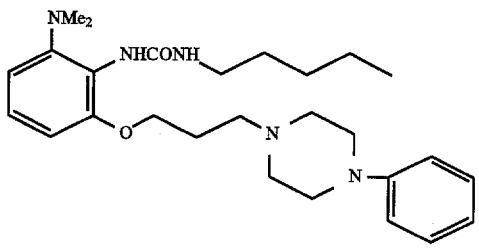

A solution of 480 mg of 1-phenylpiperazine in dimethylformamide was dropped into a suspension of 1 g of N-(6-N,N-dimethylamino-2-(3-chloropropyl)}phenyl-N'-pentylurea, 810 mg of potassium carbonate and a catalytic amount of sodium iodide in dimethylformamide. The obtained mixture was stirred at 60° C. for 2 hours to conduct a reaction. After the completion of the reaction, the reaction mixture was extracted with ethyl acetate. The ethyl acetate layer was washed with a saturated aqueous solution of common salt, dried over magnesium sulfate and distilled to remove the solvent. The residue was crystallized from a benzene/hexane mixture and recrystallized from ethyl acetate to give 500 mg of the title compound as a white crystal.

yield (%): 37 m.p. (°C.): 148 to 150

$^1$H-NMR (90 MHz, CDCl$_3$) δ ppm=0.91 (3H, t, J=6.0), 1.15~1.74 (6H, m), 2.01 (2H, quintet, J=6.5), 2.58 (2H, t, J=6.5), 2.64 (4H, m), 2.78 (6H, s), 3.20 (4H, m), 4.09 (2H, t, J=6.5), 6.34 (1H, brs), 6.51~7.38 (9H, m)

M/Z 468 (M+H)$^+$

The compounds which will be described in the following Examples 65 to 77 were prepared in a similar manner to that of Example 64.

Chemical structural formula, yield (%), melting point (°C.), mass spectrometry data (M+H)$^+$ and $^1$H-NMR (δ ppm, JHz) will now be given with respect to each of the compounds.

Example 65

N-[6-N,N-Dimethylamino-2-{3-(2-phenylethylamino)propoxy}]phenyl-N'-pentylurea

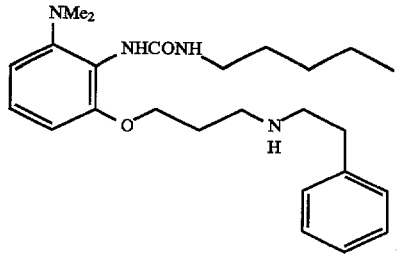

yield (%): 30 m.p. (°C.): 171 to 173

$^1$H-NMR (90 MHz, DMSO) δ ppm=0.86 (3H; t, J=6.0), 1.32 (6H, m), 1.92 (2H, quintet, J=6.5), 2.67 (6H, s), 2.90 (6H, m), 2.95 (2H, q, J=7.0), 4.02 (2H, t, J=6.5), 6.28 (1H, brt), 6.50~7.31 (9H, m)

M/Z 427 (M+H)$^+$

Example 66

N-[6-N,N-Dimethylamino-2-{3-(4-phenylpiperidin-1-yl)propoxy}]phenyl-N'-pentylurea

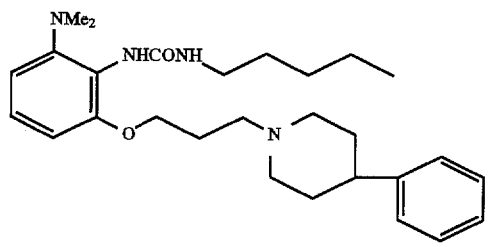

yield (%): 66 m.p. (°C.): 129 to 131

$^1$H-NMR (90 MHz, CDCl$_3$) δ ppm=0.88 (3H, t, J=6 0), 1.10~1.61 (6H, m), 1.65~2.40 (11H, m), 2.56 (4H, m), 2.76 (6H, s), 3.10 (4H, m), 4.07 (2H, t, J=6.5), 6.27 (1H, brs), 6.56~7.32 (9H, m)

M/Z 467 (M+H)$^+$

Example 67

N-[6-N,N-Dimethylamino-2-{3-(1H-benzimidazol-1-yl)propoxy}]phenyl-N'-pentylurea

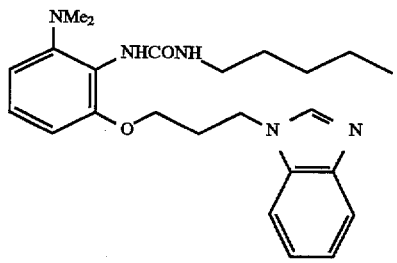

yield (%): 35 m.p. (°C.): 137 to 139

$^1$H-NMR (90 MHz, CDCl$_3$) δ ppm=0.88 (3H, t, J=6.0), 1.10~1.70 (6H, m), 2.35 (2H, quintet, J=6.5), 2.75 (6H, s), 3.20 (2H, q, J=6.5), 3.83 (2H, t, J=6.5), 4.46 (2H, t, J=6.5), 6.38~7.32 (8H, m), 7.68 (1H, brt), 7.80 (1H, brs)

M/Z 424 (M+H)$^+$

Example 68

N-[6-N,N-Dimethylamino-2-{3-(2H-1,2,3-triazol-2-yl)propoxy}]phenyl-N'-pentylurea

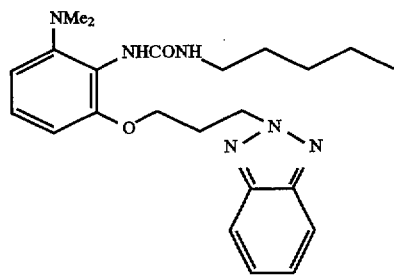

yield (%): 41 m.p. (°C.): 149 to 151

$^1$H-NMR (90 MHz, CDCl$_3$) δ ppm=0.91 (3H, t, J=6.0), 1.38 (6H, m), 2.62 (2H, quintet, J=6.5), 2.80 (6H, s), 3.23 (2H, q, J=7.0), 4.03 (2H, t, J=6.5), 4.99 (2H, t, J=6.5), 6.37 (1H, brt), 6.58~7.92 (8H, m)

M/Z 425 (M+H)$^+$

Example 69

N-2-[3-{4-(4-Chlorophenyl)piperazin-1-yl}-propoxy]phenyl-N'-butylurea

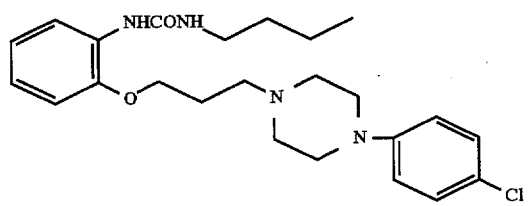

yield (%): 43 m.p. (°C.): 180 to 181

$^1$H-NMR (400 MHz, CDCl$_3$) δ ppm=0.89 (3H, t, J=7.6), 1.38 (2H, q, J=7.6), 1.53 (2H, q, J=7.6), 1.61 (4H, m), 2.43 (2H, quintet, J=7.2), 3.28 (2H, q, J=7.2), 3.30 (2H, t, J=7.2), 3.56 (4H, m), 4.05 (2H, t, J=7.2), 6.72~8.41 (10H, m)

M/Z 445 (M+H)$^+$

Example 70

N-2-[3-{4-(4-Chlorophenyl)piperazin-1-yl}propoxy]naphthyl-N'-butylurea

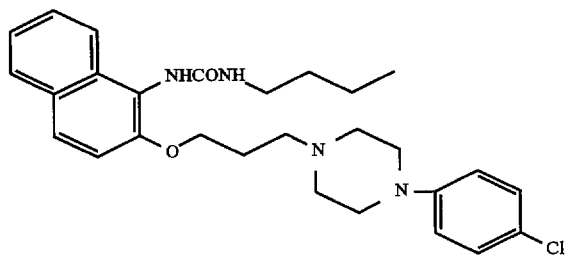

yield (%): 27 m.p. (°C.): 170 to 172

$^1$H-NMR (90 MHz, CDCl$_3$) δ ppm=0.82 (3H, t, J=6.5), 0.98~1.51 (4H, m), 2.00 (2H, quintet, J=6.5), 2.42~2.72 (6H, m), 3.00~3.30 (6H, m), 4.21 (2H, t, J=6.5), 4.50 (1H, brt), 6.24 (1H, brs), 6.78~8.04 (10H, m)

M/Z 495 (M+H)$^+$

Example 71

N-[5-(1,1-Dimethylethyl)-2-[3-{4-(4-chlorophenyl)piperazin-1-yl}propoxy]]phenyl-N'-butylurea

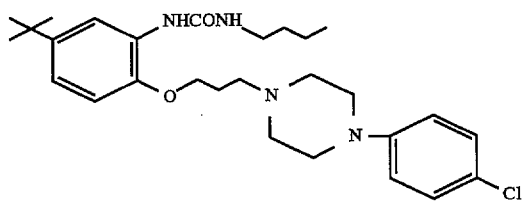

yield (%): 12 m.p. (°C.): 172 to 174

$^1$H-NMR (90 MHz, CDCl$_3$) δ ppm=0.88 (3H, t, J=6.5), 1.27 (9H, s), 1.62 (4H, m), 1.95 (2H, quintet, J=6.5), 2.38~2.63 (6H, m), 3.00~3.36 (6H, m), 4.01 (2H, t, J=6.5), 5.16 (1H, brt), 6.66~7.28 (7H, m), 8.02 (1H, d, J=1.5)

M/Z 501 (M+H)$^+$

Example 72

N-[6-Methyl-2-{3-(1H-benzimidazol-1-yl)propoxy}]phenyl-N'-butylurea

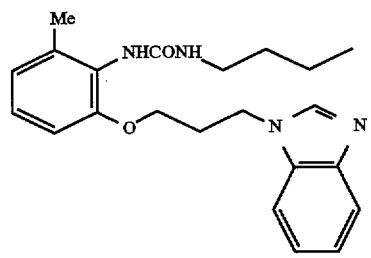

yield (%): 38 m.p. (°C.): 149 to 151

$^1$H-NMR (90 MHz, CDCl$_3$) δ ppm=0.83 (3H, t, J=6.5), 1.00~1.60 (4H, m), 2.19 (2H, quintet, J=6.5), 2.27 (3H, s), 3.16 (2H, q, J=6.5), 3.77 (2H, t, J=6.5), 4.31 (2H, t, J=6.5), 4.98 (1H, brt), 6.30 (1H, brs), 6.51 (1H, dd, J=7.2, 1.5), 6.76 (1H, dd, J=7.2, 1.5), 6.99 (1H, t, J=7.2), 7.02~7.85 (5H, m)

M/Z 381 (M+H)$^+$

Example 73

N-[2-[3-{4-(4-Chlorophenyl)piperazin-1-yl}propoxyl-5-propyl]phenyl-N'-butylurea

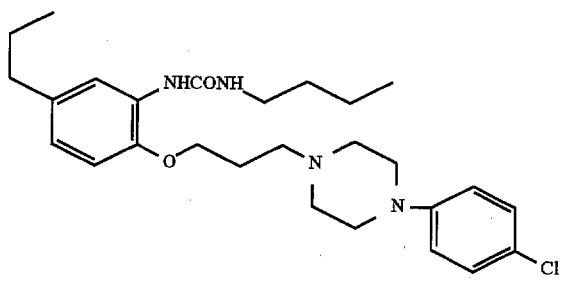

yield (%): 9 m.p. (°C.): 178 to 179

¹H-NMR (90 MHz, CDCl₃) δ ppm=0.93 (6H, t, J=6.5), 1.21~1.81 (6H, m), 2.02 (2H, quintet, J=6.5), 2.40~2.75 (8H, m), 3.00~3.38 (6H, m), 4.02 (2H, t, J=6.5), 5.02 (1H, brt), 6.65~7.24 (7H, m), 7.80 (1H, d, J=1.5)

M/Z 487 (M+H)⁺

Example 74

N-[4,5-Dimethyl-2-[3-{4-(4-chlorophenyl)piperazin-1-yl}propoxy]]phenyl-N'-butylurea

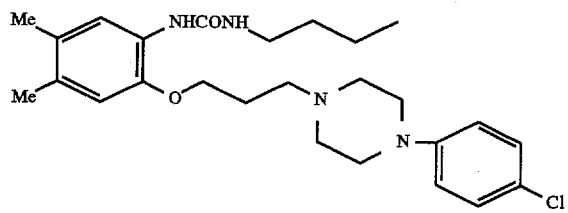

yield (%): 31 m.p. (°C.): 190 to 192

¹H-NMR (90 MHz, CDCl₃) δ ppm=0.91 (3H, t, J=6.5), 1.08~1.70 (4H, m), 1.95 (3H, s), 2.04 (2H, quintet, J=6.5), 2.19 (3H, s), 2.30~2.77 (6H, m), 3.00~3.34 (6H, m), 4.00 (2H, t, J=6.5), 4.95 (1H, brt), 6.59 (1H, s), 6.63 (1H, brs), 6.73 (2H, d, J=7.2), 7.15 (2H, d, J=7.2), 7.61 (1H, d, J=1.5)

M/Z 473 (M+H)⁺

Example 75

N-[5-(1H-Imidazol-1-yl)-2-[3-{4-(4-chlorophenyl)piperazin-1-yl}propoxy]]-N'-butylurea

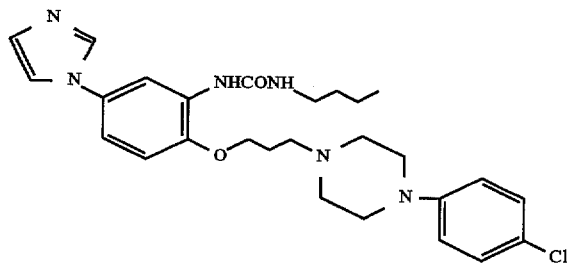

yield (%): 27 m.p. (°C.) 139 to 141

¹H-NMR (90 MHz, CDCl₃) δ ppm=0.88 (3H, t, J=6.5), 1.10~1.64 (4H, m), 1.90 (2H, quintet, J=6.5), 2.30~2.71 (6H, m, 2.81~3.42 (6H, m), 4.00 (2H, t, J=6.5), 6.33 (1H, brt), 6.62~7.93 (10H, m), 8.46 (1H, brs)

M/Z 511 (M+H)⁺

Example 76

2-N-[1-[3-{4-(4-Chlorophenyl)piperazin-1-yl}propoxy]]-naphthyl-N'-butylurea

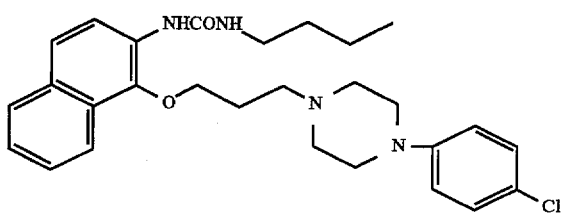

yield (%): 11 m.p. (°C.): 138 to 140

¹H-NMR (90 MHz, CDCl₃) δ ppm=0.85 (3H, t, J=6.8), 1.05~1.68 (4H, m), 2.10 (2H, quintet, J=6.5), 2.58~2.88 (6H, m), 3.01~3.38 (6H, m), 4.06 (2H, t, J=6.5), 5.56 (1H, brt), 6.67~8.18 (11H, m)

M/Z 495 (M+H)⁺

Example 77

N-2-{3-(1H-Benzimidazol-1-yl)propoxy}naphthyl-N'-butylurea

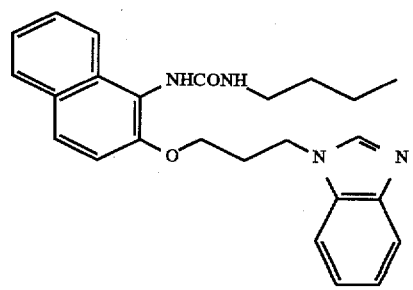

yield (%): 76 m.p. (°C.): 135 to 137

¹H-NMR (90 MHz, CDCl₃) δ ppm=0.80 (3H, t, J=7.2), 0.99~1.58 (4H, m), 2.28 (2H, quintet, J=6.5), 3.17 (2H, q, J=6.8), 3.94 (2H, t, J=6.5), 4.39 (2H, t, J=6.5), 4.70 (1H, brt), 6.39 (1H, brs), 6.99~8.02 (10H, m)

M/Z 417 (M+H)⁺

Example 78

N-[6-Methyl-2-[3-{4-(2-trans-carboxyvinyl)-1H-imidazol-1-yl}propoxy]]phenyl-N'-butylurea

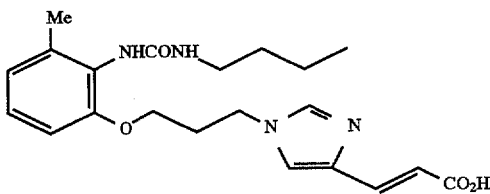

5 ml of 5% NaOH was added to a methanolic solution of the compound prepared in Example 59 by the same process as that of Example 1 which is an objective compound according to the present invention. The obtained mixture was stirred at room temperature for 5 hours to conduct a reaction. After the completion of the reaction, the reaction mixture was made acidic with acetic acid and extracted with chloroform. The chloroform layer was washed with a saturated aqueous solution of common salt, dried over magnesium sulfate and distilled to remove the solvent. The obtained residue was crystallized from ethyl acetate to give 560 mg of the title compound.

yield (%): 88 m.p. (°C.): 189 to 191

$^1$H-NMR (90 MHz, CDCl$_3$) δ ppm=0.88 (3H, t, J=6.5), 1.10-1.58 (4H, m), 2.10 (2H, quintet, J=6.5), 2.19 (3H, s), 3.06 (2H, q, J=6.5), 3.82 (2H, t, J=6.5), 4.18 (2H, t, J=6.5), 6.21 (1H, brt), 6.24 (1H, d, J=16.5), 6.76 (2H, dd, J=7.2, 1.5), 7.02 (1H, t, J=7.2), 7.16 (1H, brs), 7.52 (1H, d, J=16.5), 7.58 (1H, s), 7.68 (1H, s)

M/Z 401 (M+H)$^+$

The compound which will be described in the following Example 79 was prepared in a similar manner to that of Example 78.

Chemical structural formula, yield (%), melting point (°C.), mass spectrometry data (M+H)$^+$ and $^1$H-NMR (δ ppm, JHz) will be given with respect to the compound.

Example 79

N-[6-Methyl-2-[3-{4-(2-carboxyethyl)-1H-imidazol-1-yl}propoxy]]phenyl-N'-butylurea

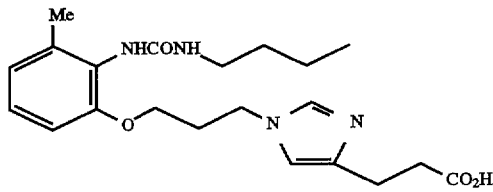

yield (%): 52 m.p. (°C.): 146 to 149

$^1$H-NMR (90 MHz, DMSO)

δ ppm=0.88 (3H, t, J=6.0), 1.10-1.49 (4H, m), 2.11 (2H, quintet, J=6.5), 2.18 (3H, s), 2.38-2.72 (4H, m), 3.08 (2H, q, J=6.5), 3.82 (2H, t, J=6.5), 4.09 (2H, t, J=6.5), 6.23 (1H, brt), 6.60-7.48(6H, m)

M/Z 403 (M+H)$^+$

Example 80

N-[6-Methyl-2-[3-{5-(1-methylethyl)-4-phenyl-1H-imidazol-1-yl}propoxy]]phenyl-N'-butylurea

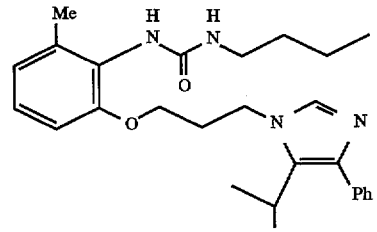

A solution of 186 g (0.709 mol) of 1-(3-chloro-propyl)-5-isopropyl-4-phenyl-1H-imidazol-1-yl in 500 ml of N,N-dimethylformamide, 103 g (0.744 mol) of potassium carbonate and 10 g (67.6 mol) of sodium iodide were added to a solution of 150 g (0.676 mol) of 2-butylureido-3-methylphenol in 500 ml of N, N-dimethylformamide. The obtained mixture was stirred at 80° C. for 7 hours to conduct a reaction. After the completion of the reaction, ethyl acetate was added to the reaction mixture. The obtained mixture was washed with water twice and with a saturated aqueous solution of common salt once, dried over magnesium sulfate and distilled to remove the solvent. The residue was purified by silica gel chromatography and recrystallized from an ethyl acetate/ethanol mixture to give 115 g of the title compound.

yield (%): 38 m.p. (° C.): 122 to 123

$^1$H-NMR (400 MHz, CDCl$_3$)

δ ppm=0.88 (3H, t, J=7.4), 1.26 (6H, d, J=7.2), 1.29 (2H, m), 1.43 (2H, quintet, J=7.6), 2.29 (3H, s), 2.31 (2H, quintet, J=6.0), 3.19 (2H, q, J=7.2), 3.28 (1H, heptet, J=7.2), 4.04 (2H, t, J=5.6), 4.22 (2H, t, J=6.4), 4.81 (1H, brs), 5.58 (1H, brs), 6.70–7.49 (9H, m)

M/Z 449 (M+H)$^+$

Example 81

N-[6-Methyl -2-{3-(5-ethyl-4-phenyl-1H-imidazol-1-yl)-propoxy}]phenyl-N'-butylurea or N-[2-{3-15-ethyl-4-phenyl-1H-imidazol-1-yl) propoxy}-6-methyl]phenyl-N'-butylurea

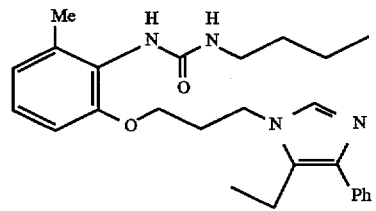

150 g of 2-butylureido-3-methylphenol and 168 g of 1-(3-chloropropyl )-5-ethyl-4-phenyl-1H-imidazol were dissolved in 1000 ml of N,N-dimethylformamide, followed by the addition of a catalytic amount of. sodium iodide and 187 g of potassium carbonate. The obtained mixture was heated at 80° C. for 4 hours, followed by the addition of 3 l of water. The resulting mixture was extracted with ethyl acetate. The organic layer was washed with an aqueous solution of common salt and water, dried over magnesium sulfate and distilled to remove the solvent. The residue was chromatographed over silica gel and eluted with benzene/acetone (2:1→0:1) to give 161 g of the title compound.

yield (%): 55 m.p. (° C.): 114 to 115

¹H-NMR (400 MHz, CDCl₃)

δ ppm=0.84 (3H, t, J=7.2), 1.17–1.29 (2H, m), 1.19 (3H, t, J=7.4), 1.33–1.41 (2H, m), 2.09–2.16 (2H, m), 2.22 (3H, s), 2.74 (2H, q, J=7.6), 3.10–3.16 (2H, m), 3.88 (2H, t, J=5.4), 4.04 (2H, t, J=6.6), 5.31 (1H, brs), 6.41 (1H, brs), 6.62 (1H, d, J=7.6), 6.79 (1H, d, J=7.6), 7.02 (1H, t, J=7.6), 7.20–7.62 (8H, m), 7.49 (1H, s)

M/Z 435 (M+H)⁺

The compounds which will be described in the following Examples 82 to 147 were prepared in a similar manner to that of Example 81.

Chemical structural formula, yield (%), melting point (° C.), mass spectrometry data (M+H)⁺ and ¹H-NMR (δ ppm, JHz) will now be given with respect to each of the compounds.

Example 82

N-[6-Methyl-2-{3-(5-methyl-4-phenyl-1H-imidazol-1-yl)-propoxyl}]phenyl-N'-2,2-dimethylpropylurea

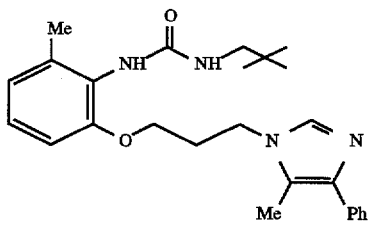

yield (%): 39 m.p. (° C.): 150 to 151

¹H-NMR (400 MHz, CDCl₃)

δ ppm=0.84 (9H, s), 2.26 (2H, quintet, J=5.6), 2.30 (3H, s), 2.37 (3H, s), 2.99 (2H, d, J=6.4), 3.97 (2H, t, J=5.6), 4.13 (3H, t, J=5.6), 4.82 (1H, brt), 5.70 (1H, brs), 6.68–7.63 (9H, m)

M/Z 435 (M+H)⁺

Example 83

N-[6-Methyl-2-{3-(5-hydroxyethyl-4-phenyl-1H-imidazol-1-yl)propoxy}]phenyl-N'-3-methylbutylurea

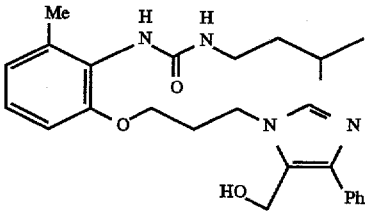

yield (%): 47 m.p. (° C.): 154 to 155

¹H-NMR (400 MHz, CDCl₃)

δ ppm=0.85 (6H, d, J=6.8), 1.31 (2H, q, J=7.6), 1.53 (1H, m), 2.30 (3H, s), 2.33 (2H, quintet, J=5.2), 3.22 (2H, q, J=6.8), 4.03 (2H, t, J=5.2), 4.26 (2H, t, J=5.2), 4.49 (1H, brt), 4.50 (1H, brt), 4.78 (2H, s), 5.80 (1H, brs), 6.72–7.74 (9H, m)

M/Z 451 (M+H)⁺

Example 84

N-[6-Methyl-2-{3-(5-ethyl-4-phenyl-1H-imidazol-1-yl)-propoxy}]phenyl-N'-pentylurea

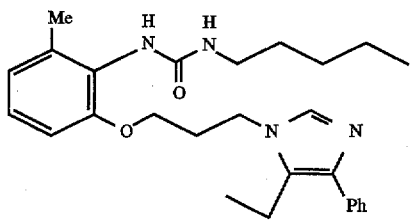

yield (%): 47 m.p. (° C.): 108 to 109

¹H-NMR (400 MHz, CDCl₃)

δppm=0.86 (3H, t, J=7.2), 1.20–1.48 (9H, m), 2.27 (2H, quintet, J=6.4), 2.29 (3H, s), 2.81 (2H, q, J=7.2), 3.18 (2H, q, J=7.2), 3.98 (2H, t, J=6.4), 4.15 (2H, t, J=6.4), 4.75 (1H, brt), 5.61 (1H, brs), 6.68–7.65 (9H, m)

M/Z 449 (M+H)⁺

Example 85

N-[6-Nitro-2-{3-(5-methyl-47phenyl-1H-imidazol-1-yl)-propoxy}]phenyl-N'-pentylurea

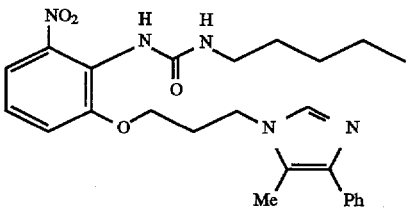

yield (%): 53 m.p. (° C.): 135 to 136

¹H-NMR (400 MHz, CDCl₃)

δ ppm=0.87 (3H, t, J=7.2), 1.18–1.41 (6H, m), 2.27 (2H, quintet, J=5.2), 2.38 (3H, s), 3.04 (2H, q, J=7.2), 4.09 (2H, t, J=5.2), 4.15 (2H, t, J=5.2), 6.03 (1H, brt), 6.90 (1H, brs ), 6.92–7.64 (9H, m)

M/Z 466 (M+H)⁺

Example 86

N-[6-N, N-Dimethylaminomethyl-2-{3-(5-methyl-4-phenyl-1H-imidazol-1-yl)propoxy}]phenyl-N'-pentylurea

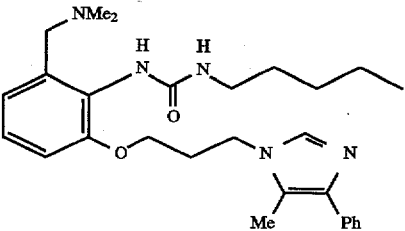

yield (%): 22 m.p. (° C.): 103 to 105

¹H-NMR (400 MHz, CDCl₃)

δ ppm=0.87 (3H, t, J=7.2), 1.21–1.56 (6H, m), 2.22 (2H, quintet, J=6.0), 2.36 (6H, s), 2.39 (3H, s), 2.75 (1H, brt), 3.20 (2H, q, J=7.2), 3.60 (2H, s), 3.96 (2H, t, J=6.0), 4.22 (2H, t, J=6.0), 6.07 (1H, brs), 6.82–7.65 (9H, m)

M/Z 478 (M+H)⁺

Example 87

N-[6-Chloro-2-{3-(5-methyl-4-phenyl-1H-imidazol-1-yl)-propoxy}]phenyl-N'-pentylurea

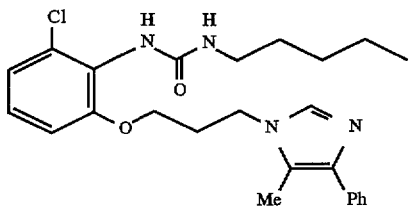

yield (%): 56 m.p. (° C.): 92 to 93

¹H-NMR (400 MHz, CDCl₃)

δ ppm=0.86 (3H, t, J=7.2), 1.19–1.51 (6H, m), 2.21 (2H, quintet, J=5.6), 2.38 (3H, s), 3.17 (2H, q, J=7.2), 3.98 (2H, t, J=5.6), 4.14 (3H, t, J=5.6), 4.83 (1H, brt), 5.95 (1H, s), 6.74–7.64 (9H, m)

M/Z 455 (M+H)⁺

Example 88

N-[2-{3-(5-Methyl-4-phenyl-1H-imidazol-1-yl)propoxy}-6-thiomethyl]phenyl-N'-pentylurea

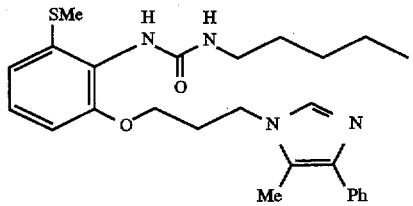

yield (%): 5.0 m.p. (° C.): 111 to 112

¹H-NMR (400 MHz, CDCl₃)

δ ppm=0.87 (3H, t, J=7.2), 1.18–1.51 (6H, m), 2.18 (2H, quintet, J=5.2), 2.38 (3H, s), 2.39 (3H, s), 3.18 (2H, q, J=7.2), 3.90 (2H, t, J=5.2), 4.09 (2H, t, J=5.2), 4.83 (1H, brt), 6.02 (1H, brs), 6.61–7.64 (9H, m)

M/Z 467 (M+H)⁺

Example 89

N-[6-Cyano-2-{3-(5-methyl-4-phenyl-1H-imidazol-1-yl)-propoxy}]phenyl-N'-pentylurea

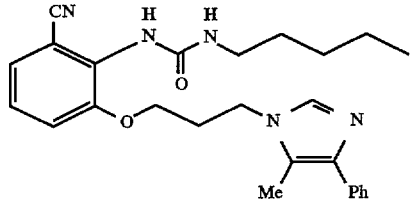

yield (%): 16 m.p. (° C.): 45 to 50

¹H-NMR (400 MHz, CDCl₃)

ppm=0.92 (3H, t, J=7.2), 1.10–1.79 (6H, m), 2.31 (2H, quintet, J=6.4), 2.41 (3H, s), 4 06 (2H, t, J=6.4), 4.12 (2H, q, J=7.2), 4.15 (2H, t, J=6.4), 6.91–7.65 (9H, m), 7.72 (1H, brs)

M/Z 446 (M+H)⁺

Example 90

N-[2-{3-(5-Methyl-4-phenyl-1H-imidazol-1-yl)propoxy}-6-sulfonylmethyl]phenyl-N'-pentylurea

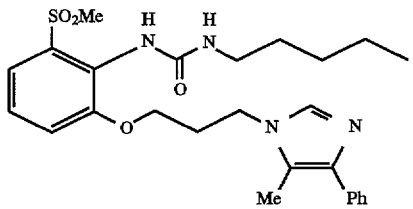

yield (%): 40 m.p. (20 C.): 175 to 176

¹H-NMR (400 MHz, CDCl₃)

ppm=0.86 (3H, t, J=6.8), 1.23–1.52 (6H, m), 2.19 (2H, quintet, J=5.6), 2.38 (3H, s), 3.11 (3H, s), 3.21 (2H, q, J=6.8), 3.99 (2H, t, J=5.6), 4.14 (3H, t, J=5.6), 5.46 (1H, brt), 7.10 (1H, brs), 7.10–7.64 (9H, m)

M/Z 499 (M+H)⁺

Example 91

N-Methyl-N-[6-N,N-dimethylamino-2-{3-(4-phenyl-1H-imidazol-1-yl)propoxy}]phenyl-N'-pentylurea

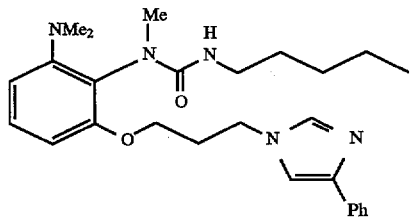

yield (%): 33 m.p. (° C.): 108 to 109

¹H-NMR (400 MHz, CDCl₃)

δ ppm=0.84 (3H, t, J=6.8), 1.15–1.45 (6H, m), 2.22 (2H, m), 2.84 (6H, s), 3.03 (1H, dt, J=6.9, 6.5), 3.16 (3H, s), 3.34 (1H, dt, J=6.8, 6.4), 3.88 (2H, m), 4.17 (2H, t, J=6.4), 4.51 (1H, brt), 6.41–7.76 (10H, m)

M/Z 464 (M+H)⁺

Example 92

N-[6-Fluoro-2-{3-(5-methyl-4-phenyl-1H-imidazol-1-yl)-propoxy}]phenyl-N'-pentylurea

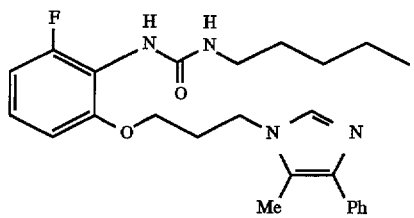

yield (%): 46
m.p. (° C.): 128 to 129
¹H-NMR (400 MHz, CDCl₃)
δ ppm=0.85 (3H, t, J=7.2), 1.12–1.47 (6H, m), 2.25 (2H, quintet, J=2), 4.02 (2H, t, J=5.2), 4.14 (2H, t, J=5.2), 5.07 (1H, brt), 5.75 (1H, brs), 6.60–7.66 (9H, m)
M/Z 439 (M+H)⁺

Example 93

N-[6-Methyl-2-{3-(5-chloro-4-phenyl-1H-imidazol-1-yl)propoxy}]phenyl-N'-pentylurea

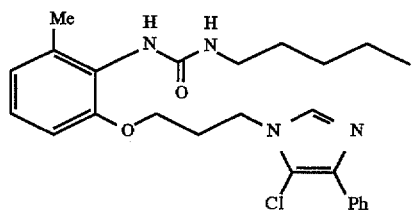

yield (%): 38
m.p. (° C.): 133 to 134
¹H-NMR (400 MHz, CDCl₃)
δ ppm=0.86 (3H, t, J=6.8), 1.18–1.50 (6H, m), 2.28 (2H, quintet, J=5.6), 2.30 (3H, s), 3.19 (2H, q, J=6.8), 3.95 (2H, t, J=5.6), 4.23 (2H, t, J=5.6), 4.52 (1H, brt), 5.63 (1H, brs), 6.68–7.96 (9H, m)
M/Z 455 (M+H)⁺

Example 94

N-[2-{3-(5-Chloro-4-phenyl-1H-imidazol-1-yl)propoxyl-6-sulfonylmethyl]phenyl-N'-pentylurea

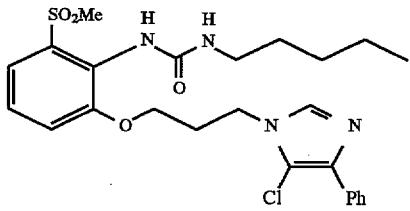

yield (%): 25
m.p. (° C.): 175 to 177
¹H-NMR (400 MHz, CDCl₃)
δ ppm=0.88 (3H, t, J=7.2), 1.24–1.60 (6H, m), 2.26 (2H, quintet, J=6.0), 3.09 (3H, s), 3.26 (2H, q, J=7.2), 4.00 (2H, t, J=6.0), 4.27 (2H, t, J=6.0), 4.99 (1H, brt), 6.98 (1H, brs), 7.11–7.96 (9H, m)
M/Z 519 (M+H)⁺

Example 95

N-[6-Methyl-2-{3-(4-phenyl-1H-imidazol-1-yl)propoxy}]-phenyl-N'-pentylurea

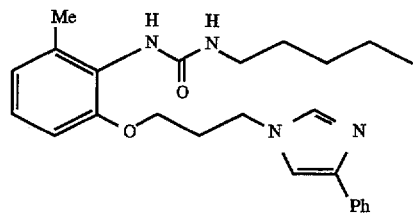

yield (%): 28
m.p. (° C.): 121 to 122
¹H-NMR (400 MHz, CDCl₃)
δ ppm=0.86 (3H, t, J=6.8), 1.17–1.50 (6H, m), 2.27 (2H, quintet, J=5.6), 2.29 (3H, s), 3.18 (2H, q, J=6.8), 3.94 (2H, t, J=5.6), 4.20 (2H, t, J=5.6), 4.57 (1H, brt), 5.63 (1H, brs), 6.68–7.75 (10H, m)
M/Z 421 (M+H)⁺

Example 96

N-[6-Methyl-2-{3-(4-hydroxymethyl-5-phenyl-1H-imidazol-1-yl)propoxy}]phenyl-N'-pentylurea

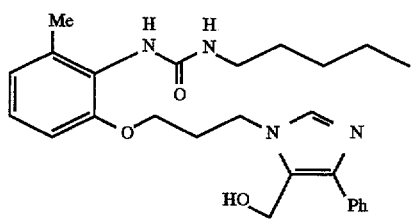

yield (%): 58
m.p. (° C.): 114 to 116
¹H-NMR (400 MHz, CDCl₃)
δ ppm=0.85 (3H, t, J=7.2), 1.15–1.46 (6H, m), 2.30 (3H, s), 2.32 (2H, quintet, J=5.2), 3.20 (2H, q, J=7.2), 4.04 (2H, t, J=5.2), 4.26 (2H, t, J=5.2), 4.53 (1H, brt), 4.54 (1H, brt), 4.78 (2H, s), 5.77 (1H, brs), 6.73–7.74 (9 H, m)
M/Z 451 (M+H)⁺

Example 97

N-[6-Methyl-2-[3-{4-(2-methylphenyl)-1H-imidazol-1-yl}propoxy]]phenyl-N'-pentylurea

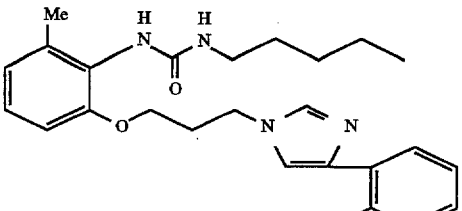

yield (%): 45
m.p. (° C.): 90 to 91
¹H-NMR (400 MHz, CDCl₃)
δ ppm=0.85 (3H, t, J=7.2), 1.17–1.44 (6H, m), 2.25 (2H, quintet, J=6.0), 2.29 (3H, s), 2.41 (3H, s), 3.17 (2H, q, J=7.2), 3.94 (2H, t, J=6.0), 4.22 (2H, t, J=6.0), 4.63 (1H, brt), 5.71 (1H, brs), 6.68–7.80 (9H, m)

M/Z 435 (M+H)⁺

Example 98

N-[6-Methyl-2-{3-(2-hydroxymethyl-5-methyl-4-phenyl-1H-imidazol-1-yl)propoxy}]phenyl-N'-pentylurea

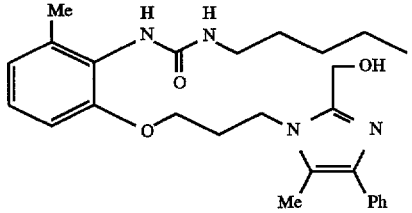

yield (%): 17 m.p. (° C.): 171 to 172

¹H-NMR (400 MHz, CDCl₃)

δ ppm=0.86 (3H, t, J=7.2), 1.18–1.48 (6H, m), 2.11 (2H, quintet, J=6.4), 2.30 (3H, s), 2.33 (3H, s), 3.18 (2H, q, J=7.2), 3.95 (2H, t, J=6.4), 4.15 (2H, t, J=6.5), 4.78 (2H, s), 4.82 (1H, brt), 6.04 (1H, brt), 6.13 (1H, brs), 6.66–7.55 (8H, m)

M/Z 465 (M+H)⁺

Example 99

N-[6-Methyl-2-{3-(2-(N-pentyl)aminomethyl-5-methyl-4-phenyl-1H-imidazol-1-yl}propoxy]phenyl-N'-pentylurea

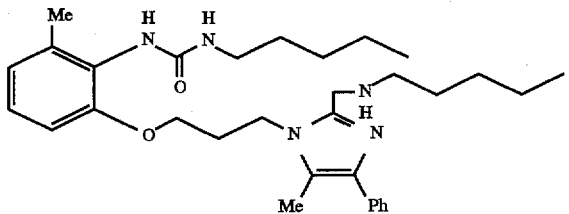

yield (%): 7 m.p. (° C.): 126 to 127

¹H-NMR (400 MHz, CDCl₃)

δ ppm=0.87 (6H, t, J=7.2), 1.13–1.56 (12H, m), 1.70 (1H, brt), 2.22 (2H, quintet, J=5.6), 2.31 (3H, s), 2.37 (3H, s), 2.65 (2H, t, J=7.2), 3.14 (2H, q, J=7.2), 3.87 (2H, s), 4.03 (2H, t, J=5.6), 4.22 (2H, t, J=5.6), 4.71 (1H, brt), 5.86 (1H, brs), 6.68–7.62 (8H, m)

M/Z 534 (M+H)⁺

Example 100

N-[6-Methyl-2-[3-{4-(2-nitrophenyl)-1H-imidazol-1-yl)-propoxyl]]phenyl-N'-pentylurea

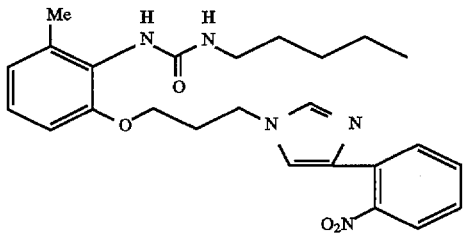

yield (%): 28 m.p. (° C.): 96 to 97

¹H-NMR (400 MHz, CDCl₃)

δ ppm=0.85 (3H, t, J=7.2), 1.15–1.48 (6H, m), 2.24 (2H, quintet, J=6.4), 2.31 (3H, s), 3.18 (2H, q, J=7.2), 3.91 (2H, t, J.=6.4), 4.20 (2H, t, J=6.4), 4.61 (1H, brt), 5.72 (1H, brs), 6.70–7.88 (9H, m)

M/Z 466 (M+H)⁺

Example 101

N-[6-Methyl-2-{3-(5-methoxymethyl-4-phenyl-1H-imidazol-1-yl)propoxy}]phenyl-N'-pentylurea

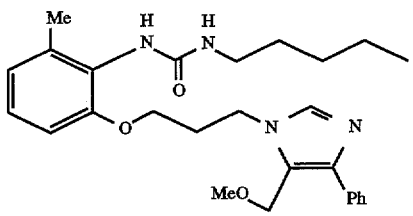

yield (%): 14

3 m.p. (° C.): 116 to 117

¹H-NMR (400 MHz, CDCl₃)

δ ppm=0.86 (3H, t, J=7.2), 1.09–1.50 (6H, m), 2.30 (3H, s), 2.31 (2H, quintet, J=6.0) 3.18 (2H, q, J=7.2), 3.35 (3H, s), 3.97 (2H, s), J=6.0), 4.24 (2H, t, J=6.0), 4.51 (2H, s), 4.72 (1H, brt), 5.74 (1H, brs), 6.68–7.63 (9H, m)

M/Z 465 (M+H)⁺

Example 102

N-16-Methyl-2-[3-{4-(2-methanesulfonylphenyl)-1H-imidazol-1-yl}propoxyl]]phenyl-N'-pentylurea

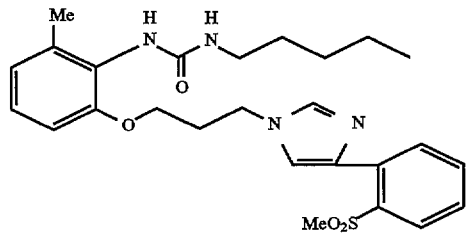

yield (%): 14 m.p. (° C.): 100 to 101

¹H-NMR (400 MHz, CDCl₃)

δ ppm=0.84 (3H, t, J=7.2), 1.15–1.50 (6H, m), 2.28 (2H, quintet, J=6.0), 2.31 (3H, s), 2.96 (3H, s), 3.16 (2H, q, J=7.2), 3.95 (2H, t, J=6.0), 4.26 (2H, t, J=6.0), 4.66 (1H, brt), 5.77 (1H, brs), 6.72–8.18 (9H, m)

M/Z 499 (M+H)⁺

Example 103

N-[6-Methyl-2-{3-(5-carboethoxy-4-phenyl-1H-imidazol-1-yl)propoxy}]phenyl-N'-pentylurea

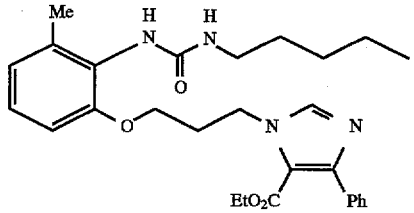

yield (%): 40 m.p. (° C.): 111 to 112

¹H-NMR (400 MHz, CDCl₃)

δ ppm=0.85 (3H, t, J=7.2), 1.17 (3H, t, J=7.2), 1.19–1.50 (6H, m), 2.30 (2H, quintet, J=5.6), 2.31 (3H, s), .3.21 (2H, q, J=7.2), 3.94 (2H, t, J=5.6), 4.20 (2H, q, J=7.2), 4.56 (2H, t, J=5.6), 4.64 (1H, brt), 5.84. (1H, brs), 6.69–7.63 (9H, m)

M/Z 493 (M+H)⁺

Example 104

N-[2-{3-(5-Methyl-4-phenyl-1H-imidazol-1-yl)propoxy}-6-sulfonylmethyl]phenyl-N'-3-methylbutylurea

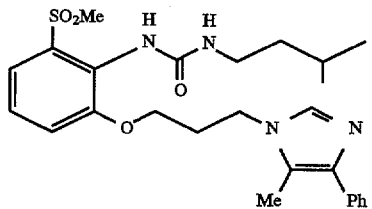

yield (%): 23 m.p. (° C.): 190 to 191

¹H-NMR (400 MHz, CDCl₃)

δ ppm=0.89 (6H, d, J=6.4), 1.41 (2H, q, J=6.8), 1.62 (1H, m), 2.21 (2H, quintet, J=6.4), 2.40 (3H, s), 3.10 (3H, s), 3.26 (2H, q, J=6.8), 4.04 (2H, t, J=6.4), 4.16 (2H, t, J=6.4), 5.12 (1H, brt), 6.99 (1H, brs), 7.12–7.65 (9H, m)

M/Z 499 (M+H)⁺

Example 105

N-[6-Methyl-2-[3-{4-(2-nitrophenyl)-1H-imidazol-1-yl}-propoxy]]phenyl-N'-pentylurea

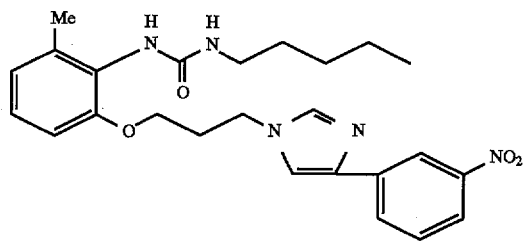

yield (%): 41 m.p. (° C.): 181 to 182

¹H-NMR (400 MHz, CDCl₃)

δ ppm=0.85 (3H, t, J=7.2), 1.18–1.50 (6H, m), 2.29 (2H, quintet, J=6.0), 2.31 (3H, s), 3.22 (2H, q, J=7.2), 3.94 (2H, t, J=6.0), 4.24 (2H, t, J=6.0), 4.56 (1H, brt), 5.73 (1H, brs), 6.70–8.52 (9H, m)

M/Z 466 (M+H)⁺

Example 106

N-[2-{3-(5-Chloro-4-phenyl-1H-imidazol-1-yl)propoxy}-6-sulfonylmethyl]phenyl-N'-3-methylbutylurea

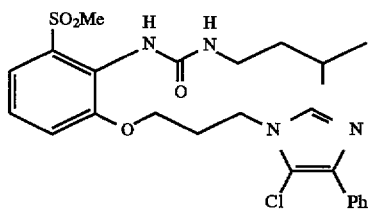

yield (%): 23 m.p. (° C.): 186 to 187

¹H-NMR (400 MHz, CDCl₃)

δ ppm=0.90 (6H, d, J=6.4), 1.41 (2H, q, J=6.8), 1.64 (1H, m), 2.27 (2H, quintet, J=5.6), 3.10 (3H, s), 3.30 (2H, q, J=6.8), 4.00 (2H, t, J=5.6), 4.27 (2H, t, J=5.6), 5.01 (1H, brt), 6.99 (1H, brs), 7.12–7.95 (9H, m)

M/Z 519 (M+H)⁺

Example 107

N-[6-Methyl-2-{3-(5-chloro-4-phenyl-1H-imidazol-1yl)-propoxy}]phenyl-N'-3-methtlbutylurea

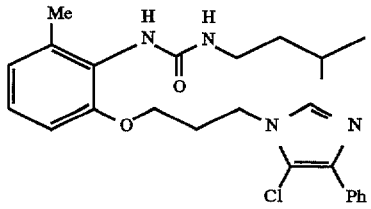

yield (%): 38 m.p. (° C.): 136 to 137

¹H-NMR (400 MHz, CDCl₃)

δ ppm=0.87 (6H, d, J=6.4), 1.33 (2H, q, J=7.2), 1:61 (1H, m), 2.28 (2H, quintet, J=6.4), 2.30 (3H, s), 3.21 (2H, q, J=7.2), 3.95 (2H, t, J=6.4i, 4.23 (2H, t, J=6.4), 4.47 (1H, brt), 5.63 (1H, brs), 6.69–7.95 (9H, m)

M/Z 455 (M+H)⁺

Example 108

N-[6-Methylamino-2-{3-(5-methyl-4-phenyl-1H-imidazol-1-yl)propoxy}]phenyl-N'-pentylurea

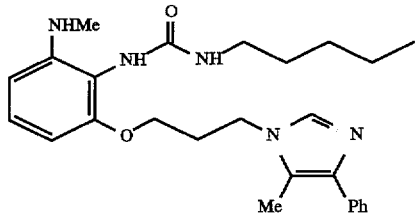

yield (%): 86
m.p. (° C.): 93 to 94
¹H-NMR (400 MHz, CDCl₃)
δ ppm=0.85 (3H, t, J=7.2), 1.21–1.45 (6H, m), 2.21 (2H, quintet, J=5.6), 2.38 (3H, s), 2.84 (3H, s), 3.16 (2H, q, J=7.2), 3.94 (2H, t, J=5.6), 4.13 (2H, t, J=5.6), 4.85 (1H, brt), 5.40 (1H, brs), 6.21–7.64 (9H, m)
M/Z 450 (M+H)⁺

Example 109

N-[2-{3-(5-(1-methylethyl)-4-phenyl-1H-imidazol-1-yl)-propoxy}-6-sulfonylmethyl]phenyl-N'-3-methylbutylurea

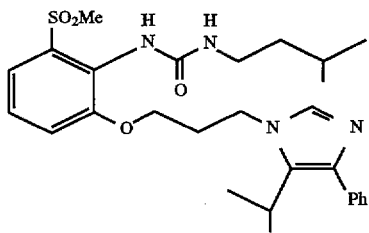

yield (%): 29
m.p. (° C.): 191 to 192
¹H-NMR (400 MHz, CDCl₃)
δ ppm=0.88 (6H, d, J=6.4), 1.28 (6H, d, J=7.2), 1.39 (2H, q, J=7.6), 1.63 (1H, m), 2.29 (2H, quintet, J=5.6), 3.10 (3H, s), 3.25 (2H, q, J=7.6), 3.28 (1H, septet, J=7.2), 4.11 (2H, t, J=5.6), 4.23 (2H, t, J=5.6), 5.17 (1H., brt), 6.89 (1H, brs), 7.16–7.61 (9H, m)
M/Z 527 (M+H)⁺

Example 110

N-[2-{3-(5-(1-Methylethyl)-4-phenyl-1H-imidazol-1-yl)-propoxy}-6-sulfonylmethyl]phenyl-N'-pentylurea

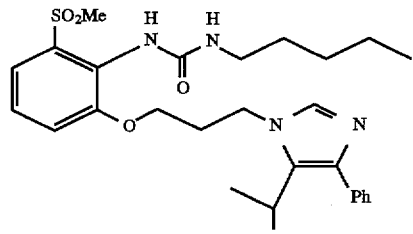

yield (%): 35
m.p. (° C.): 167 to 168

¹H-NMR (400 MHz, CDCl₃)
δ ppm=0.87 (3H, t, J=7.2), 1.26 (6H, d, J=6.8), 1.21–1.54 (6H, m), 2.28 (2H, quintet, J=6.0), 3.10 (3H, s), 3.21 (2H, q, J=7.2), 3.28 (1H, septet, J=6.8), 4.11 (2H, t, J=6.0), 4.23 (2H, t, J=6.0), 5.23 (1H, brt), 7.01 (1H, brs), 7.16–7.60 (9H, m)
M/Z 527 (M+H)⁺

Example 111

N-[6-Methyl-2-[3-{4-(2,4,6-trimethoxyphenyl)-1H-imidazol-1-yl}propoxy]]phenyl-N'-pentylurea

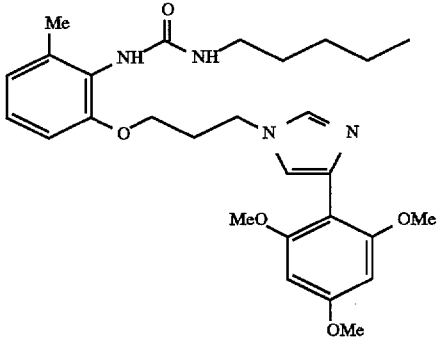

yield (%): 24
m.p. (° C.): oily substance
¹H-NMR (400 MHz, CDCl₃)
δ ppm=0.85 (3H, t, J=7.2); 1.23–1.45 (6H, m), 2.28 (2H, m), 2.27 (3H, s), 3.16 (2H, q, J=7.2), 3.70 (6H, s), 3.83 (3H, s), 3.99 (2H, t, J=5.2), 4.20 (2H, t, J=5.2), 5.25 (1H, brt), 5.74 (1H, brs), 6.17 (2H, s), 6.65–7.69 (5H, m)
M/Z 511 (M+H)⁺

Example 112

N-16-Methyl-2-[3-{4-(2,4-difluorophenyl)-1H-imidazol-1-yl}propoxy]]phenyl-N'-pentylurea

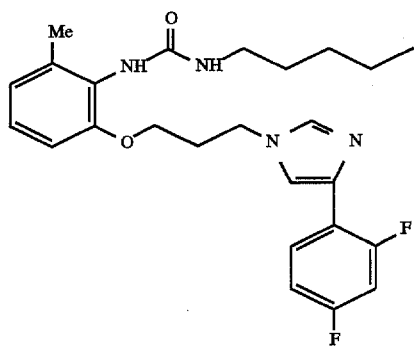

yield (%): 10
m.p. (° C.): 147 to 148
¹H-NMR (400 MHz, CDCl₃)
δ ppm=0.85 (3H, t, J=7.6), 1.22–1.46 (6H, m), 2.47 (2H, quintet, J=6.0), 2.30 (3H, s), 3.18 (2H, q, J=7.6), 3.91 (2H, t, J=6.0), 4.20 (2H, t, J=6.0), 4.65 (1H; brs), 5.86 (1H, brs), 6.67–8.09 (8H, m)
M/Z 457 (M+H)⁺

Example 113

N-[6-Methyl-2-{3-(5-chloro-4-phenyl-1H-imidazol-1-yl)-propoxy}]phenyl-N'-2,2-dimethylpropylurea

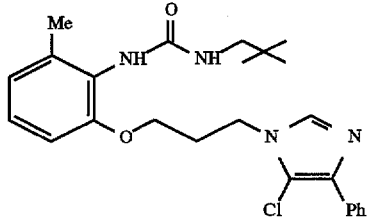

yield (%): 51 m.p. (° C.): 171 to 172

¹H-NMR (400 MHz, CDCl₃)

δ ppm=0.85 (9H, s), 2.27 (2H, q, J=5.6), 3.01 (2H, d, J=6.4), 3.95 (2H, t, J=5.6), 4.21 (2H, t, J=5.6), 4.64 (1H, brt), 5.72 (1H, brs), 6.70–7.93 (9H, m)

M/Z 455 (M+H)⁺

Example 114

N-[2-{3-(5-Ethyl-4-phenyl-1H-imidazol-1-yl)propoxy}-6-sulfonylmethyl]phenyl-N'-pentylurea

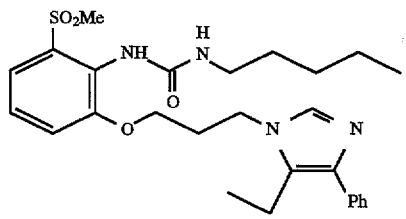

yield (%): 28 m.p. (° C.): 160 to 161

¹H-NMR (400 MHz, CDCl₃)

δ ppm=0.87 (3H, t, J=6.6), 1.23–1.40 (7H, m), 1.51 (2H, m), 2.24 (2H, quintet, J=6.4), 2.81 (2H, q, J=7.6), 3.10 (3H, s), 3.24 (2H, q, J=6.8), 4.05 (2H, t, J=5.6), 4.17 (2H, t, J=6.8), 5.14 (1H, brs), 6.99 (1H, brs), 7.14–7.66 (9H, m)

M/Z 513 (M+H)⁺

Example 115

N-[6-Methyl-2-{3-(4-phenyl-5-propyl-1H-imidazol-1-yl)-propoxy}]phenyl-N'-pentylurea

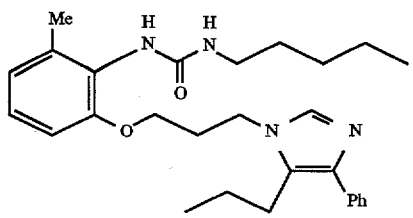

yield (%): 19 m.p. (° C.): 107 to 108

¹H-NMR (400 MHz, CDCl₃)

δ ppm=0.86 (3H, t, J=7.2), 0.96 (3H, t, J=7.6), 1.20–1.32 (.4H, m), 1.44 (2H, quintet, J=7.2), 1.60 (2H, sextet, J=7.6), 2.25 (2H, quintet, J=6.4), 2.28 (3H, s), 2.73 (2H, t, J=8.0), 3.17 (2H, q, J=6.8), 3.97 (2H, t, J=5.4), 4.13 (2H, t, J=6.4), 4.79 (1H, .brs), 5.66 (1H, s), 6.67–7.64 (9H, m)

M/Z 463 (M+H)⁺

Example 116

N-[2-{3-(5-methyl-4-phenyl-1H-imidazol-1-yl)propoxy}-6-sulfonylmethyl]phenyl-N'-butylurea

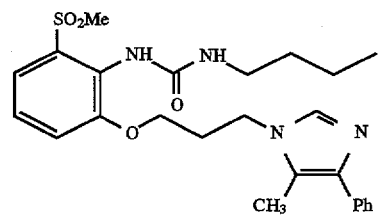

yield (%): 20 m.p. (° C.): 184 to 185

¹H-NMR (400 MHz, CDCl₃)

δ ppm=0.91 (3H, t, J=7.2), 1.34 (2H, sextet, J=7.2), 1.49 (2H, quintet, J=7.2), 2.21 (2H, quintet, J=5.8), 2.40 (3Y, s), 3.10 (3H, s), 3.25 (2H, q, J=7.2), 4.02 (2H, t, J=5.4), 4.16 (2H, t, J=6.6), 5.19 (1H, brs), 6.99 (1H, s), 7.12–7.64 (9H, m)

M/Z 485 (M+H)⁺

Example 117

N-[2-{3-(5-Hydroxymethyl-4-phenyl-1H-imidazol-1-yl)-propoxy}-6-sulfonylmethyl]phenyl-N'-pentylurea

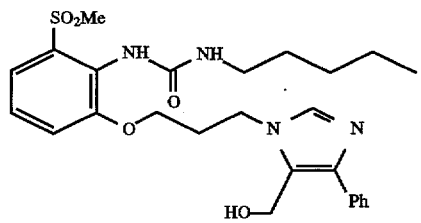

yield (%): 28 m.p. (° C.): 179 to 180

¹H-NMR (400 MHz, CDCl₃)

δ ppm=0.89 (3H, t, J=7.0), 1.29–1.55 (6H, m), 2.34 (2H, quintet, J=5.6), 2.57 (3H, brs), 3.12 (3H, s), 3.23 (2H, t, J=7.2), 4.07 (2H, t, J=5.2), 4.30 (2H, t, J=6.6), 4.66 (2H, s), 7.15–7.65 (9H, m)

M/Z 515 (M+H)⁺

Example 118

N-[6-Methyl-2-{3-(5-phenyl-4-propyl-1H-imidazol-1-yl)-propoxy}phenyl-N'-pentylurea

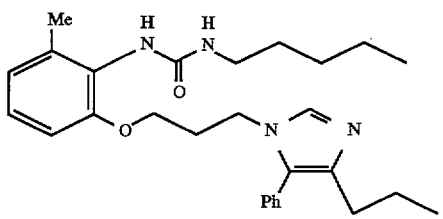

yield (%): 38
m.p. (° C.): 78 to 80
¹H-NMR (400 MHz, CDCl₃)
δ ppm=0.83 (3H, t, J=7.6), 0.87 (3H, t, J=6.8), 1.26 (4H, m), 1.46 (2H, quintet, J=7.0), 1.60 (2H, sextet, J=7.6), 1.95 (2H, quintet, J=6.0), 2.29 (3H, s), 2.42 (2H, t, J=7.6), 3.18 (2H, q, J=6.8), 3.72 (2H, t, J=5.6), 4.08 (2H, t, J=6.4), 4.80 (1H, brs), 5.46 (1H, brs), 6.54–7.50 (9H, m)
M/Z 463 (M+H)⁺

Example 119

N-[6-Methyl-2-{3-(1H, 8H, 9H-naphtho[2,1-d]imidazol-1-yl)propoxy}]phenyl-N'-pentylurea

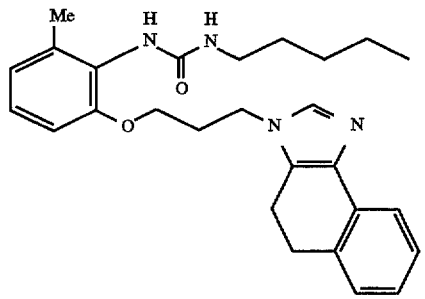

yield (%): 35
m.p. (° C.): 146 to 147
¹H-NMR (400 MHz, CDCl₃)
δ ppm=0.87 (3H, t, J=7.0), 1.26 (4H, m), 1.44 (2H, quintet, J=7.2), 2.20 (2H, quintet, J=6.0), 2.27 (3H, s), 2.78 (2H, t, J=7.8), 3.01 (2H, t, J=7.8), 3.92 (2H, t, J=5.4), 4.14 (2H, t, J=6.4), 4.58 (1H, brs), 5.59 (1H, brs), 6.65–7.74 (8H, m)
M/Z 447 (M+H)⁺

Example 120

N-[6-Methyl-2-{3-(4-phenyl-1H-imidazol-1-yl)propoxy}]-phenyl-N'-3-methylbutylurea

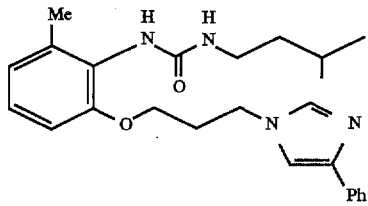

yield (%): 58
m.p. (° C.) 55 to 57
¹H-NMR (400 MHz, CDCl₃)

δ ppm=0.85 (6H, d, J=6.4), 1.31 (2H, q, J=7.2), 1.54 (1H, m), 2.19 (2H, m), 2.26 (3H, s), 3.19 (2H, q, J=6.0), 3.39 (2H, t, J=5.4), 4.14 (2H, t, J=6.4), 4.78 (1H, brs), 6.04 (1H, brs), 6.64–7.73 (10H, m)
M/Z 421 (M+H)⁺

Example 121

N-[6-Methyl-2-[3-{5-(1-methylethyl)-4-phenyl-1H-imidazol-1-yl}propoxy]]phenyl-N'-methylbutylurea

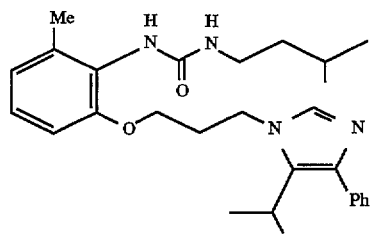

yield (%): 42
m.p. (° C.): 136 to 137
¹H-NMR (400 MHz, CDCl₃)
δ ppm=0.87 (6H, d, J=6.8), 1.27 (6H, d, J=7.2), 1.33 (2H, q, J=.6.8), 1.55 (1H, m), 2.29 (3H, s), 2.31 (2H, quintet, J=6.0), 3.21 (2H, q, J=60), 3.28 (1H, heptet, J=7.2), 4.04 (2H, t, J=5.6), 4.22 (2H, t, J=6.4), 4.81 (1H, brs), 5.62 (1H, brs), 6.72–7.49 (9H, m)
M/Z 463 (M+H)⁺

Example 122

N-[2-{3-(4-Phenyl-1H-imidazol-1-yl)propoxy}-6-sulfonylmethyl]phenyl-N'-pentylurea

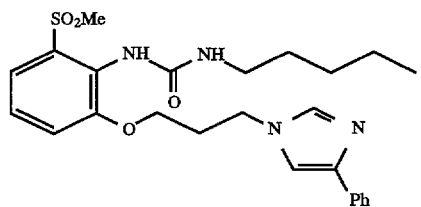

yield (%): 28
m.p. (° C.): 142 to 143
¹H-NMR (400 MHz, CDCl₃)
δ ppm=0.89(3H, t, J=6.8), 1.28–1.54 (6H, m), 2.50 (2H, quintet, J=5.4), 3.12 (3H, s), 3.27 (2H, q, J=6.8), 3.99 (2H, t, J=5.4), 4.24 (2H, t, J=6.4), 5.10 (1H, brs), 7.01–7.75 (11H, m)
M/Z 485 (M+H)⁺

Example 123

N-[6-Methyl-2-[3-{5-(1-methylethyl)-4-phenyl-1H-imidazol-1-yl}propoxy]]phenyl-N'-pentylurea

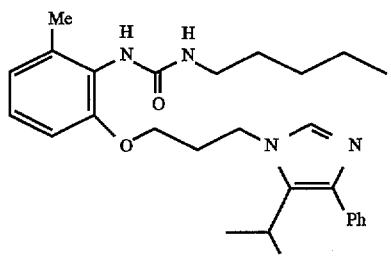

yield (%): 29
m.p. (° C.): 132 to 134
¹H-NMR (400 MHz, CDCl₃)

δ ppm=0.86 (3H, t, J=7.2), 1.22–1.48 (6H, m), 1.26 (1H, d, J=7.2), 2.30 (2H, quintet, J=6.4), 2.29 (3H, s), 3.18 (2H, q, J=5.8), 3.28 (1H, heptet, J=7.2), 4.03 (2H, t, J=5.4), 4.22 (2H, t, J=6.6), 4.85 (1H, brs), 5.63 (1H, brs), 6.68–7.49 (9H, m)

M/Z 463 (M+H)⁺

Example 124

N-[6-Methyl-2-[3-{4-(1-methylethyl)-5-phenyl-1H-imidazol-1-yl}propoxy]]phenyl-N'-pentylurea

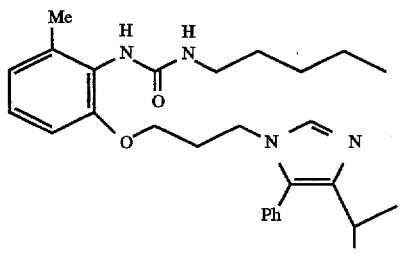

yield (%): 11
m.p. (° C.): 127 to 128
¹H-NMR (400 MHz, CDCl₃)

δ ppm=0.87 (3H, t, J=7.0), 1.18 (6H, d, J=6.4), 1.20–1.50 (6H, m), 1.98 (2H, quintet, J=5.2), 2.28 (3H, s); 2.79 (1H, heptet, J=6.4), 3.19 (2H, q, J=5.8), 3.74 (2H, d, J=5.2), 4.04 (2H, d, J=6.4), 4.85 (1H, brs), 5.39 (1H, brs), 6.54–7.52 (9H, m)

M/Z 463 (M+H)⁺

Example 125

N-[2-{3-(4-phenyl-1H-imidazol-1-yl)propoxy}-6-sulfonylmethyl]phenyl-N'-butylurea

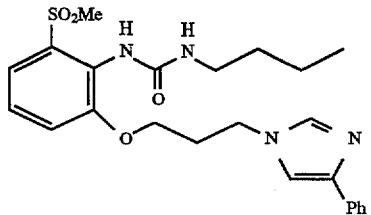

yield (%): 31
m.p. (° C.): 148 to 149
¹H-NMR (400 MHz, CDCl₃)

δ ppm=0.92 (3H, ,t, J=7.2), 1.36 (2H, sextet, J=7.2), 1.53 (2H, quintet, J=7.2), 2.26 (2H, quintet, J=5.6), 3.11 (3H, s), 3.28 (2H, q, J=7.2), 4.00 (2H, t, J=5.6), 4.25 (2H, t, J=6.4), 4.97 (1H, brs), 6.96 (1H, brs), 7.11–7.75 (10H, m)

M/Z 471 (M+H)⁺

Example 126

N-[2-{3-(5-Methyl-4-phenyl-1H-imidazol-1-yl)propoxy}]-phenyl-N'-pentylurea

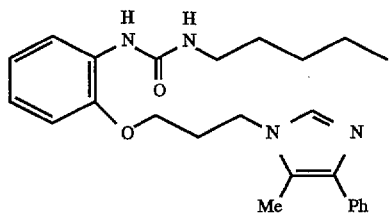

yield (%): 87
m.p. (° C.): 115 to 116
¹H-NMR (400 MHz, CDCl₃)

δ ppm=0.85 (3H, t, J=7.2), 1.15–1.37 (6H, m), 2.29 (2H, quintet, J=5.6), 2.35 (3H, s), 3.00 (2H, dt, J=7.2, 6.0), 4.08–4.15 (4H, m), 6.26 (1H, brs), 6.43 (1H, brt, J=7.2), 6.72–8.15 (10H, m)

M/Z 421 (M+H)⁺

Example 127

N-[6-Methyl-2-{3-(5-methyl-4-phenyl-1H-imidazol-1-yl)-propoxy}]phenyl-N'-pentylurea

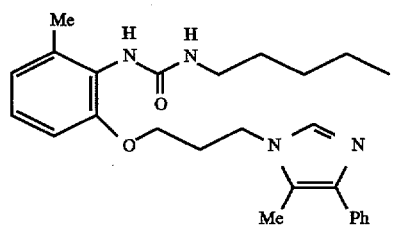

yield (%): 47
m.p. (° C.): 130 to 134
¹H-NMR (400 MHz, CDCl₃)

δ ppm=0.86 (3H, t, J=7.0), 1.19–1.46 (6H, m), 2.20 (2H, m), 2.28 (3H, s), 2.37 (3H, s), 3.15 (2H, q, J=6.6)., 3.94 (2H, t, J=5.6), 4.12 (2H, t, J=6.4), 4.77 (1H, brt), 5.80 (1H, brs), 6.66–7.64 (9H, m)

M/Z 435 (M+H)⁺

Example 128

N-[2-{3-(5-Methyl-4-phenyl-1H-imidazol-1-yl)propoxy}]-N'-pentylurea

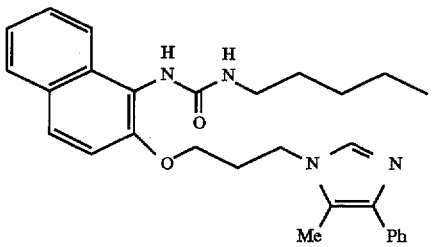

yield (%): 97
m.p. (° C.): 157 to 161
¹H-NMR (400 MHz, CDCl₃)

δ ppm=0.82 (3H, t, J=7.4), 1.12–1.42 (6H, m), 2.27 (2H, quintet, J=10.0), 2.41 (3H, s), 3.16 (2H, q, J=6.0), 4.11 (2H, t, J=5.6), 4.20 (2H, t, J=6.4), 4.55 (1H, brt), 6.00 (1H, brs), 7.20–8.04 (12H, m)

M/Z 471 (M+H)⁺

Example 129

N-[6-Hydroxy-2-{3-(5-methyl-4-phenyl-1H-imidazol-1-yl) propoxy}]phenyl-N'-pentylurea

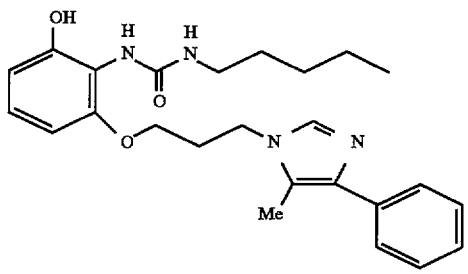

yield (%): 44
m.p. (° C.): 120 to 121
¹H-NMR (400 MHz, CDCl₃)

δ ppm=0.88 (3H, t, J=6.8), 1.20–1.41 (6H, m), 2.36 (3H, s), 2.36–2.42 (2H, m), 3.00–3.05 (2H, m), 4.16–4.21 (4H, m), 5.88 (1H, brs), 6.32 (1H, d, J=8.0), 6.63 (1H, d, J=8.4), 6.89 (1H, t, J=8.0), 7.10–7.59 (6H, m), 7.78 (1H, s), 10.52 (1H, brs)

M/Z 437 (M+H)⁺

Example 130

N-[6-Methoxy-2-{3-(5-methyl-4-phenyl-1H-imidazol-1-yl) propoxy}]phenyl-N'-pentylurea

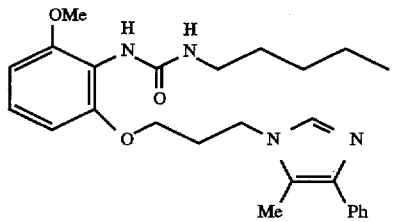

yield (%): 34
m.p. (° C.): 127
¹H-NMR (400 MHz, CDCl₃)

δ ppm=0.86 (3H, t, J=7.0), 1.05–1.51 (6H, m), 2.12–2.21 (2H, m), 2.37 (3H, s), 3.19 (2H, q, J=7.0), 3.82 (3H, s), 3.95 (2H, t, J=5.6), 4.12 (2H, t, J=6.0), 5.42 (1H, brt), 5.98 (1H, brs), 6.50–7.64 (8H, m)

M/Z 451 (M+H)⁺

Example 131

N-[6-Ethyl-2-{3-(5-methyl-4-phenyl-1H-imidazol-1-yl)-propoxy}]phenyl-N'-pentylurea

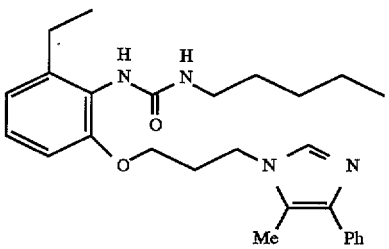

yield (%): 19
m.p. (° C.): 122 to 124
¹H-NMR (400 MHz, CDCl₃)

δ ppm=0.86 (3H, t, J=7.2), 1.18–1.46 (6H, m), 1.19 (3H, t, J=7.6), 2.19–2.26 (2H, m), 2.40 (3H, s), 2.68 (2H, q, J=7.6), 3.13–3.21 (2H, m), 3.95 (2H, t, J=5.4), 4.15 (2H, t, J=6.6), 4.51 (1H, m), 5.54 (1H, brs), 6.70–7.65 (9H, m)

M/Z 449 (M+H)⁺

Example 132

N-[2-{3-(5-methyl-4-phenyl-1H-imidazol-1-yl)propoxy}-6-propyl]phenyl-N'-pentylurea

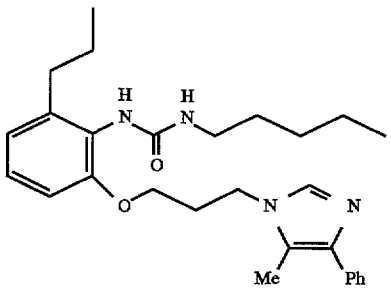

yield (%): 36
m.p. (° C.): 116 to 121
¹H-NMR (400 MHz, CDCl₃)

δ ppm=0.87 (3H, t, J=7.2), 0.96 (3H, t, J=6.0), 1.19–1.36 (4H, m), 2.19–2.30 (2H, m), 2.40 (3H, s), 2.60–2.67 (2H, m), 3.14–3.21 (2H, m), 3.97 (2H, t, J=5.6), 4.17 (2H, t, J=6.6), 4.62 (1H, brt), 5.65 (1H, brs), 6.70–7.66 (9H, m)

M/Z 463 (M+H)⁺

Example 133

N-[6-Hydroxymethyl-2-{3-(5-methyl-4-phenyl-1H-imidazol-1-yl)propoxy}]phenyl-N'-pentylurea

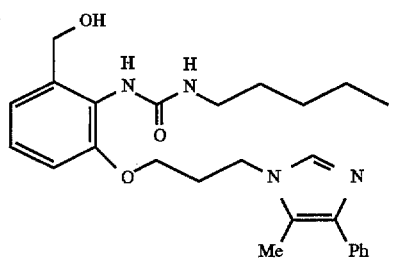

yield (%) 13 m.p. (° C.): oily substance

¹H-NMR(400 MHz, CDCl₃)

δ ppm=0.87 (3H, t, J=6.8), 1.21–1.36 (4H, m), 1.50–1.60 (2H, m), 2.18–2.25 (2H, m), 2.39 (3H, s), 3.28–3.36 (2H, m), 4.03 (2H, t, J=5.6), 4.23 (2H, t, J=6.8), 5.08 (3H, s), 6.59–7.65 (9H, m)

M/Z 433 (M-OH)⁺

Example 134

N-[6-Methyl-2-[3-{4-(4-nitro)phenyl-1H-imidazol-1-yl}-propoxy]]phenyl-N'-pentylurea

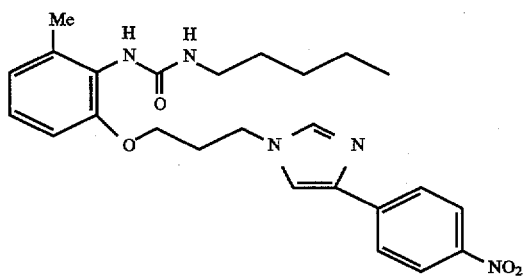

yield (%): 37 m.p. (° C.): 174 to 175

¹H-NMR (400 MHz, CDCl₃)

δ ppm=0.86 (3H, s), 1.19–1.35 (4H, m), 1.41–1.51 (2H, m), 2.30 (3H, s), 3.19–3.24. (2H, m), 3.96 (2H, t, J=5.6), 4.25 (2H, t, J=6.6), 4.50 (1H, brt), 5.65 (1H, brs), 6.72 (1H, d, J=7.8), 6.91 (1H, d, J=7.8), 7.15 (1H, t, J=7.8), 7.42 (1H, s), 7.57 (1H, s), 7.88 (1H, d, J=11.2), 8.22 (1H, d, J=11.2)

M/Z 466 (M+H)⁺

Example 135

N-[6-Methyl-2-[3-{4-(4-chloro) phenyl-1H-imidazol-1yl}propoxy]]phenyl-N'-pentylurea

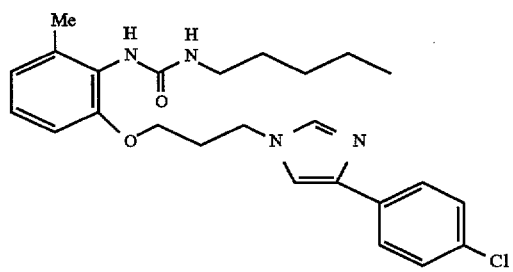

yield (%): 35 m.p. (° C.): 141 to 144

¹H-NMR (400 MHz, CDCl₃)

δ ppm=0.86 (3H, t, J=7.0), 1.19–1.35 (4H, m), 1.44 (2H, quintet, J=7.0), 2.21–2.29 (2H, m), 2.30 (3H, s), 3.19 (2H, dt, J=6.0, 7.2), 3.94 (2H, t, J=5.6), 4.20 (2H, t, J=6.4), 4.54 (1H, brt), 5.65 (1H, brs), 6.66–7.68 (9H, m)

M/Z 455 (M+H)⁺

Example 136

N-[6-Methyl-2-{3-(4-methyl-5-phenyl-1H-imidazol-1-yl)-propoxy}]phenyl-N'-pentylurea

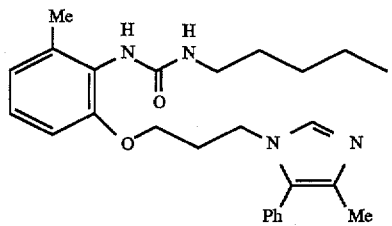

yield (%): 32 m.p. (° C.): oily substance

¹H-NMR (400 MHz, CDCl₃)

δ ppm=0.87 (3H, t, J=6.0), 1.20–1.51 (6H, m), 1.90–1.98 (2H, m), 2.17 (3H, s), 2.30 (3H, s), 3.13–3.21 (2H, m), 3.72 (2H, t, J=5.4), 4.13 (2H, t, J=6.2), 4.77 (1H, brt), 5.53 (1H, brs), 6.55 7.54 (9H, m)

M/Z 435 (M+H)⁺

Example 137

N-[6-Methyl-2-[3-{4-(3, 4, 5-trimethoxy)phenyl-1H-imidazol-1-yl}propoxy]]phenyl-N'-pentylurea

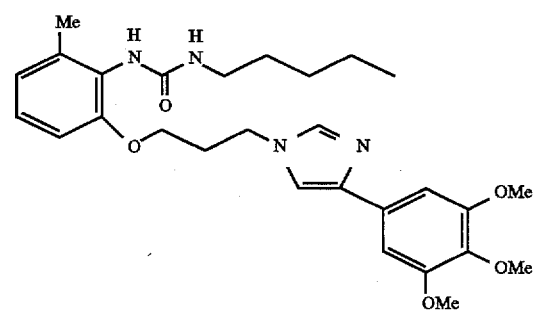

yield (%): 25 m.p. (° C.): oily substance

¹H-NMR (400 MHz, CDCl₃)

δ ppm=0.84 (3H, t, J=6.8), 1.17–1.29 (4H, m), 1.42 (2H, quintet, J=7.2), 2.15–2.22 (2H, m), 2.27 (3H, s), 3.16 (2H, q, J=6.8), 3.83–3.90 (2H, m), 3.85 (3H, s), 3.88 (6H, s), 4.14 (2H, t, J=6.4), 4.89 (1H, brs), 6.17 (1H, brs), 6.66 (1H, d, J=8.0), 6.84 (1H, d, J=8.0), 6.98 (2H, s), 7.08 (1H, t, J=8.0), 7.18 (1H, s), 7.49 (1H, s)

M/Z 511 (M+H)⁺

Example 138

N-[6-(1-Methylethyl)-2-{3-(5-methyl-4-phenyl-1H-imidazol-1-yl)propoxy}]phenyl-N'-pentylurea

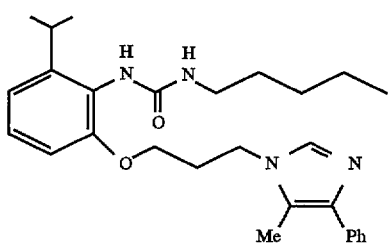

yield (%): 24
m.p. (° C.): 153 to 154
¹H-NMR (400 MHz, CDCl₃)
δ ppm=0.85 (3H, t, J=7.0), 1.19 (6H, d, J=6.8), 1.19–1.30 (4H, m), 1.39–1.46 (2H, m), 2.19–2.26 (2H, m), 2.41 (3H, s), 3.15–3.20 (2H, m), 3.33 (1H, septet, J=6.8), 3.95 (2H, t, J=5.4), 4.16 (2H, t, J=6.4), 4.61 (1H, brt), 5.63 (1H, brs), 6.69–7.64 (9H, m)
M/Z 463 (M+H)⁺

Example 139

N-[6-Methyl-2-(3-(5-chloro-4-phenyl-1H-imidazol-1-yl)-propoxy}]phenyl-N'-butylurea

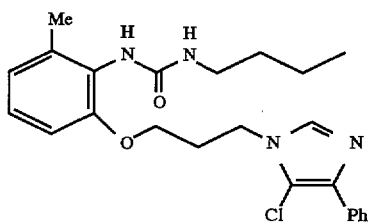

yield (%): 54
m.p. (° C.): 151 to 155
¹H-NMR (400 MHz, CDCl₃)
δ ppm=0.88 (3H, t, J=7.2), 1.24–1.48 (4H, m), 2.28–2.34 (2H, m), 2.28 (3H, s), 3.16–3.22 (2H, m), 3..94 (2H, t, J=5.4), 4.23 (2H, t, J=6.4), 4.69 (1H, brs), 5.85 (1H, brs), 6.68–7.95 (9H, m)
M/Z 441 (M+H)⁺

Example 140

N-[2-{3-(5-Ethyl-4-phenyl-1H-imidazol-1-yl)propoxy}-6-sulfonylmethyl]phenyl-N'-butylurea

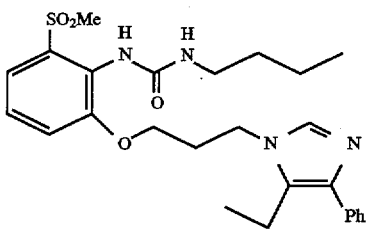

yield (%): 57
m.p. (° C.): 171 to 172
¹H-NMR (400 MHz, CDCl₃)
δ ppm=0.88 (3H, t, J=7.2), 1.23–1.52 (7H, m), 2.23–2.31 (2H, m), 2.82 (2H, q, J=7.6), 3.11 (3H, s), 3.19–3.24 (2H, m), 4.07 (2H, t, J=5.4), 4.30 (2H, t, J=6.6), 5.69 (1H, brs), 7.12–7.60 (9H, m), 8.08 (1H, brs)

M/Z 499 (M+H)⁺

Example 141

N-[2-{3-(5-Chloro-4-phenyl-1H-imidazol-1-yl)propoxy}-6-sulfonylmethyl]phenyl-N'-butylurea

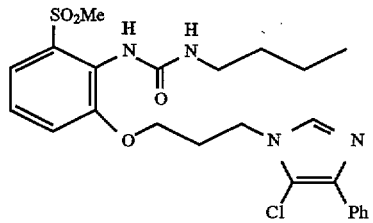

yield (%): 23
m.p. (° C.): 183 to 186
¹H-NMR (400 MHz, CDCl₃)
δ ppm=0.90 (3H, t, J=7.4), 1.29–1.52 (4H, m), 2.21–2.30 (2H, m), 3.11 (3H, s), 3.20–3.27 (2H, m), 3.96 (2H, t, J=5.6), 4.25 (2H, t, J=6.4), 5.38 (1H, brs), 7.08–7.94 (10H, m) p1 3 M/Z 505 (M+H)⁺

Example 142

N-[6-Methyl-2-{3-(5-hydroxymethyl-4-phenyl-1H-imidazol-1-yl)propoxy}]phenyl-N'-butylurea

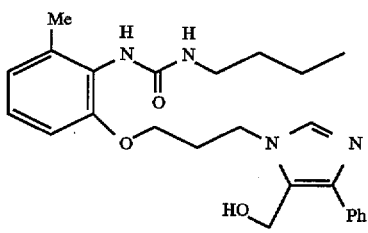

yield (%): 40
m.p. (° C.): 128 to 130
¹H-NMR (400 MHz, CDCl₃)
δ ppm=0.84 (3H, t, J=7.4), 1.20–1.41 (4H, m), 2.10–2.19 (2H, m), 2.25 (3H, s), 3.15 (2H, q, J=6.4), 3.86 (2H, t, J=5.0), 4.12 (2H, t, J=7.4), 4.67 (2H, s), 5.00 (1H, brs), 6.42 (1H, brs), 6.63 (1H, d, J=8.0), 6.82 (1H, d, J=8.0), 7.09 (1H, t, J=8.0), 7.21–7.67 (9H, m)
M/Z 437 (M+H)⁺

Example 143

N-[2-{3-(5-Hydroxymethyl-4-phenyl-1H-imidazol-1-yl)-propoxy}-6-sulfonylmethyl]phenyl-N'-butylurea

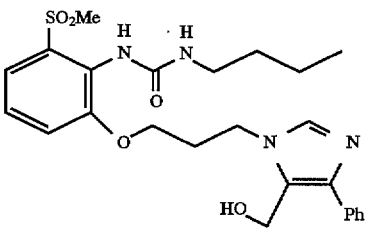

yield (%): 50
m.p. (° C.): 180 to 183

¹H-NMR (400 MHz, CDCl₃)

δ ppm=0.90 (3H, t, J=7.2), 1.25–1.52 (4H, m), 2.12–2.34 (2H, m), 3.10 (3H, s), 3.23 (2H, q, J=6.0), 4.00. (2H, t, J=5.2), 4.27 (2H, t, J=6.2),. 4.66 (3H, s), 5.56 (1H, brs), 7.07–7.69 (11H, m)

M/Z 501 (M+H)⁺

Example 144

N-[2-{3-(5-Methyl-4-phenyl-1H-imidazol-1-yl)propoxy}-6-sulfonylmethyl]phenyl-N'-cyclohexylurea

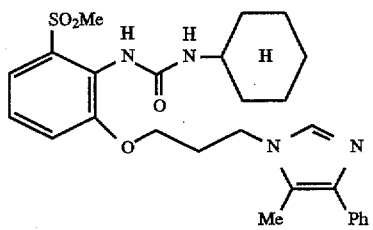

yield (%): 17 m.p. (° C.): 202 to 203

¹H-NMR (400 MHz, CDCl₃)

δ ppm=1.06–1.19 (5H, m), 1.54–1.74 (3H, m), 1.86–1.98 (2H, m), 2.16–2.21 (2H, m), 2.39 (3H, s), 3.12 (3H, s), 3.53–3.63 (1H, m), 3.99 (2H, t, J=5.2), 4.17 (2H, t, J=6.6), 5.41 (1H, brs), 7.09–7.66 (10H, m)

M/Z 511 (M+H)⁺

Example 145

N-[6-Methyl-2-{3-(5-ethyl-4-phenyl-1H-imidazol-1-yl)propoxy}]-N'-3-methylbutylurea

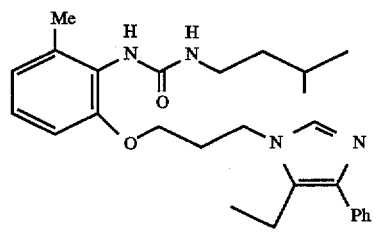

yield (%): 54 m.p. (° C.): 110 to 110

¹H-NMR (400 MHz, CDCl₃)

δ ppm=0.86 (6H, d, J=6.6), 1.22 (3H, t, J=7.6), 1.27–1.35 (2H, m), 1.50–1.60 (1H, m), 2.19–2.23 (2H, m), 2.27 (3H, s),. 2.74–2.80 (2H, m), 3.16–3.22 (2H, m), 3.94 (2H, t, J=5.6), 4.11 (2H, t, J=6.6), 4.93 (1H, brs), 5.97 (1H, brs), 6.65–7.64 (8H, m), 7.50 (1H, s)

M/Z 449 (M+H)⁺

Example 146

N-[6=Methyl-2-{3-(5-ethyl-4-phenyl-1H-imidazol-1-yl)propoxy}]phenyl-N'-2,2-dimethylpropylurea

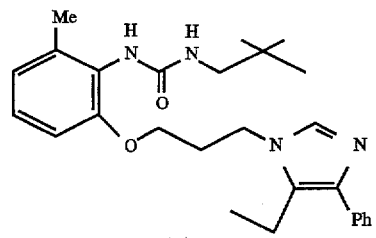

yield (%): 47 m.p. (° C.): oily substance

¹H-NMR (400 MHz, CDCl₃)

δ ppm=0.83 (9H, s), 1.88 (3H, t, J=7.4), 2.11–2.20 (2H, m), 2.25 (3H, s), 2.74 (2H, q, J=7.4), 2.98 (2H, d, J=6.0), 3.91 (2H, t, J=5.4), 4.06 (2H, t, J=6.8), 5.31 (1H, brs), 6.28 (1H, brs), 6.61–7.63 (8H, m), 7.50 (1H, s)

M/Z 449 (M+H)⁺

Example 147

N-[6-Methyl-2-{3-(4-phenyl-1H-imidazol-1-yl)propoxy}]-phenyl-N'-2,2-dimethylpropylurea

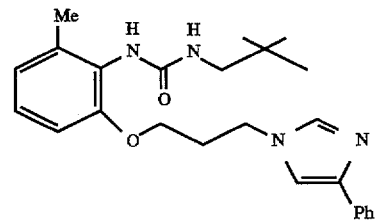

yield (%): 48 m.p. (° C.): 159 to 161

¹H-NMR (400 MHz, CDCl₃)

δ ppm=0.81 (9H, s), 2.07–2.14 (2H, m), 2.26 (3H, s), 2.98 (2H, d, J=6.4), 3.82 (2H, t, J=5.6), 4.06 (2H, t, J=6.6), 5.19 (1H, brs), 6.43 (1H, brs), 6.60–7.72 (8H, m), 7.14 (1H, d, J=1.4), 7.48 (1H, d, J=1.4)

M/Z 421 (M+H)⁺

Example 148

N-[6-Methyl-2-{3-(5-methyl-4-phenyl-1H-imidazol-1-yl)-propoxy}]phenyl-N'-butylurea

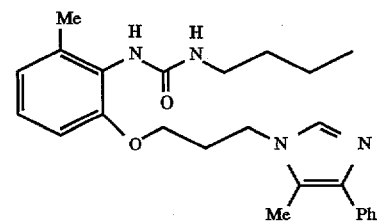

A solution of 430 mg of butyl isocyanate in chloroform was dropped into a solution of 1.16 g of. 6-methyl-2-{3-(5-methyl-4-phenyl-1H-imidazol-1-yl)- propoxy}aniline in chloroform. After the completion of the dropping, the obtained mixture was heated under reflux for 5 hours to conduct a reaction. After the completion of the reaction, the solvent was distilled off and the residue was recrystallized from ethyl acetate to give 1.56 g of the title compound.

yield (%): 100
m.p. (° C.): 139 to 140
¹H-NMR (400 MHz, CDCl₃)

δ ppm=0.88 (3H, t, J=7.2), 1.21–1.47 (4H, m), 2.26 (2H, quintet, J=5.6), 2.29 (3H, s), 2.38 (3H, s), 3.16 (2H, q, J=7.2), 3.96 (2H, t, J=5.6), 4.15 (2H, t, J=5.6), 4.67 (1H, brt), 5.63 (1H, brs), 6.67–7.65 (9H, m)

M/Z 421 (M+H)⁺

The compounds which will be described in the following Examples 149 to 152 were prepared in a similar manner to that of

Example 148.

Chemical structural formula, yield (%), melting point (° C.), mass spectrometry data (M+H)⁺ and ¹H-NMR (δ ppm, JHz) will now be given with respect to each of the compounds.

Example 149

N-[6-Methyl-2-{3-(5-methyl-4-phenyl-1H-imidazol-1-yl)-propoxy}]phenyl-N'-cyclohexylurea

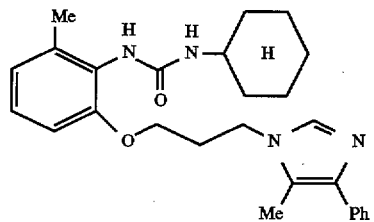

yield (%): 57
m.p. (° C.): 166 to 167
¹H-NMR (400 MHz, CDCl₃)

δ ppm=0.97–1.97 (10H, m), 2.23 (2H, quintet, J=5.6), 2.29 (3H, s), 2.39 (3H, s), 3.63 (1H, m), 3.96 (2H, t, J=5.6), 4.14 (2H, t, J=5.6), 4.51 (1H, brd), 5.62 (1H, brs), 6.67–7.65 (9H, m)

M/Z 447 (M+H)⁺

Example 150

N-[2-{2-(5-methyl-4-phenyl-1H-imidazol-1-yl)}ethyloxymethyl-6-methyl]phenyl-N'-pentylurea

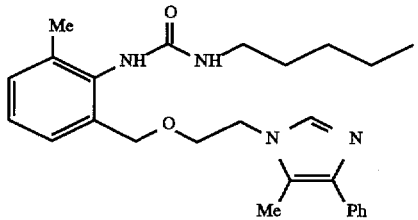

yield (%): 60
m.p. (° C.): 72 to 73
¹H-NMR (400 MHz, CDCl₃)

δ ppm=0.84 (3H, t, J=7.6), 1.19–2.04 (6H, m), 2.16 (3H, s), 2.32 (3H, s), 3.00 (2H, q, J=7.6), 3.68 (2H, t, J=5.2), 4.09 (2H, t, J=5.2), 4.34 (2H, s), 4.80 (1H, brs), 5.89 (1H, brs), 7.07–7.65 (9H, m)

M/Z 435 (M+H)⁺

Example 151

N-[6-Methyl-2-{2-hydroxy-3-(5-methyl-4-phenyl-1H-imidazol-1-yl)}propoxy]phenyl-N'-pentylurea

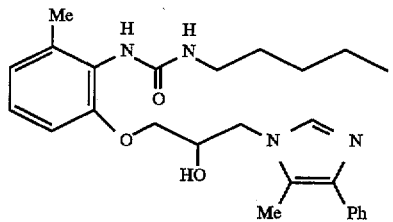

yield (%): 32
m.p. (° C.): 182 to 184
¹H-NMR (400 MHz, CDCl₃)

δ ppm=0.86 (3H, t, J=6.8), 1.20–1.50 (6H, m), 2.30 (3H, s), 2.39 (3H, s), 3.18 (2H, m), 3.86 (1H, m), 4.10 (4H, m), 6.70–7.60 (9H, m)

M/Z 451 (M+H)⁺

Example 152

N-[2-{2-(5-methyl-4-phenyl-1H-imidazol-1-yl)}-ethylthiomethyl-6-methyl]phenyl-N'-pentylurea

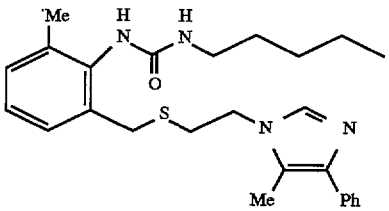

yield (%): 64
m.p. (° C.): 130 to 131
¹H-NMR (400 MHz, CDCl₃)

δ ppm=0.86 (3H, t, J=7.2), 1.20–1.50 (6H, m), 2.25 (3H, s), 2.31 (3H, s), 2.72 (2H, t, J=6.8), 3.14 (2H, q, J=6.4), 3.59 (2H, s), 3.95 (2H, t, J=6.8), 4.70 (1H, brs), 6.50 (1H, brs), 7.00–7.70 (9H, m)

M/Z 451 (M+H)⁺

Example 153

N-[6-Methyl-2-{3-(5-methyl-4-phenyl-1H-imidazol-1-yl)}propoxy]phenyl-N', N'-(pentane-1,5-diyl)urea

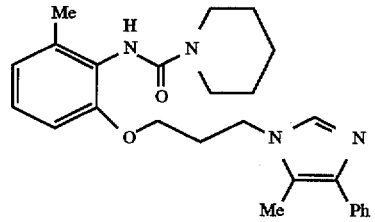

A toluene solution of 1.60 g of N-[6-methyl-2-{3-(5-methyl-4-phenyi-1H-imidazol-1-yl)-propoxy}]phenyl-0-phenylurethane derived from 6-methyl-2-{3-(5-methyl-4-phenyl-1H-imidazol-1-yl)-propoxy}aniline, and 930 mg of piperidine was heated under reflux for 30 minutes to conduct a reaction. After the completion of the reaction, the reaction mixture was concentrated, purified by column chromatography and recrystallized from an ethyl acetate/ethanol/hexane mixture to give 900 mg of the title compound.

yield (%): 57 m.p. (° C.): 167 to 168

¹H-NMR (400 MHz, CDCl₃)

δ ppm=1.52–1.68 (6H, m), 2.22 (2H, quintet, J=6.0), 2.23 (3H, s), 2.37 (3H, s), 3.47 (4H, m), 4.03 (2H, t, J=6.0), 4.08 (2H, t, J=6.0), 5.90 (1H, brs), 6.68–7.63 (9H, m)

M/Z 433 (M+H)⁺

The compounds which will be described in the following Examples 154 to 161 were prepared in a similar manner to that of Example 153.

Chemical structural formula, yield (%), melting point (° C.), mass spectrometry data (M+H)⁺ and ¹H-NMR ppm, JHz) will now be given with respect to each of the compounds.

Example 154

N-[6-Methyl-2-{3-(4-methyl-5-phenyl-1H-imidazol-1-yl)propoxy}]phenyl-N'-3-methoxypropylurea

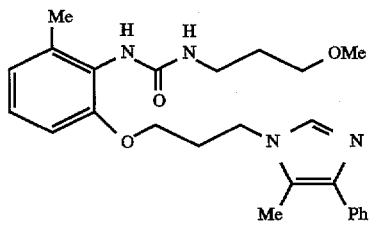

yield (%): 49 m.p. (° C.): 123 to 124

¹H-NMR (400 MHz, CDCl₃)

δ ppm=1.71 (2H, quintet, J=6.0), 2.21 (2H, quintet, J=6.0), 2.30 (3H, s), 2.38 (3H, s), 3.15 (3H, s), 3.30 (2H, q, J=6.0), 3.39 (2H, t, J=6.0), 3.95 (2H, t, J=6.0), 4.13 (2H, t, J=6.0), 5.22 (1H, brt), 5.71 (1H, brs), 6.68–7.64 (9H, m)

M/Z 437 (M+H)⁺

Example 155

N-[6-Methyl-2-{3-(5-methyl-4-phenyl-1H-imidazol-1-yl)propoxy}]phenyl-N'-2-ethoxyethylurea

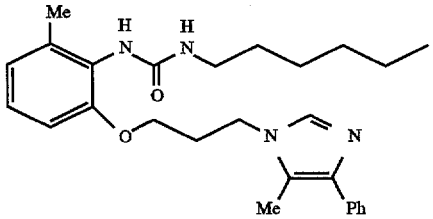

yield (%): 44 m.p. (° C.): 121 to 122

¹H-NMR (400 MHz, CDCl₃)

δ ppm=1.12 (3H, t, J=7.2), 2.22 (2H, quintet, J=6.0), 2.30 (3H, s), 2.38 (3H, s), 3.38 (2H, q, J=7.2), 3.43 (2H, t, J=7.2), 3.47 (2H, q, J=7.2), 3.96 (2H, t, J=6.0), 4.13 (2H, t, J=6.0), 5.01 (1H, brt), 5.78 (1H, brs), 6.69–7.64 (9H, m)

M/Z 437 (M+H)⁺

Example 156

N-[6-Methyl-2-{3-(5-methyl-4-phenyl-1H-imidazol-1-yl)propoxy}]phenyl-N',N'-(3-methylpentane-1,5-diyl)urea

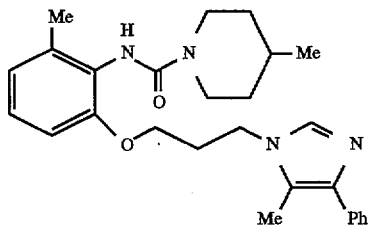

yield (%): 77 m.p. (° C.): 123 to 124

¹H-NMR (400 MHz, CDCl₃ )

δ ppm=0.96 (3H, d, J=6.8), 1.10–1.21 (2H, m), 1.58 (1H, m), 1.67 (2H, m), 2.21 (2H, quintet, J=5.6), 2.24 (3H, s), 2.37 (3H, s), 2.86 (2H, t, d, J=13.2, 2.8), 4.02 (2H, t, J=5.6), 4.06 (2H, m), 4.09 (2H, t, J=5.6), 5.91 (1H, brs), 6.68–7.63 (9H, m)

M/Z 447 (M+H)⁺

Example 157

N-[2-{3-(5-Methyl-4-phenyl-1H-imidazol-1-yl)propoxy}-6-sulfonylmethyl]phenyl-N'-hexylurea

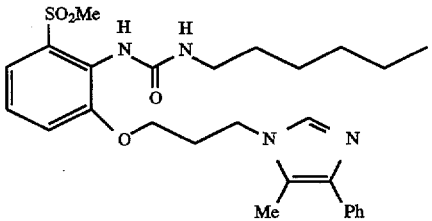

yield (%): 41 m.p. (° C.): 171 to 172

¹H-NMR (400 MHz, CDCl₃)

δ ppm=0.87 (3H, t, J=6.8), 1.19–1.54 (8H, m), 2.21 (2H, quintet, J=5.2), 2.40 (3H, s), 3.11 (3H, s), 3.25 (2H, q, J=6.8), 4.02 (2H, t, J=5.2), 4.16 (2H, t, J=5.2), 5.21 (1H, brt), 7.01 (1H, brs), 7.11–7.65 (9H, m)

M/Z 513 (M+H)⁺

Example 158

[2-[N-{2-(5-methyl-4-phenyl-1H-imidazol-1-yl) ethyl}-carbamoyl]-6-methyl]phenyl-N'-pentylurea

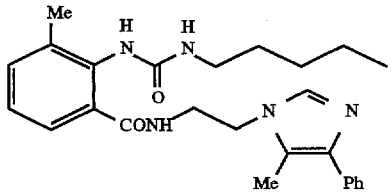

yield (%): 45 m.p. (° C.): 179 to 180

¹H-NMR (400 MHz, CDCl₃)

δ ppm=0.86 (3H, t, J=6.8), 1.16–1.41 (6H, m), 2.17 (3H, s), 2.34 (3H, s), 3.06 (2H, q, J=6.8), 3.51 (2H, q, J=6.0), 4.03 (2H, t, J=6.0), 5.27 (1H, brt), 7.09–7.58 (9H, m), 7.72 (1H, brs), 7.79 (1H, brt)

M/Z 448 (M+H)⁺

Example 159

N-[6-methyl-2-{3-(5-methyl-4-phenyl-1H-imidazol-1-yl-thiopropyl}]phenyl-N'-Pentylurea

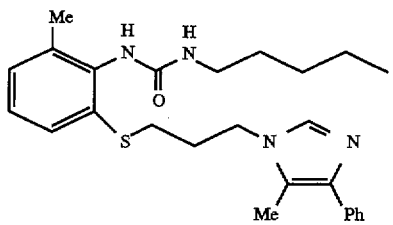

yield (%): 51 m.p. (° C.): 111 to 113

¹H-NMR (400 MHz, CDCl₃)

δ ppm=0.87 (3H, t, J=7.2), 1.18–1.50 (6H, m), 2.09 (2H, quintet, J=6.8), 2.30 (3H, s), 2.36 (3H, s), 2.84 (2H, t, J=6.8), 3.18 (2H, q, J=7.2), 4.07 (2H, t, J=6.8), 4.46 (1H, brt), 5.90 (1H, brs), 7.08–7.77 (9H, m)

M/Z 451 (M+H)⁺

Example 160

N-[6-Methyl-2-{3-(5-methyl-4-phenyl-1H-imidazol-1-yl)-propoxy}]phenyl-N'-3-methylbutylurea

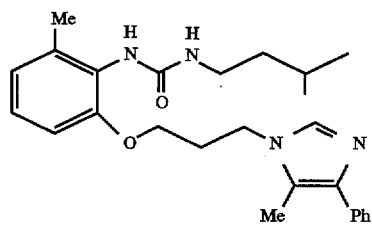

yield (%): 54 m.p. (° C.): 127 to 128

¹H-NMR (400 MHz, CDCl₃)

δ ppm=0.86 (6H, d, J=6.4), 1.31 (2H, q, J=7.2), 1.55 (1H, m), 2.20 (2H, quintet, J=6.4), 2.27 (3H, s), 2.37 (3H, s), 3.19 (2H, q, J=6.4), 3.94 (2H, t, J=6.4), 4.12 (2H, t, J=6.4), 4.70 (1H, brt), 5.78 (1H, brs), 6.66–7.63 (9H, m)

M/Z 435 (M+H)⁺

Example 161

N-[6-Methyl-2-{3-(5-methyl-4-phenyl-1H-imidazol-1-yl)-propoxy}]phenyl-N'-hexylurea

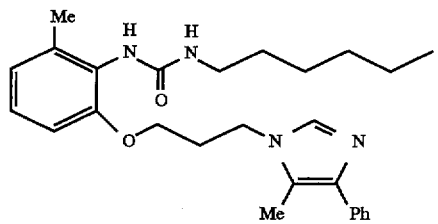

yield (%): 61 m.p. (° C.): 139 to 140

¹H-NMR (400 MHz, CDCl₃)

δ ppm=0.86 (3H, t, J=6.0), 1.17–1.46 (8H, m), 2.23 (2H, quintet, J=5.6), 2.30 (3H, s), 2.39 (3H, s), 3.15 (2H, q, J=6.0), 3.96 (2H, t, J=5.6), 4.14 (2H, t, J=5.6), 4.65 (1H, brt), 5.62 (1H, brs), 6.67–7.65 (9H, m)

M/Z 449 (M+H)⁺

Example 162

N-[2-{2-(5-Methyl-4-phenyl-1H-imidazol-1-yl)}ethyl-sulfinylmethyl-6-methyl]phenyl-N'-pentylurea

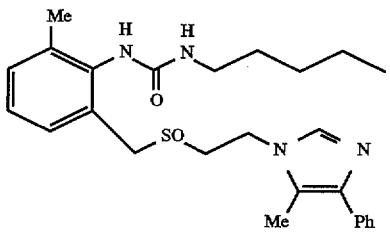

A solution of 12 mg of m-chloroperbenzoic acid in methylene chloride was dropped into a solution of 24 mg of N-[2-{2-(5-methyl-4-phenyl-1H-imidazol-1-yl)-ethylthiomethyl-6-methyl}phenyl-N'-pentylurea in methylene chloride at −78° C. After the completion of the dropping, the temperature of the mixture was allowed to rise spontaneously and the mixture was stirred for 2.5 hours to conduct a reaction. After the completion of the reaction, ether was added to the reaction mixture and excess peracid was decomposed with 1M sodium hydrogensulfite. The resulting mixture was washed with 1M Na₂CO₃ twice. The obtained organic layer was washed with a saturated aqueous solution of common salt, dried over magnesium sulfate and distilled to remove the solvent. The residue was purified by column chromatography to give 18 mg of the title compound as an amorphous substance.

yield (%): 73 m.p. (° C.): 116 to 118

¹H-NMR (400 MHz, CDCl₃)

δ ppm=0.88 (3H, t, J=6.8),. 1.20–1.60 (6H, m), 2.29 (3H, s), 2.38 (3H, s), 2.95 (2H, t, J=6.0), 3.18 (2H, q, J=6.4), 3.85 (1H, m), 4.26 (2H, m), 4.35 (1H, m), 4.71 (1H, brs), 7.00–7.62 (9H, m)

M/Z 467 (M+H)⁺

The compound which will be described in the following Example 163 was prepared in a similar manner to that of Example 162.

Chemical structural formula, yield (%), melting point (° C.), mass spectrometry data (M+H)⁺ and ¹H-NMR (δ ppm, JHz) will now be given with respect to the compound.

Example 163

N-[6-Methyl-2-{3-(5-methyl-4-phenyl-1H-imidazol-1-yl)-sulfinylpropyl}]phenyl-N'-pentylurea

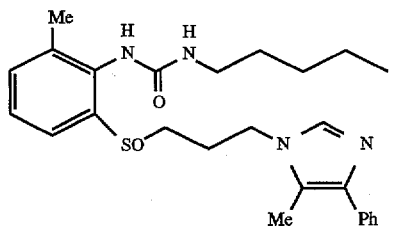

yield (%): 97
m.p. (° C.): oily substance
¹H-NMR (400 MHz, CDCl₃)

δ ppm=0.87 (3H, t, J=6.8), 1.20–1.50 (6H, m), 2.01 (2H, m), 2.18 (3H, s), 2.37 (3H, s), 2.83 (1H, dt, J=13.2, 7.2), 3.02 (1H, dt, J=13.2, 7.2), 3.15 (2H, m), 4.01 (2H, t, J=7.2), 5.58 (1H, brs), 7.0–7.60 (9H, m)
M/Z 467 (M+H)⁺

Example 164

N-[6-Methyl-2-{3-(5-methyl-4-phenyl-1H-imidazol-1-yl)-sulfonylpropyl}]phenyl-N'-pentylurea

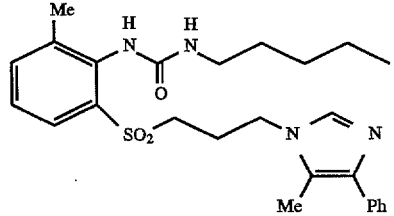

540 mg of m-chloroperbenzoic acid was added to a methylene chloride solution of 700 mg of N-[6-methyl-2-{3-(5-methyl-4-phenyl-1H-imidazol-1-yl)propylthio}]-phenyl-N'-pentylurea under cooling with ice. After 30 minutes, the temperature of the mixture was raised to room temperature and the resulting mixture was stirred for one hour to conduct a reaction. After the completion of the reaction, excess peracid was decomposed with an aqueous solution of sodium thiosulfate. The resulting mixture was extracted with ethyl acetate. The ethyl acetate layer was washed with 1N sodium hydroxide and a saturated aqueous solution of common salt, dried over magnesium sulfate and distilled to remove the solvent. The residue was purified by column chromatography to give 560 mg of the title compound as an amorphous substance.

yield (%) : 74
m.p. (° C.): 45 to 47
¹H-NMR (400 MHz, CDCl₃)

δ ppm=0.87 (3H, t, J=6.8), 1.18–1.52 (6H, m), 2.15 (2H, quintet, J=7.2), 2.32 (3H, s), 2.34 (3H, s), 3.14 (2H, t, J=7.2), 3.17 (2H, q, J=6.8), 4.01 (2H, t, J=7.2), 5.10 (1H, brt), 7.21–7.83 (10H, m)
M/Z 483 (M+H)⁺

The compounds which will be described in the following Examples 165 to 166 were prepared in a similar manner to that of Example 164.

Chemical structural formula, yield (%), melting point (° C.), mass spectrometry data (M+H)⁺ and ¹H-NMR ppm, JHz) will now be given with respect to each of the compounds.

Example 165

N-[2-{2-(5-Methyl-4-phenyl-1H-imidazol-1-yl)}ethyl-sulfonylmethyl-6-methyl]phenyl-N'-pentylurea

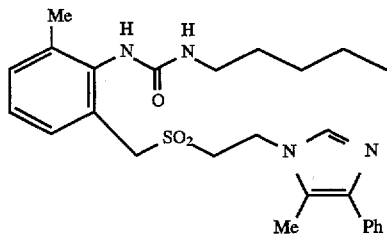

yield (%): 85
m.p. (° C.): 168 to 170
¹H-NMR (400 MHz, CDCl₃)

δ ppm=0.88 (3H, t, J=6.8), 1.27–1.63 (6H, m), 2.31 (3H, s), 2.42 (.3H, s), 3.18 (2H, q, J=6.0), 3.38 (2H, t, J=6.8), 4.19 (2H, s), 4.40 (2H, t, J=6.8), 6.61 (1H, brs), 7.10–7.65 (9H, m)
M/Z 483 (M+H)⁺

Example 166

N-[6-Methyl-2-{3-(4-methanesulfonylmethyl-5-phenyl-1H-imidazol-1-yl)propoxy}]phenyl-N'-pentylurea

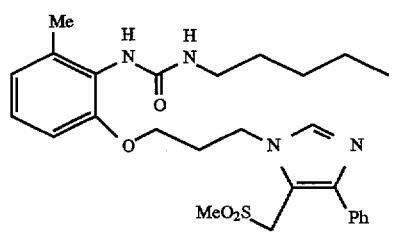

yield (%): 51
m.p. (° C.): 108 to 110
¹H-NMR (400 MHz, CDCl₃)

δ ppm=0.86 (3H, t, J=7.2), 1.18–1.50 (6H, m), 2.31 (3H, s), 2.34 (2H, quintet, J=5.6), 2.57 (3H, s), 3.18 (2H, q, J=7.2), 4.04 (2H, t, J=5.6), 4.40 (2H, t, J=5.6), 4.66 (2H, s), 4.78 (1H, brt), 5.99 (1H, brs), 6.71–7.79 (9H, m)
M/Z 513 (M+H)⁺

Example 167

N-[6-Methyl-2-[3-{4-(2-methanesulfonylamino)phenyl-1H-imidazol-1-yl)}propoxy]]phenyl-N'-pentylurea

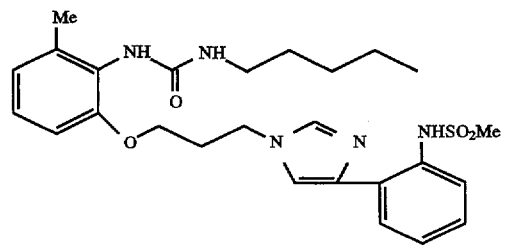

100 mg of palladium-carbon was added to an ethanolic solution of 1.18 g of N-[6-methyl-2-[3-{4-(2-nitrophenol)-1H-imidazol-1-yl}propoxy]]phenyl-N'-pentylurea to conduct catalytic reduction in a stream of hydrogen. Thus, 1.10 g of N-[6-methyl-2-[3-{4-(2-aminophenyl)-1H-imidazol-1-yl}propoxy]]phenyl-N'-pentylurea was obtained. A solution of 0.53 cc of triethylamine and 660 mg of methanesulfonic anhydride in methylene chloride was dropped into a solution of this product in methylene chloride under cooling with ice. The obtained mixture was stirred for 30 minutes and the temperature of the mixture was raised to room temperature, followed by the stirring for one hour. After the completion of the reaction, the reaction mixture was extracted with ethyl acetate and the ethyl acetate layer was dried over magnesium sulfate and distilled to remove the solvent. The residue was purified by column chromatography to give 370 mg of the title compound as an amorphous substance.

yield (%): 39 m.p. (° C.): 65 to 70

¹H-NMR (400 MHz, CDCl₃)

δ ppm=0.85 (3H, t, J=7.2), 1.18–1.50 (6H, m), 2.72 (2H, quintet, J=5.6), 2.32 (3H, s), 2.90 (3H, s), 3.20 (2H, q, J=7.2), 3.93 (2H, t, J=5.6), 4.24 (2H, t, J=5.6), 4.45 (1H, brt), 5.73 (1H, brs), 6.67–7.68 (9H, m)

M/Z 514 (M+H)⁺

The compounds which will be described in the following Examples 168 to 172 were prepared in a similar manner to that of Example 167.

Chemical structural formula, yield (%), melting point (° C.), mass spectrometry data. (M+H)⁺ and ¹H-NMR (δ ppm, JHz) will now be given with respect to each of the compounds.

Example 168

N-[2-{3-(5-Methyl-4-phenyl-1H-imidazol-1-yl)propoxy}-6-trifluoromethanesulfonylamino]phenyl-N'-pentylurea

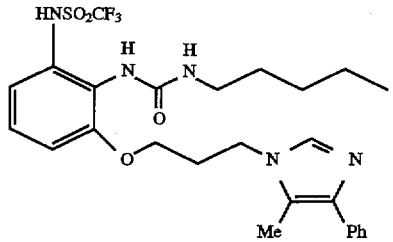

yield (%): 46 m.p. (° C.): 111 to 113

¹H-NMR (400 MHz, CDCl₃)

δ ppm=0.87 (3H, t, J=7.2), 1.18–1.44 (6H, m), 2.37 (2H, quintet, J=4.5), 2.39 (3H, s), 3.05 (2H, q, J=7.2), 4.03 (1H, brt), 4.15 (2H, t, J=4.5), 4.18 (2H, t, J=4.5), 5.98 (1H, brs), 6.64–7.58 (9H, m), 7.78 (1H, s)

M/Z 568 (M+H)⁺

Example 169

N-[6-Methanesulfonylamino-2-{3-(5-methyl-4-phenyl-1H-imidazol-1-yl)propoxy}]phenyl-N'-pentylurea

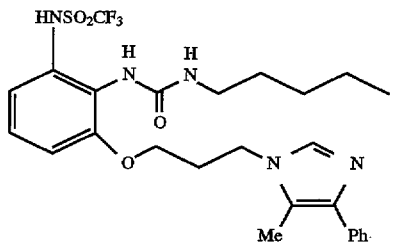

yield (%): 59 m.p. (° C.): 123 to 124

¹H-NMR (400 MHz, CDCl₃)

δ ppm=0.92 (3H, t, J=7.2), 1.24–1.57 (6H, m), 2.36 (2H, quintet, J=4.8), 2.38 (3H, s), 2.49 (3H, s), 3.15 (2H, q, J=7.2), 4.12 (2H, t, J=4.8), 4.20 (2H, t, J=4.8), 5.77 (1H, brs), 6.60–7.75 (10H, m), 8.82 (1H, brs)

M/Z 514 (M+H)

Example 170

N-[6-Methyl-2-[3-{4-(4-dimethanesulfonylamino)phenyl-1H-imidazol-1-yl}propoxy]]phenyl-N'-pentylurea

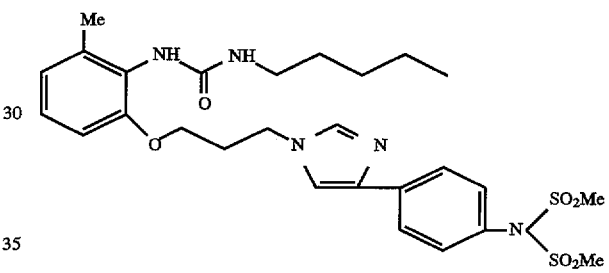

yield (%): 19 m.p. (° C.): 140 to 142

¹H-NMR (400 MHz, CDCl₃)

δ ppm=0.86 (3H, 5, J=7.0), 1.18–1.40 (6H, m), 2.22–2.30 (2Y, m), 2.31 (3Y, s), 3.20 (2H, m), 3.41 (6H, s), 3.80 (2H, t, J=7.2), 4.20 (2H, t, J=6.6), 4.59 (1H, brt), 5.85 (1H, brs), 6.68–7.82 (9H, m)

M/Z 592 (M+H)⁺

Example 171

N-[6-Methyl-2-[3-}4-(4-methanesulfonylamino)phenyl-1H-imidazol-1-yl}propoxy]]phenyl-N'-pentylurea

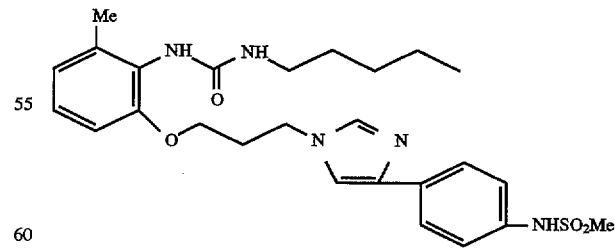

yield (%): 13 m.p. (° C.): 86 to 88

¹H-NMR (400 MHz, CDCl₃)

δ ppm=0.82 (3H, t, J=7.2), 1.16–1.29 (4H, m), 1.37–1.48 (2H, m), 2.13–2.26 (2H, m), 2.37 (3H, s), 2.90 (3H, s), 3.19 (2H, q, J=6.8), 3.88 (2H, t, J=5.4), 4.12 (2H, t, J=6.8), 4.94 (1H, brs), 6.41 (1H, brs), 6.66 (1H, d, J=8.0), 6.83 (1H, d, J=8.0), 7.08 (1H, t, J=8.0), 7.13 (1H, d, J=0.8), 7.20 (2H, d, J=8.8), 7.27 (1H, s), 7.50 (1H, d, J=0.8), 7.58 (2H, d, J=8.8)

M/Z 514 (M+H)$^+$

Example 172

N-[6-Methyl-2-[3-{4-(3-methanesulfonylamino)phenyl-1H-imidazol-1-yl}propoxy]]phenyl-N'-pentylurea yield (%): 40 m.p. (° C.): 165 to 167

$^1$H-NMR (400 MHz, DMSO)

δ ppm=0.84(3H, t, J=6.0, 1.20–1.50 (6H, m), 2.17 (2H, quintet, J=5.6), 2.19 (3H, s), 2.95 (3H, s), 3.08 (2H, q, J=6.0), 3.34 (3H, s), 3.85 (2H, t, J=5.6), 4.21 (2H, t, J=5.6), 6.25 (1H, brt), 6.74–7.65 (10H, m), 9.66 (1H, s)

M/Z 514 (M+H)$^+$

Example 173

N-[6-Methyl-2-{3-(5-methylthiomethyl-4-phenyl-1H-imidazol-1-yl)propoxy}]phenyl-N'-pentylurea 240 mg of sodium thiomethoxide was added to a dimethylformamide Solution of 520 mg of N-[6-methyl-2-{3-(5-chloromethyl-4-phenyl-1H-imidazol-1-yl)propoxy}] phenyl-N'-pentylurea. The obtained mixture was stirred at 100° C. for 30 minutes to conduct a reaction. After the completion of the reaction, the reaction mixture was extracted with ethyl acetate and the ethyl acetate layer was dried over magnesium sulfate and distilled to remove the solvent. The residue was purified by column chromatography and recrystallized from ethyl acetate to give 270 mg of the title compound.

yield (%): 51 m.p. (° C.): 128 to 130

$^1$H-NMR (400 MHz, CDCl$_3$)

δ ppm=0.86 (3H, t, J=7.2), 1.18–1.50 (6H, m), 1.98 (3H, s), 2.29 (3H, s), 2.34 (2H, quintet, J=6.0), 3.19 i2H, q, J=7.2), 3.88 (2H, s.), 4.01 (2H, t, J=6.0).4.27 (2H, t, J=6.0), 4.78 (1H, brt), 5.74 (1H, brs), 6.69–7.68 (9H, m)

M/Z 481 (M+H)$^+$

Example 174

N-[6-Methyl-2-[3-{4-(N,N-dimethylaminomethyl)-5-phenyl}propoxy]]phenyl-N'-pentylurea 0.2 cc of thionyl chloride and 0.38 cc of triethylamine were added to a chloroform solution of 800 mg of N-[6-methyl-2-{3-(4-hydroxymethyl-5-phenyl-1H-imidazol-1-yl)propoxy}]phenyl-N'-propylurea. The obtained mixture was heated under reflux for one hour to conduct a reaction. After the completion of the reaction, the solvent and excess reagents were distilled off to give N-[6-methyl-2-{3-(4-chloromethyl-5-phenyl-1H-imidazol-1-yl)propoxy}] phenyl-N'-pentylurea. 8 cc of dimethylamine was added to a solution of this product in dimethylformamide. The obtained mixture was stirred at room temperature for 2 hours and extracted with ethyl acetate. The ethyl acetate layer was dried over magnesium sulfate and distilled to remove the solvent. The residue was dissolved in toluene, followed by the addition of 500 mg of n-amylamine. The obtained mixture was heated under reflux for one hour and extracted with AcOEt. The AcOEt layer was dried over magnesium sulfate and distilled to remove the solvent. The residue was purified by column chromatography to give 460 mg of the title compound as an oil.

yield (%): 54 m.p. (° C.): oily substance $^1$H-NMR (400 MHz, CDCl$_3$)

δ ppm=0.86 (3H, t, J=6.8), 1.19–1.51 (6H, m), 2.14 (6H, s), 2.28 (3H, s), 2.31 (2H, quintet, J=6.0), 3.18 (2H, q, J=6.8), 3.56 (2H, s), 4.00 (2H, t, J=6.0), 4.32 (2H, t, J=6.0), 4.82 (1H, brt), 5.63 (1H, brs), 6.67–7.63 (9H, m)

M/Z 478 (M+H)$^+$

Example 175

N-[6-Methyl-2-{3-(4-carboxy-5-phenyl-1H-imidazol-1-yl) propoxy}]phenyl-N'-pentylurea 10 times (by equivalent)as much 10N sodium hydroxide was added to an ethanolic solution of 5.52 g of N-[6-methyl-2-{3-(4-carboethoxy-5-phenyl-1H-imidazol- 1-yl) propoxy}]phenyl-N'-pentylurea. The obtained mixture was stirred at room temperature for 5 hours to conduct a reaction. After the completion of the reaction, the reaction mixture was neutralized with concentrated hydrochloric acid and extracted with chloroform. The chloroform layer was dried over magnesium sulfate and distilled to remove the solvent. The precipitated crystal was washed with ether several times to give 5.07 g of the title compound.

yield (%): 98 m.p. (° C.): 131 to 132

¹H-NMR (400 MHz, CDCl₃)

δ ppm=0.82 (3H, t, J=7.6), 1.18–1.48 (6H, m), 2.21 (2H, quintet, J=5.6), 2.30 (3H, s), 3.16 (2H, t, J=7.6), 3.90 (2H, t, J=5.6), 4.00 (1H, brs), 4.51 (2H, t, J=5.6), 6.67–7.75 (11H, m)

M/Z 465 (M+H)⁺

Example 176

N-[6-Methyl-2-{3-(4-carbamoyl-5-phenyl-1H-imidazol-1-yl)propoxy}]phenyl-N'-pentylurea

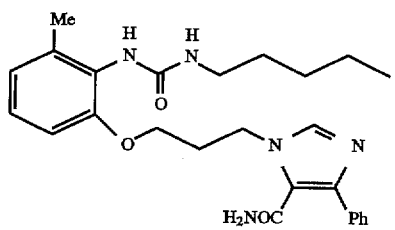

0.071 cc of thionyl chloride was added to a methylene chloride solution of 300 mg of N-[6-methyl-2-{3-(4-carboxy-5-phenyl-1H-imidazol-1-yl)propoxy}]-phenyl-N'-pentylurea. The obtained mixture was heated under reflux for one hour and distilled to remove the solvent and excess thionyl chloride. The residue was dissolved in chloroform and 10 times by equivalent as much aqueous ammonia was dropped into the chloroform solution under cooling with ice. The obtained mixture was vigorously stirred to conduct a reaction. After the completion of the reaction, the reaction mixture was extracted with ethyl acetate and the ethyl acetate layer was dried over magnesium sulfate and distilled to remove the solvent. The residue was recrystallized from ethyl acetate to give 280 mg of the title compound.

yield (%): 93 m.p. (° C.): 176 to 177

¹H-NMR (400 MHz, CDCl₃)

δ ppm=0.84 (3H, t, J=7.2), 1.18–1.50 (6H, m), 2.27 (2H, quintet, J=6.0), 2.30 (3H, s), 3.17 (2H, q, J=7.2), 3.97 (2H, .t, J=6.0), 4.56 (2H, t, J=6.0), 4.80 (1H, brt), 5.97 (1H,. brs), 6.02 (1H, brs), 6.45 (1H, brs), 6.69–7.64 (9H, m)

M/Z 464 (M+H)⁺

Example 177

N-[6-Amino-2-{3-(5-methyl-4-phenyl-1H-imidazol-1-yl)propoxy}]phenyl-N'-pentylurea

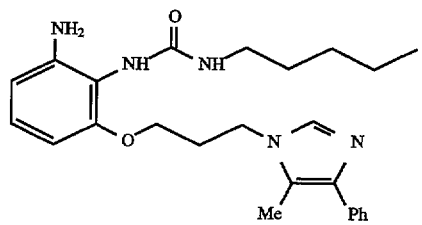

A catalytic amount of palladium-carbon was added to a solution of 5 g of N-[6-nitro-2-{3-(5-methyl-4-phenyl-1H-imidazol-1-yl)propoxy}]phenyl-N'-pentylurea in an ethanol/acetic acid mixture. The obtained mixture was refluxed in a hydrogen stream of 5 atm to conduct a reaction. After the completion of the reaction, the reaction mixture was concentrated and extracted with chloroform. The chloroform layer was washed with a saturated solution of sodium hydrogen-carbonate. The chloroform layer was concentrated to precipitate a crystal. This crystal was recrystallized from ethyl acetate to give 3.86 g of the title compound.

yield (%): 83 m.p. (° C.): 86 to 87

¹H-NMR (400 MHz, CDCl₃)

δ ppm=0.86 (3H, t, J=7.2), 1.22–1.46 (6H, m), 2.23 (2H, quintet, J=6.0), 2.39 (3H, s), 3.15 (2H, q, J=7.2), 3.96 (2H, t, J=6.0), 4.13 (2H, t, J=6.0), 5.15 (1H, brt), 5.56 (1H, brs), 6.23–7.64 (9H, m)

M/Z 436 (M+H)⁺

Example 178

N-[6-Methyl-2-{3-(5-ethyl-4-phenyl-1H-imidazol-1-yl)-propoxy}]phenyl-N'-butylurea

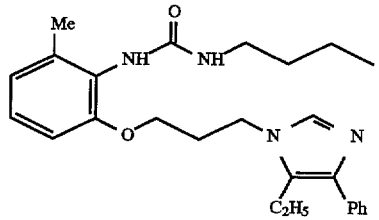

(1) synthesis of 6-methyl-2-(3-chloropropoxy) nitrobenzene or 2-(3-chloropropoxy)-6-methyl-nitrobenzene

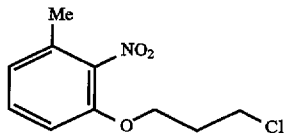

90.3 g of potassium carbonate was added to a solution of 50 g of 3-methyl-2-nitrophenol and 51.5 g of 1-bromo-3-chloropropane in 300 cc of dimethylform-amide. The obtained mixture was stirred at 60° C. under heating for 2 hours to conduct a reaction. After the completion of the reaction, the reaction mixture was extracted with ethyl acetate and the ethyl acetate layer was dried over magnesium sulfate and concentrated to give 73.82 g of the title compound as an oil (yield: 98%).

(2) synthesis of 6-methyl-2-(3-N-formylaminopropoxy)-nitrobenzene or 2-(3-N-formylaminopropoxy)-6-methyl-nitrobenzene

101

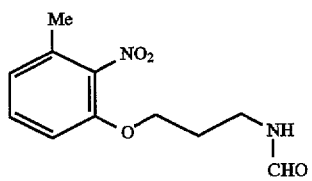

A dimethylformamide solution of 63.82 g of 2-(3-chloropropoxy)-6-methyl-nitrobenzene prepared in the item (1), 31.7 g of sodium diformamide and 4.17 g of sodium iodide was stirred under heating at 100° C. for one hour to conduct a reaction. After the completion of the reaction, the reaction mixture was extracted with ethyl acetate and the ethyl acetate layer was dried over magnesium sulfate and distilled to remove the solvent. The residue was recrystallized from ethanol to give 66.80 g of 2-(3-N,N-diformylamino-propoxy)-6-methyl-nitrobenzene (yield: 90%). The product was dissolved in ethanol followed by the addition of 300 mg of potassium hydroxide. The obtained mixture was stirred at room temperature for 10 minutes to conduct a reaction. After the completion of the reaction, the reaction mixture was extracted with ethyl acetate and the ethyl acetate layer was dried over magnesium sulfate and distilled to remove the solvent. The obtained crystal was washed with ether and hexane to give 51.19 g of the title compound (yield: 86%).

(3) synthesis of 6-methyl-2-{3-(5-ethyl-4-phenyl-1H-imidazol-1-yl)propoxy}nitrobenzene

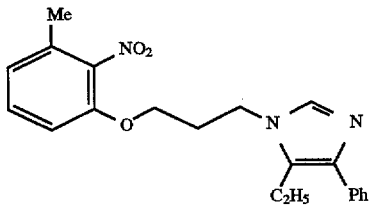

3.67 g of sodium hydride was added to a dimethylformanide solution of 20 g of 2-(3-N-formylaminopropoxy)-6-methyl-nitrobenzene prepared in the item (2). The obtained mixture was stirred under heating at 60° C. for one hour and dropped into a solution of 2-bromobutyrophenone in dimethylformamide over a period of one hour. After the completion of the dropping, the obtained mixture was stirred for one hour and extracted with ethyl acetate. The ethyl acetate layer was dried over magnesium sulfate and distilled to remove the solvent. 6.65 g of ammonium formate, 1.6 g of formic acid and 2.1 g of formamide were added to the obtained oil and the obtained mixture was stirred under heating at 120° C. for 2 hours to conduct a reaction, followed by the addition of ether and water. The obtained mixture was vigorously stirred for 15 minutes and allowed to stand at 0° C. for one hour to precipitate a crystal. This crystal was recovered by filtration and washed with water and ether to give 8.2 g of the title compound (yield: 27%).

¹H-NMR (400 MHz, CDCl₃)

δ ppm=1.22 (3H, t, J=7.2), 2.18 (2H, quintet, J=6.5), 2.34 (3H, s), 2.78 (2H, q, J=7.2), 3.98 (2H, t, J=6.5), 4.07 (2H, t, J=6.5), 6.76–7.63 (9H, m)

M/Z 366 (M+H)⁺

(4) synthesis of 2-{3-(5-ethyl-4-phenyl-1H-imidazol-1-yl) propoxy}-6-methyl aniline

102

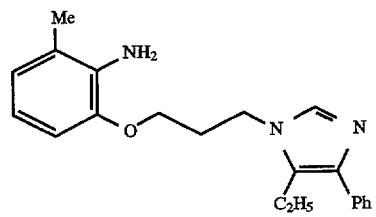

300 mg of 10% palladium-carbon was added to a solution of 8.2 g of 6-methyl-2-{3-(5-ethyl-4-phenyl-1H-imidazol-1-yl)propoxy}nitrobenzene prepared in the item (3) in an ethyl acetate/ethanol mixture to conduct reduction in a hydrogen stream. After the completion of the reduction, the reaction mixture was filtered and the filtrate was distilled to remove the solvent. Thus, 6.36 g of the title compound was obtained as an oil (yield: 85%).

¹H-NMR (400 MHz, CDCl₃)

δ ppm=1.23 (3H, t, J=7.2), 2.18 (3H, s), 2.36 (2H, quintet, J=6.5), 2.81 (2H, q, J=7.2), 4.10 (2H, t, J=6.5), 4.23 (2H, t, J=6.5), 4.30–4.60 (2H, m), 6.62–7.63 (8H, m), 8.06 (1H, brs)

M/Z 336 (M+H)⁺

(5) synthesis of N-[6-methyl-2-{3-(5-ethyl-4-phenyl-1H-imidazol-1-yl)propoxy}]phenyl-N'-butylurea or N-[2-{3-(5-ethyl-4-phenyl-1H- imidazol-1-yl)propoxy}-6-methyl] phenyl-N'-butylurea

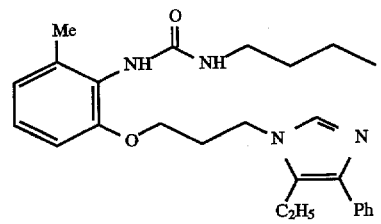

1.90 g of butyl isocyanate was dropped into a chloroform solution of 6.36 g of 6-methyl-2-{3-(5-ethyl-4-phenyl-1H-imidazol-1-yl)propoxy}aniline prepared in the item (4). The obtained mixture was heated under reflux for 24 hours to conduct a reaction. After the completion of the reaction, the reaction mixture was concentrated and recrystallized from ethyl acetate/hexane to give 8.21 g of the title compound (yield: 100%).

The melting point, ¹H-NMR (400 MHz, CDCl₃) and M/Z of this product were the same as those of the compound of Example 81.

The same compounds as those prepared in the foregoing Examples 80, 82, 84 and 127 can be prepared in a similar manner to that of Example 178.

We claim:

1. A benzene compound represented by the general formula (I):

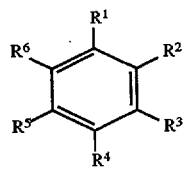

wherein $R^1$ stands for a halogen atom, a lower alkyl, a lower alkoxy, a nitro or a cyano group, a group represented by the formula:

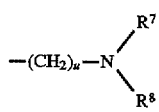

wherein $R^7$ and $R^8$ may be the same or different and each stands for a hydrogen atom, a lower alkyl or a lower alkylsulfonyl group, and u is 0 or an integer of 1 or 2 or alternatively, $R^7$ and $R^8$ may form a ring together with the nitrogen atom to which $R^7$ and $R^8$ are bonded, a group represented by the formula: —$CH_2OR^9$ wherein $R^9$ stands for a hydrogen atom or a lower alkyl group, a group represented by the formula: —$COOR^{10}$ wherein $R^{10}$ stands for a hydrogen atom or a lower alkyl group, a group represented by the formula:

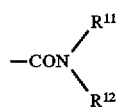

wherein $R^{11}$ and $R^{12}$ may be the same or different and each stands for a hydrogen atom or a lower alkyl group or a group represented by the formula:

wherein t is 0 or an integer of 1 or 2; and $R^{13}$ stands for a hydrogen atom or a lower alkyl group;

$R^2$ stands for a group represented by the formula:

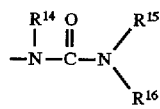

wherein $R^{14}$, $R^{15}$ and $R^{16}$ may be the same or different and each stands for a hydrogen atom or an alkyl, cycloalkyl, alkenyl or alkyloxyalkyl group; alternatively, $R^{15}$ and $R^{16}$ may form a ring together with the nitrogen atom to which $R^{15}$ and $R^{16}$ are bonded, a group represented by the formula: —NH—$R^{18}$ wherein $R^{18}$ stands for an alkyl group or a group represented by the formula:

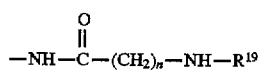

wherein $R^{19}$ stands for an alkyl group and n is an integer of 1 to 3;

$R^3$ stands for a group represented by the formula: —$(CH_2)_p$—X— $(CH_2)_m$—Y wherein X stands for a group represented by the formula: —O—, —S—,

—$SO_2$—, —NH—, —$CH_2$— or —CH=CH—; p is 0 or 1; m is an integer of 1 to 6; Y is selected from the group consisting of

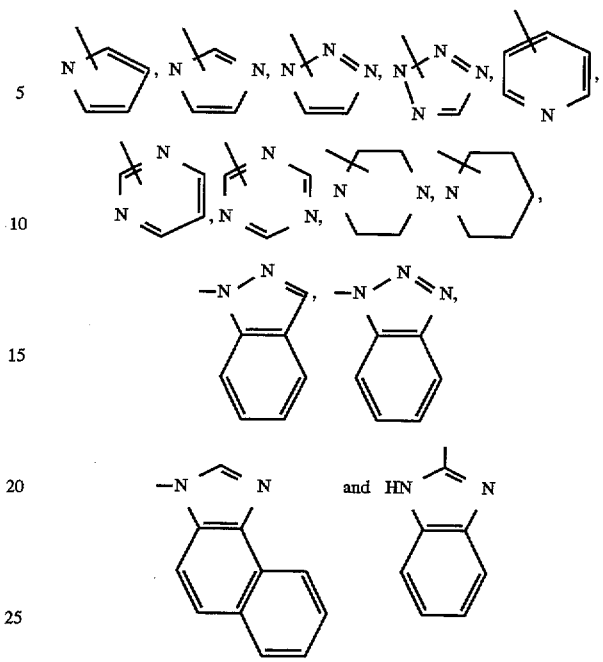

which may have a substituent (s), said substituent (s) for Y being a (a) $C_1$-$C_6$ lower alkyl group, (b) a $C_1$-$C_6$ lower alkoxy group, an aryl group or an aryl group substituted with a substituent(s) selected from a $C_1$-$C_6$ lower alkyl group, a $C_1$-$C_6$ lower alkoxy group, $C_1$-$C_6$ lower alkylsulfonyl group, a halogen atom, a nitro group, a $C_1$-$C_6$ lower alkylsulfonylamino group, or a di ($C_1$-$C_6$ lower alkyl)sulfonylamino group, (c) a group represented by the formula: —$(E)_a$—$COOR^{21}$ wherein E is a $C_1$-$C_6$ alkylene or $C_1$-$C_6$ alkenylene group, and $R^{21}$ is an H atom, a lower alkyl group, or an amino group, and a is 0 or 1, (d) a group represented by the formula: —$(CH_2)_v$—OH wherein v is 0 or an integer of 1 to 6, (e) a halogen atom, (f) a group represented by the formula: —$(CH_2)_b$—NH—$(CH_2)_c$—$CH_3$ wherein b is 0 or an integer of 1 to 4 and c is 0 or an integer of 1 to 5, (g) a group represented by the formula: —$(CH_2)_d$—$SO_2$$R^{22}$ wherein d is 0 or an integer of 1 to 6 and $R^{22}$ is a $C_1$-$C_6$ lower alkyl group, or (h) a group represented by the formula:

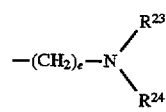

wherein e is an integer of 1 to 6, and $R^{23}$ and $R^{24}$ may be the same or different and each stands for a hydrogen or a $C_1$-$C_6$ lower alkyl or Y is a $C_1$-$C_6$ lower alkoxy group or a group represented by the formula:

$$-V-(CH_2)_q-\underset{\underset{OR^{20}}{|}}{CH}-(CH_2)_s-W$$

W wherein V stands for a group represented by the formula: —O—, —S—, $$-\overset{O}{\underset{\|}{S}}-,$$

—SO$_2$—, —NH— or —CH$_2$—; q and s are each an integer of 1 to 6; R$^°$ stands for a hydrogen atom or a lower alkyl group; W has the same definition as Y above;

R$^6$ stands for a hydrogen atom;

R$^4$ stands for a hydrogen;

R$^5$ stands for a hydrogen atom;

or a pharmacologically acceptable salt thereof.

2. The compound as claimed in claim 1, or a pharmacologically acceptable salt, which is a compound represented by the general formula:

[chemical structure: benzene ring with R$^1$ substituent, NH—C(=O)—NH—R$^{16}$ group, and O—(CH$_2$)$_m$—Y group]

wherein R$^1$ stands for a lower alkyl or a group represented by the formula: —NR$^7$R$^8$, wherein R$^7$ and R$^8$ may be the same or different and each stands for a hydrogen atom or a lower alkyl group, R$^{16}$ stands for a hydrogen atom, alkyl, cyctoalkyl, alkenyl or alkyloxyalkyl group, m is an integer of 1 to 6: and Y is selected from the group consisting of

[chemical structures of heterocyclic groups]

which may have a substituent(s), said above substituent(s) for Y being (a) C$_1$-C$_6$ lower alkyl group, (b) a C$_1$-C$_6$ lower alkoxy group, an aryl group or an aryl group substituted with a substituent (s) selected from a C$_1$-C$_6$ lower alkyl group, a C$_1$-C$_6$ lower alkoxy group, C$_1$-C$_6$ lower alkylsulfonyl group, a halogen atom, a nitro group, a C$_1$-C$_6$ lower alkylsulfonylamino group, or a di(C$_1$-C$_6$ lower alkyl)sulfonylamino group, (c) a group represented by the formula: —(E)$_a$—COOR$^{21}$ wherein E is a C$_1$-C$_6$ alkylene or C$_1$-C$_6$ alkenylene group, and R$^{21}$ is an H atom, a lower alkyl group, or an amino group, and a is 0 or 1, (d) a group represented by the formula: —(CH$_2$)$_v$—OH wherein v is 0 or an integer of 1 to 6, (e) a halogen atom, (f) a group represented by the formula: —(CH$_2$)$_b$—NH—(CH$_2$)$_c$—CH$_3$ wherein b is 0 or an integer of 1 to 4 and c is 0 or an integer of 1 to 5, (g) a group represented by the formula: —(CH$_2$)$_d$—SO$_2$R$^{22}$ wherein d is 0 or an integer of 1 to 6 and R$^{22}$ is a C$_1$-C$_6$ lower alkyl group, or (h) a group represented by the formula:

$$-(CH_2)_e-N\underset{R^{24}}{\overset{R^{23}}{\diagup}}$$

wherein e is an integer of 1 to 6, and R$^{23}$ and R$^{24}$ may be the same or different and each stands for a hydrogen or a C$_1$-C$_6$ lower alkyl or a C$_1$-C$_6$ lower alkoxy group.

3. The compound or a pharmacologically acceptable salt thereof as claimed in claim 2 wherein R$^1$ is methyl group.

4. The compound or a pharmacologically acceptable salt thereof as claimed in claim 2, wherein R$^1$ is dimethylamino group.

5. The compound or a pharmacologically acceptable salt thereof as claimed in claim 2, wherein R$^{16}$ is an alkyl group having 1 to 6 carbon atoms.

6. The compound or a pharmacologically acceptable salt thereof as claimed in claim 2, wherein R$^{16}$ is an alkyl group having 2 to 4 carbon atoms.

7. The compound or a pharmacologically acceptable salt thereof as claimed in claim 2, wherein Y is imidazolyl group which may be substituted.

8. The compound or a pharmacologically acceptable salt thereof as claimed in claim 2, wherein Y is imidazolyl group which may be substituted by a lower alkyl group, a halogen atom or phenyl group.

9. The compound or a pharmacologically acceptable salt thereof as claimed in claim 2, wherein Y is a di-substituted imidazolyl group whose substituents are selected from the group consisting of lower alkyl groups having 1 to 6 carbon atoms, halogen atoms and phenyl group.

10. The compound or a pharmacologically acceptable salt thereof as claimed in claim 2, wherein R$^1$ is methyl, R$^{16}$ is an alkyl group having 1 to 6 carbon atoms, M is an integer of 1 to 6 and Y is an imidazolyl group which may have a substituent(s).

11. The compound or a pharmacologically acceptable salt thereof as claimed in claim 2, wherein R$^1$ is methyl, R$^{16}$ is an alkyl group having 2 to 4 carbon atoms, M is an integer of 1 to 6 and Y is an imidazolyl group which may have one or more substituents selected from the group consisting of a lower alkyl group having 1 to 6 carbon atoms, a halogen atom and phenyl group.

12. The compound or a pharmacologically acceptable salt thereof as claimed in claim 2, wherein Y is piperazinyl group which may be substituted.

13. A benzene derivative which is N-[2-{3-(5-ethyl-4-phenyl-1H-imidazole-1-yl)propoxy}-6-methyl]phenyl-N'-butylurea and has the formula:

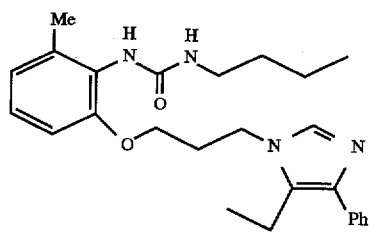

or a pharmacologically acceptable salt thereof.

14. A compound or a pharmacologically acceptable salt thereof which is selected from the group consisting of:

N-[6-N,N-Dimethylamino-2-{3-(4-phenyl-1H-imidazol-1-yl)propoxy}]phenyl-N'-pentylurea

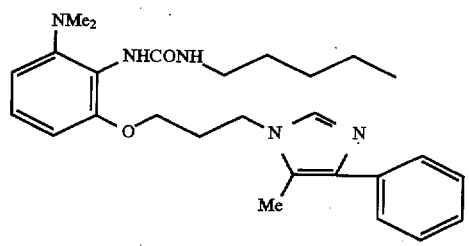

N-[6-N,N-Dimethylamino-2-{3-(4-phenyl-1H-imidazol-1-yl)propoxy}]phenyl-N'-butylurea

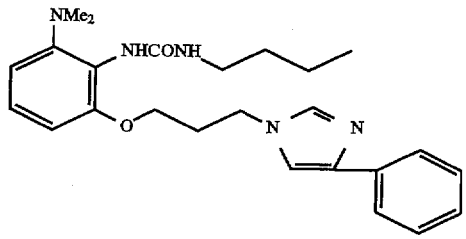

N-[6-N,N-Dimethylamino-2-{3-(5-methyl-4-phenyl-1H-imidazol-1-yl)propoxy}]phenyl-N'-butylurea

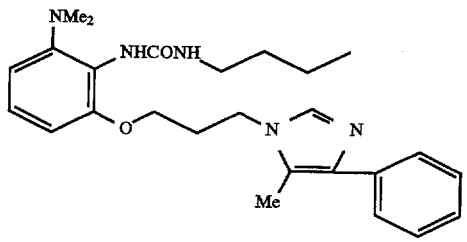

N-[6-N,N-Dimethylamino-2-{3-(4-phenyl-1H-imidazol-1-yl)propoxy}]phenyl-N'-hexylurea

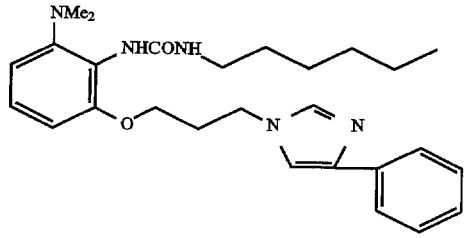

-continued
N-[6-{4-(4-Phenyl-1H-imidazol-k-yl)butyl}-2-N,N-dimethylamino]phenyl-N'-butylurea

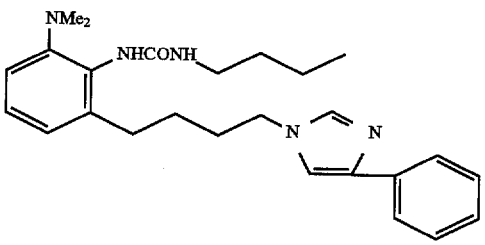

N-[6-methyl-2-{3-(4-phenyl-1H-imidazol-1-yl)propoxy}]pheyl-N-butylurea

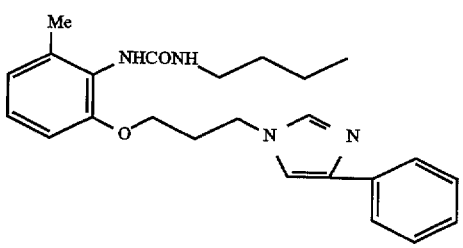

N-[6-N,N-Dimethylamino-2-{3-(4-phenylpiperazin-1-yl)propoxy}]phenyl-N'-pentylurea

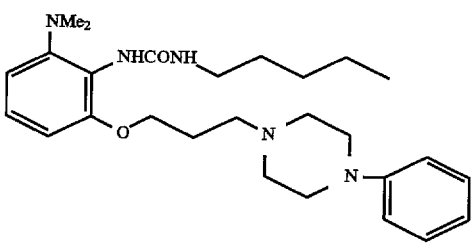

N-[6-methyl-2-[3-{-(1-methylethyl)-4-phenyl-1H-imidazol-1-yl)propoxy}]phenyl-N'-buthylurea

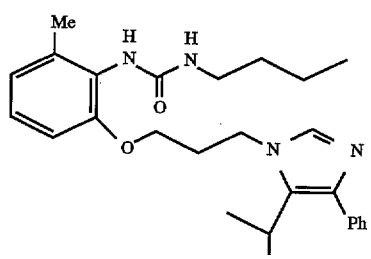

N-[6-Methyl-2-{3-(5-chloro-4-phenyl-1H-imidazol-1-yl)propoxy}]phenyl-N'-pentylurea

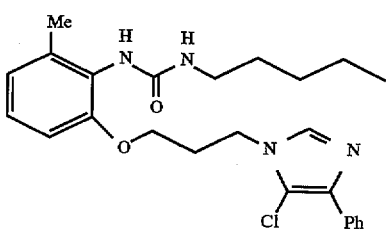

-continued

N-[6-Methyl-2-{3-(5-methyl-4-phenyl-1H-imidazol-1-yl)-propoxy}]phenyl-N'-pentylurea

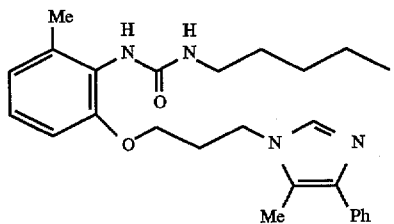

N-[6-Ethyl-2-{3-(5-methyl-4-phenyl-1H-imidazol-1-yl)-propoxy}phenyl-N'-pentylurea

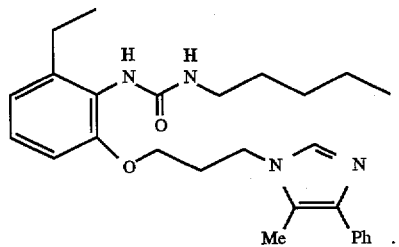

15. A benzene compound represented by the general formula:

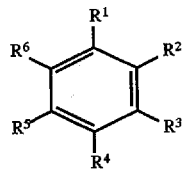

wherein $R^1$ stands for a halogen atom, a lower alkyl, a lower alkoxy, a nitro or a cyano group, a group represented by the formula:

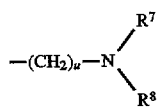

wherein $R^7$ and $R^8$ may be the same or different and each stands for a hydrogen atom, a lower alkyl or a lower alkylsulfonyl group, and u is 0 or an integer of 1 or 2 or alternatively, $R^7$ and $R^8$ may form a ring together with the nitrogen atom to which $R^7$ and $R^8$ are bonded, a group represented by the formula: —$CH_2OR^9$ wherein $R^9$ stands for a hydrogen atom or a lower alkyl group, a group represented by the formula: —$COOR^{10}$ wherein $R^{10}$ stands for a hydrogen atom or a lower alkyl group, a group represented by the formula:

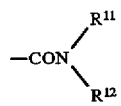

wherein $R^{11}$ and $R^{12}$ may be the same or different and each stands for a hydrogen atom or a lower alkyl group or a group represented by the formula:

wherein t is 0 or an integer of 1 or 2; and $R^{13}$ stands for a hydrogen atom or a lower alkyl group;

$R^2$ stands for a group represented by the formula:

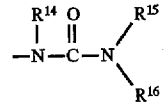

wherein $R^{14}$ stands for a hydrogen atom or an alkyl, cycloalkyl, alkenyl or alkyloxyalkyl group; $R^{15}$ stands for a hydrogen atom or an alkyl, cycloalkyl, alkenyl or alkyloxyalkyl group; and $R^{16}$ stands for alkyl, cycloalkyl, alkenyl or alkyloxyalkyl group; or $R^{15}$ and $R^{16}$ may form a ring together with the nitrogen atom to which $R^{15}$ and $R^{16}$ are bonded, or $R^2$ stands for a group represented by the formula: —NH—$R^{18}$ wherein $R^{18}$ stands for an alkyl group or a group represented by the formula:

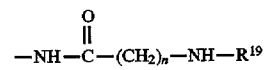

wherein $R^{19}$ stands for an alkyl group and n is an integer of 1 to 3;

$R^3$ stands for a group represented by the formula: —$(CH_2)_p$—X—$(CH_2)_m$—Y wherein X stands for a group represented by the formula: —O—, —S—,

—$SO_2$—, —NH—, —$CH_2$— or —CH=CH—; p is 0 or 1; m is an integer of 1 to 6; Y is selected from the group consisting of

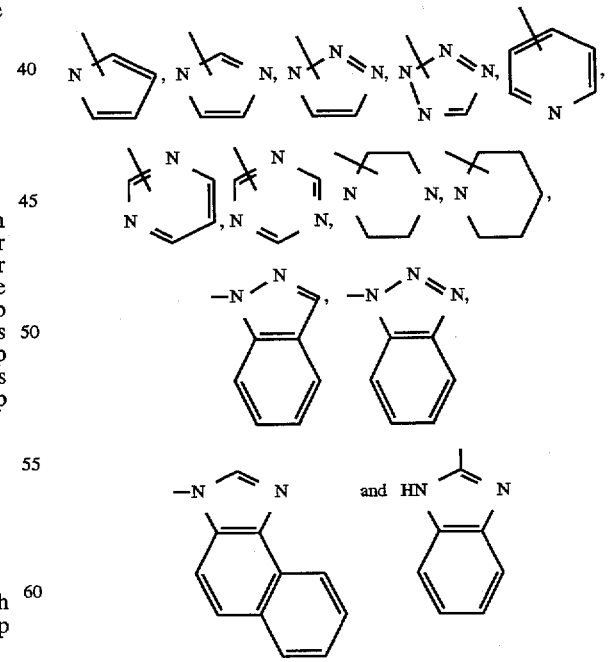

which may have a substituent (s), said substituent (s) for Y being a (a) $C_1$–$C_6$ lower alkyl group, (b) a $C_1$-$C_6$ lower alkoxy group, an aryl group or an aryl group substituted with a substituent(s) selected from a $C_1$-$C_6$ lower alkyl group, a $C_1$-$C_6$ lower alkoxy group, $C_1$-$C_6$ lower alkylsulfonyl group, a halogen atom, a nitro group, a $C_1$-$C_6$ lower alkylsulfonylamino group, or a di ($C_1$-$C_6$ lower alkyl) sulfonylamino group, (c) a group represented by the formula: —$(E)_a$—$COOR^{21}$ wherein E is a $C_1$-$C_6$ alkylene or $C_1$-$C_6$ alkenylene group, and $R^{21}$ is an H atom, a lower alkyl group, or an amino group, and a is 0 or 1, (d) a group represented by the formula: —$(CH_2)_v$—OH wherein v is 0 or an integer of 1 to 6, (e) a halogen atom, (f) a group represented by the formula: —$(CH2)_b$—NH—$(CH_2)_c$—$CH_3$ wherein b is 0 or an integer of 1 to 4 and c is 0 or an integer of 1 to 5, (g) a group represented by the formula: —$(CH_2)_a$—$SO_2R^{22}$ wherein d is 0 or an integer of 1 to 6 and $R^{22}$ is a $C_1$-$C_6$ lower alkyl group, or (h) a group represented by the formula:

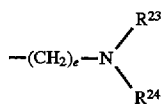

wherein e is an integer of 1 to 6, and $R^{23}$ and $R^{24}$ may be the same or different and each stands for a hydrogen or a $C_1$-$C_6$ lower alkyl or Y is a $C_1$-$C_6$ lower alkoxy group or a group represented by the formula:

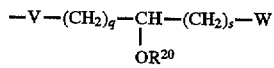

wherein V stands for a group represented by the formula: —O—, —S—,

—$SO_2$—, —NH— or —$CH_2$—; q and s are each an integer of 1 to 6; R stands for a hydrogen atom or a lower alkyl group; W has the same definition as Y above;

$R^6$ stands for a hydrogen atom;

$R^4$ stands for a hydrogen;

$R^5$ stands for a hydrogen atom; and in addition, two of $R^1$, $R^4$, $R^5$ and $R^6$ may form a benzene ring, which may be substituted;

or a pharmacologically acceptable salt thereof.

16. A benzene compound represented by the general formula:

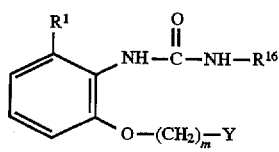

wherein $R^1$ stands for a lower alkyl, or a group represented by the formula:

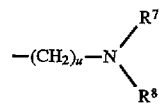

(wherein $R^7$ and $R^8$ may be the same or different and each stands for a hydrogen atom, or a lower alkyl and u is 0 or an integer of 1 or 2;

$R^{16}$ stands for a hydrogen atom or an alkyl, cycloalkyl, alkenyl or alkyloxyalkyl group;

m is an integer of 1 to 6; Y is selected from the group consisting of

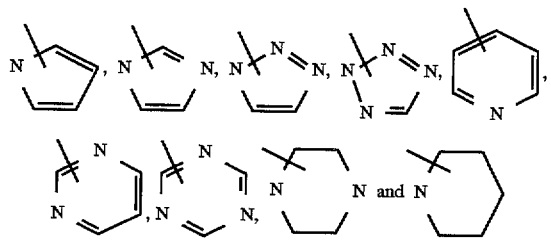

which may have a substituent (s), said substituent (s) for Y being a (a) $C_1$-$C_6$ lower alkyl group, (b) a $C_1$-$C_6$ lower alkoxy group, an aryl group or an aryl group substituted with a substituent(s) selected from a $C_1$-$C_6$ lower alkyl group, a $C_1$-$C_6$ lower alkoxy group, $C_1$-$C_6$ lower alkylsulfonyl group, a halogen atom, a nitro group, a $C_1$-$C_6$ lower alkylsulfonylamino group, or a di ($C_1$-$C_6$ lower alkyl)sulfonylamino group, (c) a group represented by the formula: —$(E)_a$—$COOR^{21}$ wherein E is a $C_1$-$C_6$ alkylene or $C_1$-$C_6$ alkenylene group, and $R^{21}$ is an H atom, a lower alkyl group, or an amino group, and a is 0 or 1, (d) a group represented by the formula: —$(CH_2)_v$—OH wherein v is 0 or an integer of 1 to 6, (e) a halogen atom, (f) a group represented by the formula: —$(CH_2)_b$—NH—$(CH_2)_c$—$CH_3$ wherein b is 0 or an integer of 1 to 4 and c is 0 or an integer of 1 to 5, (g) a group represented by the formula: —$(CH_2)_a$—$SO_2R^{22}$ wherein d is 0 or an integer of 1 to 6 and $R^{22}$ is a $C_1$-$C_6$ lower alkyl group, or (h) a group represented by the formula:

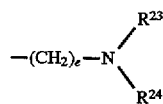

wherein e is an integer of 1 to 6, and $R^{23}$ and $R^{24}$ may be the same or different and each stands for a hydrogen or a $C_1$-$C_6$ lower alkyl or Y is a group represented by the formula:

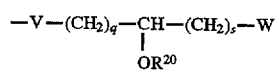

wherein V stands for a group represented by the formula: —O—, —S—,

—SO$_2$—, —NH— or —CH$_2$—; q and s are each an integer of 1 to 6; R$^{20}$ stands for a hydrogen atom or a lower alkyl group; W has the same definition as Y above; or a pharmacologically acceptable salt thereof.

17. A benzene compound represented by the general formula:

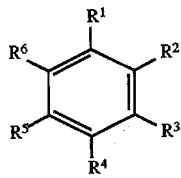

wherein R$^1$ stands for a halogen atom, a lower alkyl, a lower alkoxy, a nitro or a cyano group, a group represented by the formula:

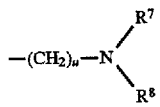

wherein R$^7$ and R$^8$ may be the same or different and each stands for a hydrogen atom, a lower alkyl or a lower alkylsulfonyl group, and u is 0 or an integer of 1 or 2 or alternatively, R$^7$ and R$^8$ may form a ring together with the nitrogen atom to which R$^7$ and R$^8$ are bonded, a group represented by the formula: —CH$_2$OR$^9$ wherein R$^9$ stands for a hydrogen atom or a lower alkyl group, a group represented by the formula: —COOR$^{10}$ wherein R$^{10}$ stands for a hydrogen atom or a lower alkyl group, a group represented by the formula:

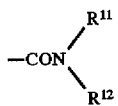

wherein R$^{11}$ and R$^{12}$ may be the same or different and each stands for a hydrogen atom or a lower alkyl group or a group represented by the formula:

wherein t is 0 or an integer of 1 or 2; and R$^{13}$ stands for a hydrogen atom or a lower alkyl group;

R$^2$ stands for a group represented by the formula:

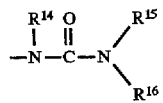

wherein R$^{14}$, R$^{15}$ and R$^{16}$ may be the same or different and each stands for a hydrogen atom or an alkyl, cycloalkyl, alkenyl or alkyloxyalkyl group;

R$^3$ stands for a group represented by the formula: —(CH$_2$)$_p$—X— (CH$_2$)$_m$—Y wherein X stands for a group represented by the formula: —O—, —S—,

—SO$_2$—, —NH—, —CH$_2$— or —CH=CH—; p is 0 or 1; m is an integer of 1 to 6; and Y is selected from the group consisting of

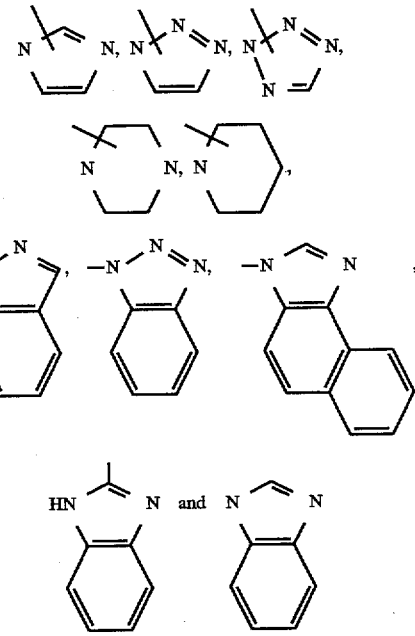

which may have a substituent (s), said substituent (s) for Y being a (a) C$_1$–C$_6$ lower alkyl group,
(b) a C$_1$–C$_6$ lower alkoxy group, an aryl group or an aryl group substituted with a substituent (s) selected from a C$_1$–C$_6$ lower alkyl group, a C$_1$–C$_6$ lower alkoxy group, C$_1$–C$_6$ lower alkylsulfonyl group, a halogen atom, a nitro group, a C$_1$–C$_6$ lower alkyl sulfonylamino group, or a di (C$_1$–C$_6$ lower alkyl) sulfonylamino group,
(c) a group represented by the formula: —(E)$_a$—COOR$^{21}$ wherein E is a C$_1$–C$_6$ alkylene or C$_1$–C$_6$ alkenylene group, and R$^{21}$ is an H atom, a lower alkyl group, or an amino group, and a is 0 or 1,
(d) a group represented by the formula: —(CH$_2$)$_v$—OH wherein v is 0 or an integer of 1 to 6,
(e) a halogen atom,
(f) a group represented by the formula: —(CH$_2$)$_b$—NH— (CH$_2$)$_c$—CH$_3$ wherein b is 0 or an integer of t to 4 and c is 0 or an integer of 1 to 5,
(g) a group represented by the formula: —(CH$_2$)$_d$— SO$_2$R$^{22}$ wherein d is 0 or an integer of 1 to 6 and R$^{22}$ is a C$_1$–C$_6$ lower alkyl group, or
(h) a group represented by the formula:

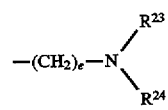

wherein e is an integer of 1 to 6, and R$^{23}$ and R$^{24}$ may be the same or different and each stands for a hydrogen or a C$_1$–C$_6$ lower alkyl or Y is a $C_1$-$C_6$ lower alkoxy group or a group represented by the formula:

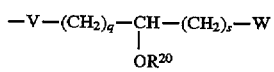

wherein V stands for a group represented by the formula: —O—, —S—,

—SO$_2$—, —NH— or —CH$_2$—; q and s are each an integer of 1 to 6; $R^{20}$ stands for a hydrogen atom or a lower alkyl group; W has the same definition as Y above;

$R^6$ stands for a hydrogen atom;

$R^4$ stands for a hydrogen;

$R^5$ stands for a hydrogen atom;

or a pharmacologically acceptable salt thereof.

18. A pharmaceutical composition which comprises an effective amount of a benzene compound or a pharmacologically acceptable salt thereof as set forth in claim 14, and a pharmacologically acceptable carrier.

19. A benzene derivative represented by the general formula:

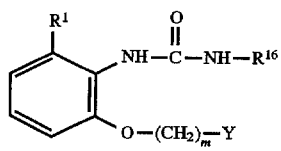

wherein $R^1$ stands for a group represented by the formula: —NR$^7$R$^8$, wherein $R^7$ and $R^8$ each stands for a hydrogen atom or a lower alkyl group, $R^{16}$ stands for a hydrogen atom, alkyl, cycloalkyl, alkenyl or alkyloxyalkyl group, m is an integer of 1 to 6: and Y is

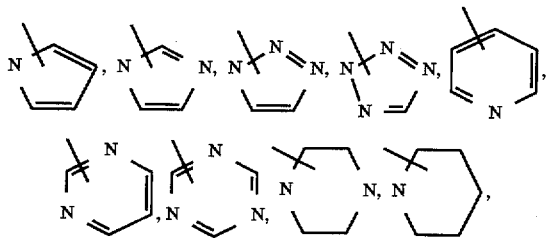

or a group selected from

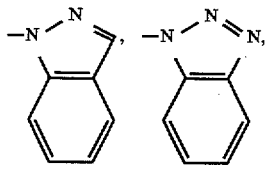

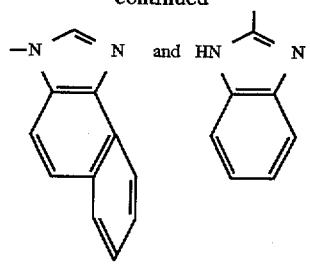

which may have a substituent(s), said above substituent(s) for Y being a (a) $C_1$-$C_6$ lower alkyl group, (b) a $C_1$-$C_6$ lower alkoxy group, an aryl group or an aryl group substituted with a substituent(s) selected from a $C_1$-$C_6$ lower alkyl group, a $C_1$-$C_6$ lower alkoxy group, $C_1$-$C_6$ lower alkylsulfonyl group, a halogen atom, a nitro group, a $C_1$-$C_6$ lower alkylsulfonylamino group, or a di($C_1$-$C_6$ lower alkyl)sulfonylamino group, (c) a group represented by the formula: —(E)$_a$—COOR$^{21}$ wherein E is a $C_1$-$C_6$ alkylene or $C_1$-$C_6$ alkenylene group, and $R^{21}$ is an H atom, a lower alkyl group, or an amino group, and a is 0 or 1, (d) a group represented by the formula: —(CH$_2$)$_v$—OH (wherein v is 0 or an integer of 1 to 6), (e) a halogen atom, (f) a group represented by the formula: —(CH$_2$)$_b$—NH—(CH$_2$)$_c$—CH$_3$ (wherein b is 0 or an integer of 1 to 4 and c is 0 or an integer of 1 to 5), (g) a group represented by the formula: —(CH$_2$)$_d$—SO$_2$R$^{22}$ (wherein d is 0 or an integer of 1 to 6 and $R^{22}$ is a $C_1$-$C_6$ lower alkyl group), or (h) a group represented by the formula:

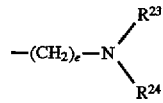

(wherein e is an integer of 1 to 6, and $R^{23}$ and $R^{24}$ may be the same or different and each stands for a hydrogen or a $C_1$-$C_6$ lower alkyl) or a $C_1$-$C_6$ lower alkoxy group; or a pharmacologically acceptable salt thereof.

20. A method for the treatment of diseases associated with cholesterol O-acyl transferase (ACAT) enzyme activity by inhibiting ACAT activity which comprises administering to a patient in need of such treatment an effective ACAT inhibiting amount of a compound according to claim 14.

21. The method according to claim 20, wherein said inhibiting ACAT activity results in decreased intestinal absorption of cholesterol.

22. The method according to claim 20, wherein said inhibiting ACAT activity results in decreased cholesterol accumulation on an arterial wall.

23. The method as claimed in claim 20, in which said disease is arteriosclerosis.

* * * * *